US007411052B2

(12) United States Patent
Tang

(10) Patent No.: US 7,411,052 B2
(45) Date of Patent: Aug. 12, 2008

(54) METHODS AND MATERIALS RELATING TO STEM CELL GROWTH FACTOR-LIKE POLYPEPTIDES AND POLYNUCLEOTIDES

(75) Inventor: Y. Tom Tang, San Jose, CA (US)

(73) Assignee: Nuvelo, Inc., San Carlos, CA (US)

( * ) Notice: Subject to any disclaimer, the term of this patent is extended or adjusted under 35 U.S.C. 154(b) by 266 days.

(21) Appl. No.: 10/488,423

(22) PCT Filed: Aug. 30, 2002

(86) PCT No.: PCT/US02/27746

§ 371 (c)(1),
(2), (4) Date: Mar. 3, 2004

(87) PCT Pub. No.: WO03/029405

PCT Pub. Date: Apr. 10, 2003

(65) Prior Publication Data

US 2008/0051565 A1    Feb. 28, 2008

Related U.S. Application Data

(63) Continuation-in-part of application No. 10/125,852, filed on Apr. 19, 2002, now abandoned, which is a continuation-in-part of application No. 09/799,451, filed on Mar. 5, 2001, now Pat. No. 6,783,969.

(60) Provisional application No. 60/316,368, filed on Aug. 30, 2001, provisional application No. 60/339,739, filed on Dec. 10, 2001.

(51) Int. Cl.
*A61K 38/24* (2006.01)
*C07K 1/00* (2006.01)
*C07H 21/02* (2006.01)
*C12Q 1/68* (2006.01)

(52) U.S. Cl. ............... 530/399; 530/350; 536/23.1; 536/23.5; 435/6; 435/69.1; 435/69.4

(58) Field of Classification Search .................... None
See application file for complete search history.

(56) References Cited

U.S. PATENT DOCUMENTS

| 5,350,836 | A | 9/1994 | Kopchick et al. |
| 2003/0022217 | A1 | 1/2003 | Ceccardi et al. |
| 2004/0005560 | A1 | 1/2004 | Isogai et al. |
| 2004/0077048 | A1 | 4/2004 | Warren et al. |

FOREIGN PATENT DOCUMENTS

| WO | WO 01/77169 A2 | 10/2001 |
| WO | WO 03/029437 | 4/2003 |

OTHER PUBLICATIONS

GIBCO BRL, GIBCO BRL Catalogue & Reference Guide, 1990, p. 404.*
Database GenBank accession # AAW85607, Jun. 19, 2007. See attached printout of the accession.*
Everett et al., Nature Genetics 17, 411-422, 1997.*
Scott et al., Nature Genetics 21, 440-443, 1999.*
Adams, et al., "The Thrombospondins," *Int J Biochem Cell Biol* 36:961-968 (2004).
Altshchul, et al. "Basic Local Alignment Search Tool," *J Mol Biol* 21:403-410 (1990).
Altschul, et al., "A Protein Alignment Scoring System Sensitive to All Evolutionary Distances," *J Mol Evol* 36:290-300 (1993).
Bjornson, et al., "Turning Brain into Blood: A Hematopoietic Fate Adopted by Neural Stem Cells in Vivo," *Science* 283:534-537 (1999).
Bork, et al., "Go Hunting in Sequence Databases but Watch Out for the Traps," *Trends in Genetics* 12:425-427 (1996).
Bork, "Powers and Pitfalls in Sequence Analysis: The 70% Hurdle," *Genome Res* 10:398-400 (2000).
Brenner, "Errors in Genome Function," *Trends in Genetics* 15:132-133 (1999).
Broudy, "Stem Cell Factor and Hematopoiesis," *Blood* 90:1345-1364 (1997).
Database EMBL; Accession No. AI016251; "ov55g03.s1 Soares_testis_NHT *Homo sapiens* cDNA Clone Image:1641268 3', mRNA Sequence," (1998).
Database EMBL; Accession No. AI797252; "we86d06.x1 Soares_NFL_T_GBCS1 *Homo sapiens* cDNA Clone Image:2347979 3', mRNA Sequence," (1999).
Database EMBL; Accession No. AB016768 "Mus Musculus mRNA for Thrombospondin Type 1 Domain, Complete cds." (1999).
Database EMBL; Accession No. AL513220 "Human DNA Human DNA Sequence from Clone RP11-566C13 on Chromosome 1 Contains the 5' End of the Genefor Nucleolar GTPase (HUMAUNTIG), The Gene for a Novel Protein (FLJ40906) and a CpG Island," (2001).
Database EMBL; Accession No. BC027938 "*Homo sapiens* R-Spondin 2 Homolog (*Xenopus laevis*), mRNA (cDNA Clone MGC:3555 Image:5201681), Complete cds," (2002).
Database Genbank (EST); Accession No. AW161137; Hillier, et al.,;"WashU-NCI Human EST Project," (1999).
Database Genbank (EST); Accension No. AW160873; Hillier, et al.,; "WashU-NCI Human EST Project," (1999).
Database Genbank (EST); Accension No. R52392; Hillier, et al.,; "WashU-NCI Human EST Project," (1999).
Database Genbank; Accession No. AF251057; Mao, et al.,; Direct Submission, (2001).
Doerks, et al., "Protein Anntotation: Detective Work for Function Prediction," *Trends in Genetics* 14:248-250 (1998).
Kamata, et al., Accession No. Q9Z132 (1999).
Kamata, et al., "R-Spondin, A ovel Gene with Thrombospondin Type 1 Domain, was Expressed in the Dorsal Neural Tube and Affected Wnts Mutants," *Biochim Biophys Acta* 1676:51-62 (2004).

(Continued)

*Primary Examiner*—Shubo (Joe) Zhou
(74) *Attorney, Agent, or Firm*—Robins & Pasternak LLP

(57) ABSTRACT

The invention provides novel polynucleotides and polypeptides encoded by such polynucleotides and mutants or variants thereof that correspond to a novel human secreted stem cell growth factor-like polypeptides. Other aspects of the invention include vectors containing processes for producing novel human secreted stem cell growth factor-like polypeptides, and antibodies specific for such polypeptides.

7 Claims, 9 Drawing Sheets

OTHER PUBLICATIONS

Kapur, et al., "The Presence of Novel Amino Acids in the Cytoplasmic Domain of Stem Cell Factor Results in Hematopoietic Defects in Steel17H Mice," *Blood* 94:1915-1925 (1999).

Kazabskaya, et al., "R-Spondin 2 is a Secreted Activator of Wnt/B-Catenin Signaling and is Required for Xenopus Myogenesis," *Developmental Cell* 7:525-534 (2004).

Kilpainen, et al., "Heparin-Binding Growth-Associated Molecule Contains Two Heparin-Binding B-Sheet Domains that are Homologous to the Thrombospondin Type 1 Reqaet," *J Biol Chem* 275:13564-13570 (2000).

Lawler, "The Functions of Thrombospondin-1 and 2," *Curr Opin Cell Biol* 12:634-640 (2000).

Long, et al., Thrombospondin Functions as a Cytoadhesion Molecule for Human Hematopoietic *Progenitor Cells Blood* 75:2311-2318 (1990).

Maruyama, et al., "A novel Isoform of Rat Estrogen Receptor Beta with 18 Amino Acid Insertion in the Ligand Binding Domain as a Putative Dominant Negative Regulator of Estrogen Action," *Biochem Biophys Res Commun* 246:142-147 (1998).

Mcginley, et al., "Effect of Fixation and Epitope Retrieval on BrdU Indices in Mammary Carcinomas," *J Histchem Cytochem* 48:355-362 (2000).

Nakayama, "Furin: A Mammalian Subtilisin/Kex2p-like Endoprotease Involved in Processing of a Wide Variety of Precurser Proteins," *Biochem J* 324:625-635 (1997).

Nielsen, et al., "Identification of Prokaryotic and Eukaryotic Signal Peptides and Predication of Their Cleavage Sites," *Protein Engineering* 10:1-6 (1997).

Nielsen, et al., "A Neural Network Method for Identification of Prokaryotic and Eukaryotic Signal Peptides and Prediction of Their Cleavage Sites," *Int J Neural Syst* 8:581-599 (1997).

Ngo, et al., "Conmputational Complexity, Protein Structure Prediction, and the Levinthal Paradox," In: *The Protein Problem and Tertiary Structure Prediction*, Merz and Legrand, Eds. Birkhauser, Boston pp. 492-495 (1994).

Sher, et al., "Mutations Uncouple Human Fibroblast Growth Factor (FGF)-7 Biological Activity and Receptor Bindiong and Support Broad Specificity in the Secondary Receptor Binding Site of FGFs," *J Biol Chem* 274:35016-35022 (1999).

Skolnick, et al., "From Genes to Protein Structure and Function: Novel Applications of Computatuional Approaches in the Genomic Era," *Trends in Biotech* 18:34-39 (2000).

Smith, et al., "The Challenges of Genome Sequence Annotation or 'The Devil in the Details'," *Nature Biotech* 15:1222-1223 (1997).

Thomson, et al., "Embryonic Stem Cell Lines Derived from Human Blastocysts," *Science* 282:1145-1147 (1998).

Ward, et al., "Insulin and Epidermal Growth Factor Receptors Contain the Cysteine Repeat Motif Found in the Tumor Necrosis Factor Receptor," *Proteins: Structure, Function and Genetics* 22:141-153 (1995).

Watt, et al., "Out of Eden: Stem Cells and Their Niches," *Science* 287:1427-1430 (2000).

Wells "Additivity of Mutational Effects in Proteins," Biochemistry 29:8509-8517 (1990).

Wuyts, et al., "Nh2-and COOH-Terminal Truncations of Murine Granulocyte Chemotactic Protein-2 Augment the in Vitro and In Vivo Neutrophil Chemotactic Potency," *J Immunol* 163:6155-6263 (1999).

Zhou, et al., "Proteolytic Processing in the Secretory Pathway," *J Biol Chem* 274:20745-20748 (1999).

\* cited by examiner

BLASTP ALIGNMENT OF SEQ ID NO: 3 NOVEL STEM CELL GROWTH FACTOR-LIKE POLYPEPTIDE WITH
HUMAN CLONE 1 THROMBOSPONDIN mRNA, COMPLETE CDS SEQ ID NO: 23

```
>gi|3625176 AF251057   15-APR-2001  clone 1 thrombospondin mRNA, complete cds.
 [Homo sapiens]
 Length = 272

Score =  574 (207.1 bits), Expect = 3.0e-55, P = 3.0e-55
Identities = 107/232 (46%), Positives = 141/232 (60%)

SEQ ID NO 3:     1  MQPRLFSFALLILNCMDYSHCQG-NRWRRSKRGGSFSAKASYVSNPICKGCLSCSKDNGC  59
                    M  RL S+   IliN M+Y    Q  +R RR +R         VS     GC +CS  NGC
SEQ ID NO 23:    1  MHLRLLISWLFIILNFMEYIGSQNASRGRRQRR------MHPNVSQGCQGGCATCSDYNGC  54

SEQ ID NO 3:    60  SRCQQKLFFLRREGMRQYGECLHSCPSGYYGHRAPDMNRCARCRIENCDSCFSKDFCTK  119
                    C+ +LFF L R GM+Q G CL  SCPSGYYG  R  PD+N+C  +C+ +  CD+CF+K+FCTK
SEQ ID NO 23:   55  LSCKPRLFFALERIGMKQIGVCLSSCPSGYYGTRYPDINKCITKCKAD-CDTCFNKNFCTK  113

SEQ ID NO 3:   120  CKVGFYLHRGRCFDECPDGFAPLEETMECVE--GCEVGHWSEWGTCSRQNRTCGFKWGLE  177
                    CK GFYLH G+C D CP+G              TMECV       CEV  W+ W  C++  +TCGFK G E
SEQ ID NO 23:  114  CKSGFYLHLGKCLDNCPEGLEANNHTMECVSIVHCEVSEWNPWSPCTKKGKTCGFKRGTE  173

SEQ ID NO 3:   178  TRTRQIVKKPVKDTIPCPTIAESRRCKQMTMRHCPGGKRTPKAKEKRNKKKKR  229
                    TR R+I++ P       CP    E+R+C +     C    G+R  K +E++  KK    +
SEQ ID NO 23:  174  TRVREIIQHPSAKGNLCPPTNETPRKCTVQRKKCQKGERGKKGRERKRKKPNK  225
```

FIGURE 1

BLASTP ALIGNMENT OF SEQ ID NO: 3 NOVEL STEM CELL GROWTH FACTOR-LIKE POLYPEPTIDE WITH
HUMAN SECRETED PROTEIN CLONE da228_6 SEQ ID NO: 25

```
>AAW85607   AAW85607   05-NOV-1998 23-APR-1998 23-APR-1998 02-MAR-1999 24-APR-1998 Secreted
            protein clone da228_6.     [Homo sapiens]
            Length = 292

Score = 574 (207.1 bits), Expect = 3.5e-56, P = 3.5e-56
Identities = 107/232 (46%), Positives = 141/232 (60%)

SEQ ID NO 3:     1 MQFRLFSFALLILNCMDYSHCQG-NRMWRRSKRGGSFSAKASYVSNPICKGCLSCSKDNGC  59
                   M  RL S+   ILLN M+Y    Q  +R RR +R              VS     GC +CS  NGC
SEQ ID NO 25:    1 MHLRLLSWLPIILNFMEYIGSQNASRGRRQRR------MHPNVSQGCQGGCATCSDYNGC   54

SEQ ID NO 3:    60 SRCQQKLFFFLRREGMRQYGECLHSCPSGYYGHRAPDMNRCARCRIENCDSCFSKDFCTK  119
                   C+ +LFF L R GM+Q G CL SCPSGYYG R PD+N+C  +C+ +  CD+CF+K+FCTK
SEQ ID NO 25:   55 LSCKEPRLFFALERIGMKQIGVCLSSCPSGYYGTRYPDINKCTKCKAD-CDTCFNKNFCTK  113

SEQ ID NO 3:   120 CKVGFYLHRGRCFDECPDGFAPLEETMECVE--GCEVGHWSEWGTCSRNNRTCGFKWGLE  177
                   CK GFYLH G+C D CP+G        TMECV     CEV  W+ W  C++  +TCGFK G E
SEQ ID NO 25:  114 CKSGFYLHLGKCLDNCPEGLEANNHTMECVSIVHCEVSEWNPWSPCTKKGKTCGFKRGTE  173

SEQ ID NO 3:   178 TRTRQIVKKPVKDTIPCPTLAESRRCKMTMRHCPGGKRTPKAKEKRNKKKR          229
                   TR R+I++  P       CP   E+R+C  + + C  G+R  K   +E++ KK   +
SEQ ID NO 25:  174 TRVRELIQHPSAKGNLCPPTNETRKCTVQRKKCQKGERGKKGRERKRKPNK         225
```

FIGURE 2

BLASTP ALIGNMENT OF SEQ ID NO: 9 NOVEL STEM CELL GROWTH FACTOR-LIKE POLYPEPTIDE WITH
HUMAN CLONE 1 THROMBOSPONDIN mRNA, COMPLETE CDS SEQ ID NO: 23

```
>gi|13625176 AF251057   15-APR-2001   clone 1 thrombospondin mRNA, complete cds.
           [Homo sapiens]
           Length = 272

Score = 227 (85.0 bits), Expect = 1.8e-18, P = 1.8e-18
Identities = 53/120 (44%), Positives = 67/120 (55%)

SEQ ID NO 9:    1  MQFRLFSFALILNCMDYSHCQG-NRWRRSKRGGSFSAKASYVSNPICKGCLSCSKDNGC  59
                   M  RL S+    IILN M+Y  Q   +R RR +R         VS      GC +CS  NGC
SEQ ID NO 23:   1  MHLRLISWLPILLNFMEYIGSQNASRGRRQRR------MHPNVSQGCQGGCATCSDYNGC  54

SEQ ID NO 9:   60  SRCQQKLPFFLRREGMRQYGECLHSCPSGYYGHRAPDMNRCATYKLPEEDMFHLGKDSCS  119
                   C+ +LPF L R GM+Q G CL  SCPSGYYG      R PD+N+C    K    +  F+ K+ C+
SEQ ID NO 23:  55  LSCKPRLFFALERIGMKQIGVCLSSCPSGYYGTRYPDINKCTKCKADCDTCFN--KNFCT  112
```

FIGURE 3

BLASTP ALIGNMENT OF SEQ ID NO: 9 NOVEL STEM CELL GROWTH FACTOR-LIKE POLYPEPTIDE WITH
HUMAN SECRETED PROTEIN CLONE da228_6 SEQ ID NO: 25

```
>AAW85607    AAW85607   05-NOV-1998 23-APR-1998 02-MAR-1999 24-APR-1998 Secreted
             protein clone da228_6.  [Homo sapiens]
             Length = 292

Score = 227 (85.0 bits), Expect = 2.1e-19, P = 2.1e-19
Identities = 53/120 (44%), Positives = 67/120 (55%)

SEQ ID NO 9:    1 MQFRLFSFALIILNCMDYSHCQG-NRWRRSKRGGSFSAKASYVSNPICKGCLSCSKDNGC 59
                  M  RL S+   IILN M+Y     Q     +R RR +R          VS    GC +CS   NGC
SEQ ID NO 25:   1 MHLRLISWLFIILNFMEYIGSQNASRGRRQRR------MHPNVSQGCQGGCATCSDYNGC 54

SEQ ID NO 9:   60 SRCQQKLFFFLRREGMRQYGECLHSCPSGYYGHRAPDMNRCAIYKLPEEDMFHLGKDSCS 119
                  C+ +LFF L R  GM+Q G CL SCPSGYYG  +         R PD+N+C    K   + F+ K+ C+
SEQ ID NO 25:  55 LSCKPRLFFALERIGMKQIGVCLSSCPSGYYGTRYPDINKCTKCKADCDTCFN--KNFCT 112

Score = 65 (27.9 bits), Expect = 8.0, P = 1.00
Identities = 14/43 (32%), Positives = 21/43 (48%)

SEQ ID NO 9:   47 CKG-CLSCSKDNGCSRCQQKLFFFLRREGMRQYGECLHSCPSG 88
                  CK  C  C   N C++C+   +   L       G+CL  +CP G
SEQ ID NO 25:  98 CKADCDTCFNKNFCTKCKSGFYLHL---------GKCLDNCPEG 132
```

FIGURE 4

BLASTP ALIGNMENT OF SEQ ID NO: 13 NOVEL STEM CELL GROWTH FACTOR-LIKE POLYPEPTIDE WITH HUMAN CLONE 1 THROMBOSPONDIN mRNA, COMPLETE CDS SEQ ID NO: 23

```
>gi|13625176 AF251057    15-APR-2001  clone 1 thrombospondin mRNA, complete cds.
            [Homo sapiens]
            Length = 272

Score = 586 (211.3 bits), Expect = 1.6e-56, P = 1.6e-56
Identities = 106/226 (46%), Positives = 142/226 (62%)

SEQ ID NO 13:    1  MQFRLFSPALILLNCMDYSHCQG-NRWRRSKRASYVSNPICKG-CLSCSKDNGCSRCQQK    58
                    M  RL S+  ILIN M+Y     Q  +R RR +R    +     C+G C +CS NGC    C+ +
SEQ ID NO 23:    1  MHLRLISMLFIILNFMEYIGSQNASRGRRQRRMHPNVSQGCQGGCATCSDYNGCLSCKPR    60

SEQ ID NO 13:   59  LFFFLRREGMRQYGECLHSCPSGYYGHRAPDMNRCARCRIENCDSCFSKDFCTRCKVGFY   118
                    LFF L R GM+Q G CL SCPSGYYG  R      +C  C +  CD+CF+ K+FCTKCK  GFY
SEQ ID NO 23:   61  LFFALERIGMKQIGVCLSSCPSGYYGTRYPDINKCTKCKAD--CDTCFNKFCTKCKSGFY   119

SEQ ID NO 13:  119  LHRGRCFDECPCDGFAPLEETMECVE--GCEVGHWSEWGTCSRNNRTCGFKWNGLETRTRQI   176
                    LH G+C D CP+G         TMECV      CEV  W+ W  C++  +TCGFK G ETR R+I
SEQ ID NO 23:  120  LHLGKCLDNCPEGLEANNHTMECVSIVHCEVSEWNPWSPCTKKGKTCGFKRGTETRVREI   179

SEQ ID NO 13:  177  VKKPVKDTIPCPTIAESRRCKMTMRHCPGGKRTPKAKEKRNKKKKR   222
                    ++ P    CP   E+R+C +    + C  G+R    K +E++ KK  +
SEQ ID NO 23:  180  IQHPSAKGNLCPPTNETRKCTVQRKKCQKGERGKKGRERKRKKPNK   225
```

FIGURE 5

BLASTP ALIGNMENT OF SEQ ID NO: 13 NOVEL STEM CELL GROWTH FACTOR-LIKE POLYPEPTIDE WITH
HUMAN SECRETED PROTEIN CLONE da228_6 SEQ ID NO: 25

```
>AAW85607   AAW85607   05-NOV-1998  23-APR-1998  02-MAR-1999  24-APR-1998  Secreted
            protein clone da228_6.    [Homo sapiens]
            Length = 292

Score = 586 (211.3 bits), Expect = 1.9e-57, P = 1.9e-57
Identities = 106/226 (46%), Positives = 142/226 (62%)

SEQ ID NO 13:    1 MQFRLFSFALILLNCMDYSHCQG-NRWRRSKRASYVSNPICKG-CLSCSKDNGCSRCQQK  58
                   M  RL S+  IIL M+Y  Q      +R RR SK    +R       C+G C +CS  NGC    C+  +
SEQ ID NO 25:    1 MHLRLISWLFIILNFMEYIGSQNASRGRRQRRMHPNVSQGCQGGCATCSDYNGCLSCKPR  60

SEQ ID NO 13:   59 LFFFLRREGMRQYGECLHSCPSGYYGHRAPDMNRCARCRIENCDSCFSKDFCTKCKVGFY 118
                   LFF  L R GM+Q  G CL  SCPSGYYG R  PD+N+C  +C+ + CD+CF+K+FCTKCK GFY
SEQ ID NO 25:   61 LFFALERIGMKQIGVCLSSCPSGYYGTRYPDINKCTKCKAD-CDTCFNKNFCTKCKSGFY 119

SEQ ID NO 13:  119 LHRGRCFDECPDGFAPLEETMECVE--GCEVGHWSEMGTCSRNNRTCGFKWGLETRTRQI 176
                   LH G+C D CP+G       TMECV     CEV  GHW +  W  C++  +TCGFK  G ETR R+I
SEQ ID NO 25:  120 LHLGKCLDNCPEGLEANNHTMECVSIVHCEVSEWNPWSPCTKKGKTCGFKRGTETRVREI 179

SEQ ID NO 13:  177 VKKPVKDTIPCPTIAESRRCKMTMRHCPGGKRTPKAKEKRNKKKKR 222
                   ++ P          CP  E+R+C +    + C     G+R      K  +E++ KK  +
SEQ ID NO 25:  180 IQHPSAKGNLCPPTNETRKCTVQRKKCQKGERGKKGRERKRKKPNK 225
```

FIGURE 6

BLASTP ALIGNMENT OF SEQ ID NO: 18 NOVEL STEM CELL GROWTH FACTOR-LIKE POLYPEPTIDE WITH MOUSE THROMBOSPONDIN TYPE 1 DOMAIN SEQ ID NO: 24

```
>gi45195541 (AB016768) thrombospondin type 1 domain    [Mus musculus]
         Length = 265

Score = 1298 (462.0 bits), Expect = 5.8e-132, P = 5.8e-132
Identities = 231/262 (88%), Positives = 242/262 (92%)

SEQ ID NO 18:    1 MRLGLCVVALVLSWTHLTISSRGIKGKRQRRISAEGSQACAKGCELCSEINGCLKCSPKL 60
                   MRLGLCVVALVLSWTH+ + SRGIKGKRQRRISAEGSQACAKGCELCSE+NGCLKCSPKL
SEQ ID NO 24:    1 MRLGLCVVALVLSWTHLAVGSRGIKGKRQRRISAEGSQACAKGCELCSEVNGCLKCSPKL 60

SEQ ID NO 18:   61 FILLERNDIRQVGVCLPSCPPGYFDARNPDMNKCIKCKIRHCEACFSHNFCTKCKEGLYL 120
                   FILLERNDIRQVGVCLPSCPPGYFDARNPDMNKCIKCKIRHCEACFSHNFCTKC+E LYL
SEQ ID NO 24:   61 FILLERNDIRQVGVCLPSCPPGYFDARNPDMNKCIKCKIRHCEACFSHNFCTKCQEALYL 120

SEQ ID NO 18:  121 HKGRCYPACPEGSSAANGTMECSSPAQCEMSEWSPWGPCSKKQQLCGFRRGSEERTRRVL 180
                   HKGRCYPACPEGS+AAN TMEC SPAQCEMSEWSPWGPCSKK++LCGFR+GSEERTRRVL
SEQ ID NO 24:  121 HKGRCYPACPEGSTAANSTMECGSPAQCEMSEWSPWGPCSKKRKLCGFRKGSEERTRRVL 180

SEQ ID NO 18:  181 HAPVGDHAACSDTKETRRCTVRRVPCPEGQKRRKGGQGRRENANRNLARKESKEAGAGSR 240
                   HAP GDH  CSDTKETR+CTVRR PCPEGQKRRKGGQGRRENANR+ ARK SKE + SR
SEQ ID NO 24:  181 HAPGGDHTTCSDTKETRKCTVRRTPCPEGQKRRKGGQGRRENANRHPARKNSKEPRSNSR 240

SEQ ID NO 18:  241 RRKGQQQQQQQGTVGPLTSAGP 262
                   R KGQQQ Q  GT GPLTS GP
SEQ ID NO 24:  241 RHKGQQQPQP-GTTGPLTSVGP 261
```

FIGURE 7

BLASTP ALIGNMENT OF SEQ ID NO: 18 NOVEL STEM CELL GROWTH FACTOR-LIKE POLYPEPTIDE WITH
HUMAN CLONE 1 THROMBOSPONDIN mRNA, COMPLETE CDS SEQ ID NO: 23

>gi|13625176 AF251057  15-APR-2001  clone 1 thrombospondin mRNA, complete cds.
 [Homo sapiens]
 Length = 272

Score = 646 (232.5 bits), Expect = 7.1e-63, P = 7.1e-63
Identities = 113/242 (46%), Positives = 154/242 (63%)

```
SEQ ID NO 18:   10 LVLSWTHLJTISSRGIKGKRQRRISAEGSQACAKGCELCSEINGCLKCSPKLFILLERNDI  69
                   ++L++     S    +G+RQRR+      SQ C   GC   CS+ NGCL C P+LF  LER  +
SEQ ID NO 23:   11 IILNFMEYTGSQNASRGRRQRRMHPNVSQGCQGGCATCSDYNGCLSCKPRLFFALERIGM  70

SEQ ID NO 18:   70 RQVGVCLPSCPPGYFDARNPDMNKCTKCKIEHCEACFSHNFCTKCKEGLYLHKGRCYPAC 129
                   +Q+GVCL SCP GY+      R  PD+NKC KCK  +  C+  CF+  NFCTKCK G YLH G+C
SEQ ID NO 23:   71 KQIGVCLSSCPSGYYGTRYPDINKCTKCKAD-CDTCPNKNFCTKCKSGFYLHLGKCLDNC 129

SEQ ID NO 18:  130 PEGSSAANGTMECSSPAQCEMSEWSPWGPCSKKQQLCGFPRRGSEERTRRVLHAPVGDHAA 189
                   PEG   A N TMEC S    CE+SEW+PW PC+KK +  CGF+RG+E R R ++  P
SEQ ID NO 23:  130 PEGLEAANNHTMECVSIVHCEVSEWNPWSPCTKKGKTCGFYKRGTETRVREIIQHPSAKGNL 189

SEQ ID NO 18:  190 CSDTKETRRCTVRRVPCPEGQKRRKGGQGRRENANRNLARKESKEAGAGSRRRKGQQQQQ 249
                    C  T  ETR+CTV+R   C    +G++ +KG    GR+E+A+R N+     ESKEA   S+  +  ++
SEQ ID NO 23:  190 CPPTNETRKCTVQRKKCQKGERGKKGRERKRKKPNKG----ESKEALPDSKSLESSKEIP 245

SEQ ID NO 18:  250 QQ 251
                   +Q
SEQ ID NO 23:  246 EQ 247
```

FIGURE 8

BLASTP ALIGNMENT OF SEQ ID NO: 18 NOVEL STEM CELL GROWTH FACTOR-LIKE POLYPEPTIDE WITH HUMAN SECRETED PROTEIN CLONE da228_6 SEQ ID NO: 25

```
>AAW85607   AAW85607   05-NOV-1998  23-APR-1998 02-MAR-1999 24-APR-1998 Secreted
            protein clone da228_6 [Homo sapiens]
            Length = 292

Score = 646 (232.5 bits), Expect = 8.3e-64, P = 8.3e-64
Identities = 113/242 (46%), Positives = 154/242 (63%)

SEQ ID NO 18:    10  LVLSWTHLTISSRGIKGKRQRRISAEGSQACAKGCELCSEINGCLKCSPKLFILLERNDI   69
                     ++L+++   S    +G+RQRR+         SQ C  GC  CS+ NGCL C P+LF  LER +
SEQ ID NO 25:    11  IILNFMEYIGSQNASRGRRQRRMFPNVSGCQGGCATCSDYNGCLSCKPRLFFALERIGM   70

SEQ ID NO 18:    70  RQVGVCLPSCPPGYFDARNPDMNKCIKCKIEHCEACFSHNFCTKCKEGLYLHKGRCYPAC  129
                     +Q+GVCL SCP GY+   R   PD+NKC KCK + C+ CF+ NFCTKCK  G YLH G+C   C
SEQ ID NO 25:    71  KQIGVCLSSCPSGYYGTRYPDINKCTKCKAD-CDTCFNKNFCTKCKSGFYLHLGKCLDNC  129

SEQ ID NO 18:   130  PEGSSAANGTMECSSPAQCEMSEWSPWGPCSKKQQLCGFRRGSEERTRRVLHAPVGDHAA  189
                     PEG  A N TMEC S     CE+SEW+PW  PC+KK + CGF+RG+E R R ++  P
SEQ ID NO 25:   130  PEGLEANNHTMECVSIVHCEVSEWNPWSPCTKGKRTCGFKRGTETRVRELIQHPSAKGNL  189

SEQ ID NO 18:   190  CSDTKETRRCTVRRVPCPEGQKRPKKGGQGRRENANRNLARKESKEAGAGSRRRKGQQQQ  249
                     C  T ETR+CTV+R    C  +G++   C    +KG + +R+  N+       ESKEA  S+ + ++
SEQ ID NO 25:   190  CPPTNETRKCTVQRKKCQKGERGKKGRERKRKKPNKG----ESKEAIPDSKSLESSKEIP  245

SEQ ID NO 18:   250  QQ  251
                     +Q
SEQ ID NO 25:   246  EQ  247
```

FIGURE 9 under which terms US 7,411,052 B2 appears on page.

SEQUENCE LISTING

```
<160> NUMBER OF SEQ ID NOS: 27

<210> SEQ ID NO 1
<211> LENGTH: 427
<212> TYPE: DNA
<213> ORGANISM: Homo sapiens

<400> SEQUENCE: 1
tttcgtggcg agtctccctc tgagtcctcc ccagcagcgc ggccggcgcc ggctctttgg      60
gcgaaccctc cagttcctag actttgagag gcgtctctcc cccgcccgac cgcccagatg     120
cagtttcgcc ttttctcctt tgccctcatc attctgaact gcatggatta cagccactgc     180
```

| | |
|---|---|
| caaggcaacc gatggagacg cagtaagcga ggtgggtcct tctctgccaa agctagttat | 240 |
| gtatcaaatc ccatttgcaa gggttgtttg tcttgttcaa aggacaatgg gtgtagccga | 300 |
| tgtcaacaga agttgttctt cttccttcga agagaaggga tgcgccagta tggagagtgc | 360 |
| ctgcattcct gcccatccgg gtactatgga caccgagccc cagatatgaa cagatgtgca | 420 |
| agatgca | 427 |

<210> SEQ ID NO 2
<211> LENGTH: 2028
<212> TYPE: DNA
<213> ORGANISM: Homo sapiens
<220> FEATURE:
<221> NAME/KEY: CDS
<222> LOCATION: (672)..(1424)
<223> OTHER INFORMATION:

<400> SEQUENCE: 2

| | |
|---|---|
| atgaactgtg cttttgaaaa catcaaggac atgaatgaca acaccacct acttatagaa | 60 |
| gcatcccaag cctcagccgg tctgcatctc catcggaaag tgcgcttgcc acatcccttc | 120 |
| ggatcacttc gtcctcccga gagcgttctg ccttctacag ctcggaaaga agaaatctt | 180 |
| agctgtgaag tgaccgtgga gaaagcgcag gaagcgacac aattggttag ggaggcagag | 240 |
| agtgtgagcg gcgcacccc ttgcctgggg accgcgctcg cgggcgggga cggagcatcc | 300 |
| cagtggctgc acccgccgct ccgcgctcct gcctggcgtc gccaaccccg cggcggccgc | 360 |
| tggaattcca gagctgccag gcgctcccag ccggtctcgg caaactttc cccagcccac | 420 |
| gtgctaacca agcggctcgc ttcccgagcc cgggatggag caccgcgcct agggaggccg | 480 |
| cgccgcccga gacgtgcgca cggttcgtgg cggagagatg ctgatcgcgc tgaactgacc | 540 |
| ggtgcggccc gggggtgagt ggcgagtctc cctctgagtc ctccccagca gcgcggccgg | 600 |
| cgccggctct ttgggcgaac cctccagttc ctagactttg agaggcgtct ctcccccgcc | 660 |
| cgaccgccca g atg cag ttt cgc ctt ttc tcc ttt gcc ctc atc att ctg | 710 |
|              Met Gln Phe Arg Leu Phe Ser Phe Ala Leu Ile Ile Leu | |
|               1           5               10 | |
| aac tgc atg gat tac agc cac tgc caa ggc aac cga tgg aga cgc agt | 758 |
| Asn Cys Met Asp Tyr Ser His Cys Gln Gly Asn Arg Trp Arg Arg Ser | |
|  15               20               25 | |
| aag cga ggt ggg tcc ttc tct gcc aaa gct agt tat gta tca aat ccc | 806 |
| Lys Arg Gly Gly Ser Phe Ser Ala Lys Ala Ser Tyr Val Ser Asn Pro | |
| 30             35               40               45 | |
| att tgc aag ggt tgt ttg tct tgt tca aag gac aat ggg tgt agc cga | 854 |
| Ile Cys Lys Gly Cys Leu Ser Cys Ser Lys Asp Asn Gly Cys Ser Arg | |
|               50               55               60 | |
| tgt caa cag aag ttg ttc ttc ttc ctt cga aga gaa ggg atg cgc cag | 902 |
| Cys Gln Gln Lys Leu Phe Phe Phe Leu Arg Arg Glu Gly Met Arg Gln | |
|  65               70               75 | |
| tat gga gag tgc ctg cat tcc tgc cca tcc ggg tac tat gga cac cga | 950 |
| Tyr Gly Glu Cys Leu His Ser Cys Pro Ser Gly Tyr Tyr Gly His Arg | |
|         80               85               90 | |
| gcc cca gat atg aac aga tgt gca aga tgc aga ata gaa aac tgt gat | 998 |
| Ala Pro Asp Met Asn Arg Cys Ala Arg Cys Arg Ile Glu Asn Cys Asp | |
|      95               100             105 | |
| tct tgc ttt agc aaa gac ttt tgt acc aag tgc aaa gta ggc ttt tat | 1046 |
| Ser Cys Phe Ser Lys Asp Phe Cys Thr Lys Cys Lys Val Gly Phe Tyr | |
| 110            115             120             125 | |
| ttg cat aga ggc cgt tgc ttt gat gaa tgt cca gat ggt ttt gca cca | 1094 |
| Leu His Arg Gly Arg Cys Phe Asp Glu Cys Pro Asp Gly Phe Ala Pro | |
|              130             135             140 | |

```
tta gaa gaa acc atg gaa tgt gtg gaa gga tgt gaa gtt ggt cat tgg       1142
Leu Glu Glu Thr Met Glu Cys Val Glu Gly Cys Glu Val Gly His Trp
            145                 150                 155 agc gaa tgg gga act tgt agc aga aat aat cgc aca tgt gga ttt aaa       1190
Ser Glu Trp Gly Thr Cys Ser Arg Asn Asn Arg Thr Cys Gly Phe Lys
        160                 165                 170 tgg ggt ctg gaa acc aga aca cgg caa att gtt aaa aag cca gtg aaa       1238
Trp Gly Leu Glu Thr Arg Thr Arg Gln Ile Val Lys Lys Pro Val Lys
    175                 180                 185 gac aca ata ccg tgt cca acc att gct gaa tcc agg aga tgc aag atg       1286
Asp Thr Ile Pro Cys Pro Thr Ile Ala Glu Ser Arg Arg Cys Lys Met
190                 195                 200                 205 aca atg agg cat tgt cca gga ggg aag aga aca cca aag gcg aag gag       1334
Thr Met Arg His Cys Pro Gly Gly Lys Arg Thr Pro Lys Ala Lys Glu
                210                 215                 220 aag agg aac aag aaa aag aaa agg aag ctg ata gaa agg gcc cag gag       1382
Lys Arg Asn Lys Lys Lys Arg Lys Leu Ile Glu Arg Ala Gln Glu
            225                 230                 235 caa cac agc gtc ttc cta gct aca gac aga gct aac caa taa               1424
Gln His Ser Val Phe Leu Ala Thr Asp Arg Ala Asn Gln
        240                 245                 250 aacaagagat ccggtagatt tttaggggtt tttgttttg caaatgtgca caaagctact      1484
ctccactcct gcacactggt gtgcagcctt tgtgctgctc tgcccagtat ctgttcccag     1544
taacatggtg aaaggaagca ccaccagcat ggcccctgtg ttatttatgc tttgatttga     1604
atctggagac tgtgaaggca ggagtaagtg cacagcccgt gacttggctc agtgtgtgct    1664
gagagaatcc gtccccggca ccatggacat gctagaggtg tgaggctgca gaacaccgct    1724
ggaggacgga cttgtgccta tttatgtgaa agaaagatgct tggcaggcaa tgcgctactc   1784
acgtcgtgac ctttatttct cacattgtgc attttcaagg atatgtttgt gtggatatct    1844
gcttagtgtt accacatggt attctcagca tgttaccttc acactgttgt gcgatgaaac    1904
tgcttttagc tgaggatatg ctctggaaat tcctgctcag tttcactgca gccctaatat    1964
gtacatatac tgcaggagct acatataaag ctcttattta ctgtatattt atgctttctt    2024
gtgg                                                                  2028

<210> SEQ ID NO 3
<211> LENGTH: 250
<212> TYPE: PRT
<213> ORGANISM: Homo sapiens

<400> SEQUENCE: 3

Met Gln Phe Arg Leu Phe Ser Phe Ala Leu Ile Ile Leu Asn Cys Met
1               5                   10                  15

Asp Tyr Ser His Cys Gln Gly Asn Arg Trp Arg Arg Ser Lys Arg Gly
            20                  25                  30

Gly Ser Phe Ser Ala Lys Ala Ser Tyr Val Ser Asn Pro Ile Cys Lys
        35                  40                  45

Gly Cys Leu Ser Cys Ser Lys Asp Asn Gly Cys Ser Arg Cys Gln Gln
    50                  55                  60

Lys Leu Phe Phe Phe Leu Arg Arg Glu Gly Met Arg Gln Tyr Gly Glu
65                  70                  75                  80

Cys Leu His Ser Cys Pro Ser Gly Tyr Tyr Gly His Arg Ala Pro Asp
                85                  90                  95

Met Asn Arg Cys Ala Arg Cys Arg Ile Glu Asn Cys Asp Ser Cys Phe
            100                 105                 110
```

```
Ser Lys Asp Phe Cys Thr Lys Cys Lys Val Gly Phe Tyr Leu His Arg
        115                 120                 125

Gly Arg Cys Phe Asp Glu Cys Pro Asp Gly Phe Ala Pro Leu Glu Glu
        130                 135                 140

Thr Met Glu Cys Val Glu Gly Cys Glu Val Gly His Trp Ser Glu Trp
145                 150                 155                 160

Gly Thr Cys Ser Arg Asn Asn Arg Thr Cys Gly Phe Lys Trp Gly Leu
                165                 170                 175

Glu Thr Arg Thr Arg Gln Ile Val Lys Lys Pro Val Lys Asp Thr Ile
                180                 185                 190

Pro Cys Pro Thr Ile Ala Glu Ser Arg Arg Cys Lys Met Thr Met Arg
                195                 200                 205

His Cys Pro Gly Gly Lys Arg Thr Pro Lys Ala Lys Glu Lys Arg Asn
        210                 215                 220

Lys Lys Lys Lys Arg Lys Leu Ile Glu Arg Ala Gln Glu Gln His Ser
225                 230                 235                 240

Val Phe Leu Ala Thr Asp Arg Ala Asn Gln
                245                 250

<210> SEQ ID NO 4
<211> LENGTH: 753
<212> TYPE: DNA
<213> ORGANISM: Homo sapiens

<400> SEQUENCE: 4
atgcagtttc gccttttctc ctttgccctc atcattctga actgcatgga ttacagccac      60
tgccaaggca accgatggag acgcagtaag cgaggtgggt ccttctctgc aaaagctagt     120
tatgtatcaa atcccatttg caagggttgt ttgtcttgtt caaaggacaa tgggtgtagc     180
cgatgtcaac agaagttgtt cttcttcctt cgaagagaag ggatgcgcca gtatggagag     240
tgcctgcatt cctgcccatc cgggtactat ggacaccgag ccccagatat gaacagatgt     300
gcaagatgca gaatagaaaa ctgtgattct tgctttagca agacttttg taccaagtgc     360
aaagtaggct tttatttgca tagaggccgt tgctttgatg aatgtccaga tggttttgca     420
ccattagaag aaaccatgga atgtgtggaa ggatgtgaag ttggtcattg gagcgaatgg     480
ggaacttgta gcagaaataa tcgcacatgt ggatttaaat ggggtctgga aaccagaaca     540
cggcaaattg ttaaaaagcc agtgaaagac acaataccgt gtccaaccat tgctgaatcc     600
aggagatgca gatgacaat gaggcattgt ccaggaggga gagaacacc aaaggcgaag     660
gagaagagga acaagaaaaa gaaaaggaag ctgatagaaa gggcccagga gcaacacagc     720
gtcttcctag ctacagacag agctaaccaa taa                                 753

<210> SEQ ID NO 5
<211> LENGTH: 21
<212> TYPE: PRT
<213> ORGANISM: Homo sapiens

<400> SEQUENCE: 5

Met Gln Phe Arg Leu Phe Ser Phe Ala Leu Ile Ile Leu Asn Cys Met
1               5                   10                  15

Asp Tyr Ser His Cys
            20

<210> SEQ ID NO 6
<211> LENGTH: 229
```

```
<212> TYPE: PRT
<213> ORGANISM: Homo sapiens

<400> SEQUENCE: 6

Gln Gly Asn Arg Trp Arg Arg Ser Lys Arg Gly Gly Ser Phe Ser Ala
1               5                   10                  15

Lys Ala Ser Tyr Val Ser Asn Pro Ile Cys Lys Gly Cys Leu Ser Cys
                20                  25                  30

Ser Lys Asp Asn Gly Cys Ser Arg Cys Gln Gln Lys Leu Phe Phe Phe
            35                  40                  45

Leu Arg Arg Glu Gly Met Arg Gln Tyr Gly Cys Leu His Ser Cys
    50                  55                  60

Pro Ser Gly Tyr Tyr Gly His Arg Ala Pro Asp Met Asn Arg Cys Ala
65              70                  75                  80

Arg Cys Arg Ile Glu Asn Cys Asp Ser Cys Phe Ser Lys Asp Phe Cys
                85                  90                  95

Thr Lys Cys Lys Val Gly Phe Tyr Leu His Arg Gly Arg Cys Phe Asp
            100                 105                 110

Glu Cys Pro Asp Gly Phe Ala Pro Leu Glu Glu Thr Met Glu Cys Val
        115                 120                 125

Glu Gly Cys Glu Val Gly His Trp Ser Glu Trp Gly Thr Cys Ser Arg
130                 135                 140

Asn Asn Arg Thr Cys Gly Phe Lys Trp Gly Leu Glu Thr Arg Thr Arg
145                 150                 155                 160

Gln Ile Val Lys Lys Pro Val Lys Asp Thr Ile Pro Cys Pro Thr Ile
                165                 170                 175

Ala Glu Ser Arg Arg Cys Lys Met Thr Met Arg His Cys Pro Gly Gly
            180                 185                 190

Lys Arg Thr Pro Lys Ala Lys Glu Lys Arg Asn Lys Lys Lys Arg
        195                 200                 205

Lys Leu Ile Glu Arg Ala Gln Glu Gln His Ser Val Phe Leu Ala Thr
    210                 215                 220

Asp Arg Ala Asn Gln
225

<210> SEQ ID NO 7
<211> LENGTH: 43
<212> TYPE: PRT
<213> ORGANISM: Homo sapiens

<400> SEQUENCE: 7

Ala Pro Asp Met Asn Arg Cys Ala Arg Cys Arg Ile Glu Asn Cys Asp
1               5                   10                  15

Ser Cys Phe Ser Lys Asp Phe Cys Thr Lys Cys Lys Val Gly Phe Tyr
                20                  25                  30

Leu His Arg Gly Arg Cys Phe Asp Glu Cys Pro
            35                  40

<210> SEQ ID NO 8
<211> LENGTH: 1022
<212> TYPE: DNA
<213> ORGANISM: Homo sapiens
<220> FEATURE:
<221> NAME/KEY: CDS
<222> LOCATION: (627)..(1022)
<223> OTHER INFORMATION:

<400> SEQUENCE: 8
```

```
aaggatcctt aattaaatta atccccccc ccgggtctgc atctccatcg gaaagtgcgc    60
ttgccacatc ccttcggatc acttcgtcct cccgagagcg ttctgccttc tacagctcgg   120
aaagaaagaa atcttagctg tgaagtgacc gtggagaaag cgcaggaagc gacacaattg   180
gttagggagg cagagagtgt gagcgggcgc accccttgcc tggggaccgc gctcgcgggc   240
ggggacggag catcccagtg gctgcacccg ccgctccgcg ctcctgcctg gcgtcgccaa   300
ccccgcggcg gccgctggaa ttccagagct gccaggcgct cccagccggt ctcggcaaac   360
ttttccccag cccacgtgct aaccaagcgg ctcgcttccc gagcccggga tggagcaccg   420
cgcctaggga ggccgcgccg cccgagacgt gcgcacggtt cgtggcggag agatgctgat   480
cgcgctgaac tgaccggtgc ggcccggggg tgagtggcga gtctccctct gagtcctccc   540
cagcagcgcg gccggcgccg gctctttggg cgaaccctcc agttcctaga ctttgagagg   600
cgtctctccc ccgcccgacc gcccag atg cag ttt cgc ctt ttc tcc ttt gcc   653
                                Met Gln Phe Arg Leu Phe Ser Phe Ala
                                  1               5 ctc atc att ctg aac tgc atg gat tac agc cac tgc caa ggc aac cga   701
Leu Ile Ile Leu Asn Cys Met Asp Tyr Ser His Cys Gln Gly Asn Arg
 10              15                  20                  25 tgg aga cgc agt aag cga ggt ggg tcc ttc tct gcc aaa gct agt tat   749
Trp Arg Arg Ser Lys Arg Gly Gly Ser Phe Ser Ala Lys Ala Ser Tyr
                 30                  35                  40 gta tca aat ccc att tgc aag ggt tgt ttg tct tgt tca aag gac aat   797
Val Ser Asn Pro Ile Cys Lys Gly Cys Leu Ser Cys Ser Lys Asp Asn
             45                  50                  55 ggg tgt agc cga tgt caa cag aag ttg ttc ttc ttc ctt cga aga gaa   845
Gly Cys Ser Arg Cys Gln Gln Lys Leu Phe Phe Phe Leu Arg Arg Glu
         60                  65                  70 ggg atg cgc cag tat gga gag tgc ctg cat tcc tgc cca tcc ggg tac   893
Gly Met Arg Gln Tyr Gly Glu Cys Leu His Ser Cys Pro Ser Gly Tyr
     75                  80                  85 tat gga cac cga gcc cca gat atg aac aga tgt gca att tat aaa ctt   941
Tyr Gly His Arg Ala Pro Asp Met Asn Arg Cys Ala Ile Tyr Lys Leu
 90                  95                 100                 105 cca gag gaa gat atg ttc cac ctt gga aag gat tcc tgt tca gat ttc   989
Pro Glu Glu Asp Met Phe His Leu Gly Lys Asp Ser Cys Ser Asp Phe
                110                 115                 120 ttt aga cta cct atg gcg ggg gtg gtg gtt tga                      1022
Phe Arg Leu Pro Met Ala Gly Val Val Val
                125                 130

<210> SEQ ID NO 9
<211> LENGTH: 131
<212> TYPE: PRT
<213> ORGANISM: Homo sapiens

<400> SEQUENCE: 9

Met Gln Phe Arg Leu Phe Ser Phe Ala Leu Ile Ile Leu Asn Cys Met
  1               5                  10                  15

Asp Tyr Ser His Cys Gln Gly Asn Arg Trp Arg Arg Ser Lys Arg Gly
                 20                  25                  30

Gly Ser Phe Ser Ala Lys Ala Ser Tyr Val Ser Asn Pro Ile Cys Lys
             35                  40                  45

Gly Cys Leu Ser Cys Ser Lys Asp Asn Gly Cys Ser Arg Cys Gln Gln
         50                  55                  60

Lys Leu Phe Phe Phe Leu Arg Arg Glu Gly Met Arg Gln Tyr Gly Glu
 65                  70                  75                  80
```

```
Cys Leu His Ser Cys Pro Ser Gly Tyr Tyr Gly His Arg Ala Pro Asp
                85                  90                  95

Met Asn Arg Cys Ala Ile Tyr Lys Leu Pro Glu Glu Asp Met Phe His
            100                 105                 110

Leu Gly Lys Asp Ser Cys Ser Asp Phe Phe Arg Leu Pro Met Ala Gly
        115                 120                 125

Val Val Val
        130

<210> SEQ ID NO 10
<211> LENGTH: 396
<212> TYPE: DNA
<213> ORGANISM: Homo sapiens

<400> SEQUENCE: 10
atgcagtttc gccttttctc ctttgccctc atcattctga actgcatgga ttacagccac      60
tgccaaggca accgatggag acgcagtaag cgaggtgggt ccttctctgc aaaagctagt     120
tatgtatcaa atcccatttg caagggttgt tgtcttgtt  caaaggacaa tgggtgtagc     180
cgatgtcaac agaagttgtt cttcttcctt cgaagagaag ggatgcgcca gtatggagag     240
tgcctgcatt cctgcccatc cgggtactat ggacaccgag ccccagatat gaacagatgt     300
gcaatttata aacttccaga ggaagatatg ttccacttg  gaaaggattc ctgttcagat     360
ttctttagac tacctatggc gggggtggtg gtttga                              396

<210> SEQ ID NO 11
<211> LENGTH: 110
<212> TYPE: PRT
<213> ORGANISM: Homo sapiens

<400> SEQUENCE: 11

Gln Gly Asn Arg Trp Arg Arg Ser Lys Arg Gly Gly Ser Phe Ser Ala
1               5                   10                  15

Lys Ala Ser Tyr Val Ser Asn Pro Ile Cys Lys Gly Cys Leu Ser Cys
            20                  25                  30

Ser Lys Asp Asn Gly Cys Ser Arg Cys Gln Gln Lys Leu Phe Phe Phe
        35                  40                  45

Leu Arg Arg Glu Gly Met Arg Gln Tyr Gly Glu Cys Leu His Ser Cys
    50                  55                  60

Pro Ser Gly Tyr Tyr Gly His Arg Ala Pro Asp Met Asn Arg Cys Ala
65                  70                  75                  80

Ile Tyr Lys Leu Pro Glu Glu Asp Met Phe His Leu Gly Lys Asp Ser
            85                  90                  95

Cys Ser Asp Phe Phe Arg Leu Pro Met Ala Gly Val Val Val
            100                 105                 110

<210> SEQ ID NO 12
<211> LENGTH: 1356
<212> TYPE: DNA
<213> ORGANISM: Homo sapiens
<220> FEATURE:
<221> NAME/KEY: CDS
<222> LOCATION: (262)..(993)
<223> OTHER INFORMATION:

<400> SEQUENCE: 12
cccagcccac gtgctaacca agcggctcgc ttcccgagcc cgggatggag caccgcgcct      60
agggaggccg cgccgcccga gacgtgcgca cggttcgtgg cggagagatg ctgatcgcgc     120
```

```
                                                     -continued tgaactgacc ggtgcggccc gggggtgagt ggcgagtctc cctctgagtc ctccccagca      180
gcgcggccgg cgccggctct ttgggcgaac cctccagttc ctagactttg agaggcgtct      240
ctcccccgcc cgaccgccca g atg cag ttt cgc ctt ttc tcc ttt gcc ctc        291
                         Met Gln Phe Arg Leu Phe Ser Phe Ala Leu
                         1               5                   10 atc att ctg aac tgc atg gat tac agc cac tgc caa ggc aac cga tgg         339
Ile Ile Leu Asn Cys Met Asp Tyr Ser His Cys Gln Gly Asn Arg Trp
                15                  20                  25 aga cgc agt aag cga gct agt tat gta tca aat ccc att tgc aag ggt         387
Arg Arg Ser Lys Arg Ala Ser Tyr Val Ser Asn Pro Ile Cys Lys Gly
        30                  35                  40 tgt ttg tct tgt tca aag gac aat ggg tgt agc cga tgt caa cag aag         435
Cys Leu Ser Cys Ser Lys Asp Asn Gly Cys Ser Arg Cys Gln Gln Lys
            45                  50                  55 ttg ttc ttc ttc ctt cga aga gaa ggg atg cgc cag tat gga gag tgc         483
Leu Phe Phe Phe Leu Arg Arg Glu Gly Met Arg Gln Tyr Gly Glu Cys
    60                  65                  70 ctg cat tcc tgc cca tcc ggg tac tat gga cac cga gcc cca gat atg         531
Leu His Ser Cys Pro Ser Gly Tyr Tyr Gly His Arg Ala Pro Asp Met
75                  80                  85                  90 aac aga tgt gca aga tgc aga ata gaa aac tgt gat tct tgc ttt agc         579
Asn Arg Cys Ala Arg Cys Arg Ile Glu Asn Cys Asp Ser Cys Phe Ser
                95                  100                 105 aaa gac ttt tgt acc aag tgc aaa gta ggc ttt tat ttg cat aga ggc         627
Lys Asp Phe Cys Thr Lys Cys Lys Val Gly Phe Tyr Leu His Arg Gly
            110                 115                 120 cgt tgc ttt gat gaa tgt cca gat ggt ttt gca cca tta gaa gaa acc         675
Arg Cys Phe Asp Glu Cys Pro Asp Gly Phe Ala Pro Leu Glu Glu Thr
        125                 130                 135 atg gaa tgt gtg gaa gga tgt gaa gtt ggt cat tgg agc gaa tgg gga         723
Met Glu Cys Val Glu Gly Cys Glu Val Gly His Trp Ser Glu Trp Gly
    140                 145                 150 act tgt agc aga aat aat cgc aca tgt gga ttt aaa tgg ggt ctg gaa         771
Thr Cys Ser Arg Asn Asn Arg Thr Cys Gly Phe Lys Trp Gly Leu Glu
155                 160                 165                 170 acc aga aca cgg caa att gtt aaa aag cca gtg aaa gac aca ata ccg         819
Thr Arg Thr Arg Gln Ile Val Lys Lys Pro Val Lys Asp Thr Ile Pro
                175                 180                 185 tgt cca acc att gct gaa tcc agg aga tgc aag atg aca atg agg cat         867
Cys Pro Thr Ile Ala Glu Ser Arg Arg Cys Lys Met Thr Met Arg His
            190                 195                 200 tgt cca gga ggg aag aga aca cca aag gcg aag gag aag agg aac aag         915
Cys Pro Gly Gly Lys Arg Thr Pro Lys Ala Lys Glu Lys Arg Asn Lys
        205                 210                 215 aaa aag aaa agg aag ctg ata gaa agg gcc cag gag caa cac agc gtc         963
Lys Lys Lys Arg Lys Leu Ile Glu Arg Ala Gln Glu Gln His Ser Val
220                 225                 230 ttc cta gct aca gac aga gct aac caa taa aacaagagat ccggtagatt          1013
Phe Leu Ala Thr Asp Arg Ala Asn Gln
235                 240 tttaggggtt tttgttttg caaatgtgca caaagctact ctccactcct gcacactggg      1073
gtgcagcctt tgtgctgctc tgcccagtat ctgttcccag taacatggtg aaaggaagca      1133
ccaccaggca tgcccctgtg ttatttatgc tttgatttga atctggagac tgtgaaggca      1193
ggagtaagtg cacagccccg tgacttggct cagtgtgtgc tgagagaatc cgtcccccgc      1253
accatggaca tgctagaggt gtgaggctgc agaacaccgc tggaggacgg acttgtgcct      1313
atttatgtga agaagatgc ttggcaggca atccgcgtgt att                         1356
```

<210> SEQ ID NO 13
<211> LENGTH: 243
<212> TYPE: PRT
<213> ORGANISM: Homo sapiens

<400> SEQUENCE: 13

```
Met Gln Phe Arg Leu Phe Ser Phe Ala Leu Ile Ile Leu Asn Cys Met
1               5                   10                  15

Asp Tyr Ser His Cys Gln Gly Asn Arg Trp Arg Arg Ser Lys Arg Ala
            20                  25                  30

Ser Tyr Val Ser Asn Pro Ile Cys Lys Gly Cys Leu Ser Cys Ser Lys
        35                  40                  45

Asp Asn Gly Cys Ser Arg Cys Gln Gln Lys Leu Phe Phe Leu Arg
    50                  55                  60

Arg Glu Gly Met Arg Gln Tyr Gly Glu Cys Leu His Ser Cys Pro Ser
65                  70                  75                  80

Gly Tyr Tyr Gly His Arg Ala Pro Asp Met Asn Arg Cys Ala Arg Cys
                85                  90                  95

Arg Ile Glu Asn Cys Asp Ser Cys Phe Ser Lys Asp Phe Cys Thr Lys
            100                 105                 110

Cys Lys Val Gly Phe Tyr Leu His Arg Gly Arg Cys Phe Asp Glu Cys
        115                 120                 125

Pro Asp Gly Phe Ala Pro Leu Glu Glu Thr Met Glu Cys Val Glu Gly
    130                 135                 140

Cys Glu Val Gly His Trp Ser Glu Trp Gly Thr Cys Ser Arg Asn Asn
145                 150                 155                 160

Arg Thr Cys Gly Phe Lys Trp Gly Leu Glu Thr Arg Thr Arg Gln Ile
                165                 170                 175

Val Lys Lys Pro Val Lys Asp Thr Ile Pro Cys Pro Thr Ile Ala Glu
            180                 185                 190

Ser Arg Arg Cys Lys Met Thr Met Arg His Cys Pro Gly Gly Lys Arg
        195                 200                 205

Thr Pro Lys Ala Lys Glu Lys Arg Asn Lys Lys Lys Arg Lys Leu
    210                 215                 220

Ile Glu Arg Ala Gln Glu Gln His Ser Val Phe Leu Ala Thr Asp Arg
225                 230                 235                 240

Ala Asn Gln
```

<210> SEQ ID NO 14
<211> LENGTH: 725
<212> TYPE: DNA
<213> ORGANISM: Homo sapiens

<400> SEQUENCE: 14

```
atgcagtttc gccttttctc ctttgccctc atcattctga actgcatgga ttacagccac    60
tgccaaggca accgatggag acgcagtaag cgagctagtt atgtatcaaa tcccatttgc   120
aagggttgtt tgtcttgttc aaaggacaat gggtgtagcc gatgtcaaca gaagttgttc   180
ttcttccttc gaagagaagg gatgcgccag tatggagagt gcctgcattc ctgcccatcc   240
gggtactatg gacaccgagc cccagatatg aacagatgtg caagatgcag aatagaaaac   300
tgtgattctt gctttagcaa agacttttgt accaagtgca agtaggctt ttatttgcat    360 agaggccgtt gctttgatga atgtccagat ggttttgcac cattagaaga aaccatggaa   420
tgtgtggaag atgtgaagt tggtcattgg agcgaatggg gaacttgtag cagaaataat   480
```

```
cgcacatgtg gatttaaatg gggtctggaa accagaacac ggcaaattgt taaaaagcca      540
gtgaaagaca caataccgtg tccaaccatt gctgaatcca ggagatgcaa gatgacaatg      600
aggcattgtc caggagggaa gagaacacca aaggcgaagg agaagaggaa caagaaaaag      660
aaaaggaagc tgatagaaag ggcccaggag caacacagcg tcttcctagc tacagacaga      720
gctaa                                                                 725
```

```
<210> SEQ ID NO 15
<211> LENGTH: 222
<212> TYPE: PRT
<213> ORGANISM: Homo sapiens

<400> SEQUENCE: 15
```

Gln Gly Asn Arg Trp Arg Arg Ser Lys Arg Ala Ser Tyr Val Ser Asn
1               5                   10                  15

Pro Ile Cys Lys Gly Cys Leu Ser Cys Ser Lys Asp Asn Gly Cys Ser
            20                  25                  30

Arg Cys Gln Gln Lys Leu Phe Phe Phe Leu Arg Arg Glu Gly Met Arg
        35                  40                  45

Gln Tyr Gly Glu Cys Leu His Ser Cys Pro Ser Gly Tyr Tyr Gly His
    50                  55                  60

Arg Ala Pro Asp Met Asn Arg Cys Ala Arg Cys Arg Ile Glu Asn Cys
65                  70                  75                  80

Asp Ser Cys Phe Ser Lys Asp Phe Cys Thr Lys Cys Lys Val Gly Phe
                85                  90                  95

Tyr Leu His Arg Gly Arg Cys Phe Asp Glu Cys Pro Asp Gly Phe Ala
            100                 105                 110

Pro Leu Glu Glu Thr Met Glu Cys Val Glu Gly Cys Glu Val Gly His
        115                 120                 125

Trp Ser Glu Trp Gly Thr Cys Ser Arg Asn Asn Arg Thr Cys Gly Phe
    130                 135                 140

Lys Trp Gly Leu Glu Thr Arg Thr Arg Gln Ile Val Lys Lys Pro Val
145                 150                 155                 160

Lys Asp Thr Ile Pro Cys Pro Thr Ile Ala Glu Ser Arg Arg Cys Lys
                165                 170                 175

Met Thr Met Arg His Cys Pro Gly Gly Lys Arg Thr Pro Lys Ala Lys
            180                 185                 190

Glu Lys Arg Asn Lys Lys Lys Arg Lys Leu Ile Glu Arg Ala Gln
        195                 200                 205

Glu Gln His Ser Val Phe Leu Ala Thr Asp Arg Ala Asn Gln
    210                 215                 220

```
<210> SEQ ID NO 16
<211> LENGTH: 380
<212> TYPE: DNA
<213> ORGANISM: Homo sapiens

<400> SEQUENCE: 16
ttcccgggtc gacttcacgc gtcggaggaa gggaggccag ggccggcggg agaatgccaa      60
caggaacctg gccaggaagg agagcaagga ggcgggtgct ggctctcgaa gacgcaaggg      120
gcagcaacag cagcagcagc aagggacagt ggggccactc acatctgcag ggcctgccta      180
gggacactgt ccagcctcca ggcccatgca gaaagagttc agtgctactc tgcgtgattc      240
aagctttcct gaactggaac gtcgggggca agcatacac acacactcca atccatccat      300
```

```
gcatacacag acacaagaca cacacgctca aaccctgtc cacatataca accatacata      360
cttgcacatg tgtgttcatg                                                 380

<210> SEQ ID NO 17
<211> LENGTH: 1315
<212> TYPE: DNA
<213> ORGANISM: Homo sapiens
<220> FEATURE:
<221> NAME/KEY: CDS
<222> LOCATION: (325)..(1116)
<223> OTHER INFORMATION:

<400> SEQUENCE: 17
ggagtgggcc agaagaccac cgctggcaag gactgggttg gttttggag tagtccctgc       60 tgacgtgaca aaaagatctc tcatatgata ttccgaggta tctttgagga agtctctctt    120
tgaggacctc cctttgagct gatggagaac tgggctcccc acaccctctc tgtccccagc    180
tgagattatg gtggatttgg gctacggccc aggcctgggc tcctgctgc tgacccagcc     240 ccagaggtgt tagcaagagc cgtgtgctat ccaccctccc cgagaccacc cctccgacca    300
ggggcctgga gctggcgcgt gact atg cgg ctt ggg ctg tgt gtg gtg gcc       351
                            Met Arg Leu Gly Leu Cys Val Val Ala
                              1               5 ctg gtt ctg agc tgg acg cac ctc acc atc agc agc cgg ggg atc aag      399
Leu Val Leu Ser Trp Thr His Leu Thr Ile Ser Ser Arg Gly Ile Lys
 10              15                  20                  25 ggg aaa agg cag agg cgg atc agt gcc gag ggg agc cag gcc tgt gcc      447
Gly Lys Arg Gln Arg Arg Ile Ser Ala Glu Gly Ser Gln Ala Cys Ala
             30                  35                  40 aaa ggc tgt gag ctc tgc tct gaa atc aac ggt tgc ctc aag tgc tcg      495
Lys Gly Cys Glu Leu Cys Ser Glu Ile Asn Gly Cys Leu Lys Cys Ser
         45                  50                  55 ccc aag ctc ttc att ctg ctg gag agg aac gac atc cgc cag gtg ggc      543
Pro Lys Leu Phe Ile Leu Leu Glu Arg Asn Asp Ile Arg Gln Val Gly
     60                  65                  70 gtc tgc ttg ccg tcc tgc cca cct gga tac ttc gac gcc cgc aac ccc      591
Val Cys Leu Pro Ser Cys Pro Pro Gly Tyr Phe Asp Ala Arg Asn Pro
 75                  80                  85 gac atg aac aag tgc atc aaa tgc aag atc gag cac tgt gag gcc tgc      639
Asp Met Asn Lys Cys Ile Lys Cys Lys Ile Glu His Cys Glu Ala Cys
 90                  95                 100                 105 ttc agc cat aac ttc tgc acc aag tgt aag gag ggc ttg tac ctg cac      687
Phe Ser His Asn Phe Cys Thr Lys Cys Lys Glu Gly Leu Tyr Leu His
                110                 115                 120 aag ggc cgc tgc tat cca gct tgt ccc gag ggc tcc tca gct gcc aat      735
Lys Gly Arg Cys Tyr Pro Ala Cys Pro Glu Gly Ser Ser Ala Ala Asn
            125                 130                 135 ggc acc atg gag tgc agt agt cct gcg caa tgt gaa atg agc gag tgg      783
Gly Thr Met Glu Cys Ser Ser Pro Ala Gln Cys Glu Met Ser Glu Trp
        140                 145                 150 tct ccg tgg ggg ccc tgc tcc aag aag cag cag ctc tgt ggt ttc cgg      831
Ser Pro Trp Gly Pro Cys Ser Lys Lys Gln Gln Leu Cys Gly Phe Arg
    155                 160                 165 agg ggc tcc gag gag cgg aca cgc agg gtg cta cat gcc cct gtg ggg      879
Arg Gly Ser Glu Glu Arg Thr Arg Arg Val Leu His Ala Pro Val Gly
170                 175                 180                 185 gac cat gct gcc tgc tct gac acc aag gag acc cgg agg tgc aca gtg      927
Asp His Ala Ala Cys Ser Asp Thr Lys Glu Thr Arg Arg Cys Thr Val
                190                 195                 200 agg aga gtg ccg tgt cct gag ggg cag aag agg agg aag gga ggc cag      975
```

-continued

```
Arg Arg Val Pro Cys Pro Glu Gly Gln Lys Arg Arg Lys Gly Gly Gln
            205                 210                 215 ggc cgg cgg gag aat gcc aac agg aac ctg gcc agg aag gag agc aag     1023
Gly Arg Arg Glu Asn Ala Asn Arg Asn Leu Ala Arg Lys Glu Ser Lys
            220                 225                 230 gag gcg ggt gct ggc tct cga aga cgc aag ggg cag caa cag cag cag     1071
Glu Ala Gly Ala Gly Ser Arg Arg Lys Gly Gln Gln Gln Gln Gln
        235                 240                 245 cag caa ggg aca gtg ggg cca ctc aca tct gca ggg cct gcc tag         1116
Gln Gln Gly Thr Val Gly Pro Leu Thr Ser Ala Gly Pro Ala
250             255                 260 ggacactgtc cagcctccag gcccatgcag aaagagttca gtgctactct gcgtgattca   1176
agctttcctg aactggaacg tcgggggcaa agcatacaca cacactccaa tccatccatg   1236
catacacaga cacaagacac acacgctcaa accccgtgtcc acatatacaa ccatacatac  1296
ttgcacatgt gtgttcatg                                                1315
```

<210> SEQ ID NO 18
<211> LENGTH: 263
<212> TYPE: PRT
<213> ORGANISM: Homo sapiens

<400> SEQUENCE: 18

```
Met Arg Leu Gly Leu Cys Val Val Ala Leu Val Leu Ser Trp Thr His
1               5                   10                  15

Leu Thr Ile Ser Ser Arg Gly Ile Lys Gly Lys Arg Gln Arg Arg Ile
            20                  25                  30

Ser Ala Glu Gly Ser Gln Ala Cys Ala Lys Gly Cys Glu Leu Cys Ser
        35                  40                  45

Glu Ile Asn Gly Cys Leu Lys Cys Ser Pro Lys Leu Phe Ile Leu Leu
    50                  55                  60

Glu Arg Asn Asp Ile Arg Gln Val Gly Val Cys Leu Pro Ser Cys Pro
65                  70                  75                  80

Pro Gly Tyr Phe Asp Ala Arg Asn Pro Asp Met Asn Lys Cys Ile Lys
                85                  90                  95

Cys Lys Ile Glu His Cys Glu Ala Cys Phe Ser His Asn Phe Cys Thr
            100                 105                 110

Lys Cys Lys Glu Gly Leu Tyr Leu His Lys Gly Arg Cys Tyr Pro Ala
        115                 120                 125

Cys Pro Glu Gly Ser Ser Ala Ala Asn Gly Thr Met Glu Cys Ser Ser
    130                 135                 140

Pro Ala Gln Cys Glu Met Ser Glu Trp Ser Pro Trp Gly Pro Cys Ser
145                 150                 155                 160

Lys Lys Gln Gln Leu Cys Gly Phe Arg Arg Gly Ser Glu Glu Arg Thr
                165                 170                 175

Arg Arg Val Leu His Ala Pro Val Gly Asp His Ala Ala Cys Ser Asp
            180                 185                 190

Thr Lys Glu Thr Arg Arg Cys Thr Val Arg Arg Val Pro Cys Pro Glu
        195                 200                 205

Gly Gln Lys Arg Arg Lys Gly Gly Gln Gly Arg Glu Asn Ala Asn
    210                 215                 220

Arg Asn Leu Ala Arg Lys Glu Ser Lys Glu Ala Gly Ala Gly Ser Arg
225                 230                 235                 240

Arg Arg Lys Gly Gln Gln Gln Gln Gln Gln Gly Thr Val Gly Pro
                245                 250                 255
```

```
Leu Thr Ser Ala Gly Pro Ala
            260

<210> SEQ ID NO 19
<211> LENGTH: 792
<212> TYPE: DNA
<213> ORGANISM: Homo sapiens

<400> SEQUENCE: 19
atgcggcttg ggctgtgtgt ggtggccctg gttctgagct ggacgcacct caccatcagc      60
agccggggga tcaaggggaa aaggcagagg cggatcagtg ccgaggggag ccaggcctgt     120
gccaaaggct gtgagctctg ctctgaaatc aacggttgcc tcaagtgctc gcccaagctc     180
ttcattctgc tggagaggaa cgacatccgc caggtgggcg tctgcttgcc gtcctgccca     240
cctggatact cgacgcccg caaccccgac atgaacaagt gcatcaaatg caagatcgag      300
cactgtgagg cctgcttcag ccataacttc tgcaccaagt gtaaggaggg cttgtacctg     360
cacaagggcc gctgctatcc agcttgtccc gagggctcct cagctgccaa tggcaccatg     420
gagtgcagta gtcctgcgca atgtgaaatg agcgagtggt ctccgtgggg gccctgctcc     480
aagaagcagc agctctgtgg tttccggagg ggctccgagg agcggacacg cagggtgcta     540 catgccctg tggggaccg tgctgcctgc tctgacacca aggagaccg gaggtgcaca       600 gtgaggagag tgccgtgtcc tgaggggcag aagaggagga agggaggcca gggccggcgg     660
gagaatgcca acaggaacct ggccaggaag gagagcaagg aggcgggtgc tggctctcga     720
agacgcaagg ggcagcaaca gcagcagcag caagggacag tggggccact cacatctgca     780
gggcctgcct ag                                                         792

<210> SEQ ID NO 20
<211> LENGTH: 20
<212> TYPE: PRT
<213> ORGANISM: Homo sapiens

<400> SEQUENCE: 20

Met Arg Leu Gly Leu Cys Val Val Ala Leu Val Leu Ser Trp Thr His
1               5                   10                  15

Leu Thr Ile Ser
            20

<210> SEQ ID NO 21
<211> LENGTH: 243
<212> TYPE: PRT
<213> ORGANISM: Homo sapiens

<400> SEQUENCE: 21

Ser Arg Gly Ile Lys Gly Lys Arg Gln Arg Arg Ile Ser Ala Glu Gly
1               5                   10                  15

Ser Gln Ala Cys Ala Lys Gly Cys Glu Leu Cys Ser Glu Ile Asn Gly
            20                  25                  30

Cys Leu Lys Cys Ser Pro Lys Leu Phe Ile Leu Leu Glu Arg Asn Asp
        35                  40                  45

Ile Arg Gln Val Gly Val Cys Leu Pro Ser Cys Pro Pro Gly Tyr Phe
    50                  55                  60

Asp Ala Arg Asn Pro Asp Met Asn Lys Cys Ile Lys Cys Lys Ile Glu
65                  70                  75                  80

His Cys Glu Ala Cys Phe Ser His Asn Phe Cys Thr Lys Cys Lys Glu
                85                  90                  95
```

-continued

```
Gly Leu Tyr Leu His Lys Gly Arg Cys Tyr Pro Ala Cys Pro Glu Gly
            100                 105                 110

Ser Ser Ala Ala Asn Gly Thr Met Glu Cys Ser Ser Pro Ala Gln Cys
        115                 120                 125

Glu Met Ser Glu Trp Ser Pro Trp Gly Pro Cys Ser Lys Lys Gln Gln
    130                 135                 140

Leu Cys Gly Phe Arg Arg Gly Ser Glu Arg Thr Arg Arg Val Leu
145                 150                 155                 160

His Ala Pro Val Gly Asp His Ala Ala Cys Ser Asp Thr Lys Glu Thr
                165                 170                 175

Arg Arg Cys Thr Val Arg Arg Val Pro Cys Pro Glu Gly Gln Lys Arg
            180                 185                 190

Arg Lys Gly Gly Gln Gly Arg Arg Glu Asn Ala Asn Arg Asn Leu Ala
        195                 200                 205

Arg Lys Glu Ser Lys Glu Ala Gly Ala Gly Ser Arg Arg Arg Lys Gly
    210                 215                 220

Gln Gln Gln Gln Gln Gln Gly Thr Val Gly Pro Leu Thr Ser Ala
225                 230                 235                 240

Gly Pro Ala

<210> SEQ ID NO 22
<211> LENGTH: 28
<212> TYPE: PRT
<213> ORGANISM: Homo sapiens

<400> SEQUENCE: 22

Ser Cys Pro Pro Gly Tyr Phe Asp Ala Arg Asn Pro Asp Met Asn Lys
1               5                   10                  15

Cys Ile Lys Cys Lys Ile Glu His Cys Glu Ala Cys
            20                  25

<210> SEQ ID NO 23
<211> LENGTH: 272
<212> TYPE: PRT
<213> ORGANISM: Homo sapiens

<400> SEQUENCE: 23

Met His Leu Arg Leu Ile Ser Trp Leu Phe Ile Ile Leu Asn Phe Met
1               5                   10                  15

Glu Tyr Ile Gly Ser Gln Asn Ala Ser Arg Gly Arg Arg Gln Arg Arg
            20                  25                  30

Met His Pro Asn Val Ser Gln Gly Cys Gln Gly Gly Cys Ala Thr Cys
        35                  40                  45

Ser Asp Tyr Asn Gly Cys Leu Ser Cys Lys Pro Arg Leu Phe Phe Ala
    50                  55                  60

Leu Glu Arg Ile Gly Met Lys Gln Ile Gly Val Cys Leu Ser Ser Cys
65                  70                  75                  80

Pro Ser Gly Tyr Tyr Gly Thr Arg Tyr Pro Asp Ile Asn Lys Cys Thr
                85                  90                  95

Lys Cys Lys Ala Asp Cys Asp Thr Cys Phe Asn Lys Asn Phe Cys Thr
            100                 105                 110

Lys Cys Lys Ser Gly Phe Tyr Leu His Leu Gly Lys Cys Leu Asp Asn
        115                 120                 125

Cys Pro Glu Gly Leu Glu Ala Asn Asn His Thr Met Glu Cys Val Ser
    130                 135                 140

Ile Val His Cys Glu Val Ser Glu Trp Asn Pro Trp Ser Pro Cys Thr
```

```
                145                 150                 155                 160
Lys Lys Gly Lys Thr Cys Gly Phe Lys Arg Gly Thr Glu Thr Arg Val
                    165                 170                 175

Arg Glu Ile Ile Gln His Pro Ser Ala Lys Gly Asn Leu Cys Pro Pro
                180                 185                 190

Thr Asn Glu Thr Arg Lys Cys Thr Val Gln Arg Lys Cys Gln Lys
            195                 200                 205

Gly Glu Arg Gly Lys Gly Arg Glu Arg Lys Arg Lys Lys Pro Asn
        210                 215                 220

Lys Gly Glu Ser Lys Glu Ala Ile Pro Asp Ser Lys Ser Leu Glu Ser
225                 230                 235                 240

Ser Lys Glu Ile Pro Glu Gln Arg Glu Asn Lys Gln Gln Lys Lys
            245                 250                 255

Arg Lys Val Gln Asp Lys Gln Lys Ser Val Ser Val Ser Thr Val His
                260                 265                 270

<210> SEQ ID NO 24
<211> LENGTH: 265
<212> TYPE: PRT
<213> ORGANISM: Mus musculus

<400> SEQUENCE: 24

Met Arg Leu Gly Leu Cys Val Val Ala Leu Val Leu Ser Trp Thr His
1               5                   10                  15

Ile Ala Val Gly Ser Arg Gly Ile Lys Gly Lys Arg Gln Arg Arg Ile
                20                  25                  30

Ser Ala Glu Gly Ser Gln Ala Cys Ala Lys Gly Cys Glu Leu Cys Ser
            35                  40                  45

Glu Val Asn Gly Cys Leu Lys Cys Ser Pro Lys Leu Phe Ile Leu Leu
        50                  55                  60

Glu Arg Asn Asp Ile Arg Gln Val Gly Val Cys Leu Pro Ser Cys Pro
65                  70                  75                  80

Pro Gly Tyr Phe Asp Ala Arg Asn Pro Asp Met Asn Lys Cys Ile Lys
                85                  90                  95

Cys Lys Ile Glu His Cys Glu Ala Cys Phe Ser His Asn Phe Cys Thr
                100                 105                 110

Lys Cys Gln Glu Ala Leu Tyr Leu His Lys Gly Arg Cys Tyr Pro Ala
            115                 120                 125

Cys Pro Glu Gly Ser Thr Ala Ala Asn Ser Thr Met Glu Cys Gly Ser
        130                 135                 140

Pro Ala Gln Cys Glu Met Ser Glu Trp Ser Pro Trp Gly Pro Cys Ser
145                 150                 155                 160

Lys Lys Arg Lys Leu Cys Gly Phe Arg Lys Gly Ser Glu Glu Arg Thr
                165                 170                 175

Arg Arg Val Leu His Ala Pro Gly Gly Asp His Thr Thr Cys Ser Asp
                180                 185                 190

Thr Lys Glu Thr Arg Lys Cys Thr Val Arg Arg Thr Pro Cys Pro Glu
            195                 200                 205

Gly Gln Lys Arg Arg Lys Gly Gly Gln Gly Arg Arg Glu Asn Ala Asn
        210                 215                 220

Arg His Pro Ala Arg Lys Asn Ser Lys Glu Pro Arg Ser Asn Ser Arg
225                 230                 235                 240

Arg His Lys Gly Gln Gln Gln Pro Gln Pro Gly Thr Thr Gly Pro Leu
                245                 250                 255
```

-continued

Thr Ser Val Gly Pro Thr Trp Ala Gln
        260                 265

<210> SEQ ID NO 25
<211> LENGTH: 292
<212> TYPE: PRT
<213> ORGANISM: Homo sapiens

<400> SEQUENCE: 25

Met His Leu Arg Leu Ile Ser Trp Leu Phe Ile Ile Leu Asn Phe Met
1               5                   10                  15

Glu Tyr Ile Gly Ser Gln Asn Ala Ser Arg Gly Arg Arg Gln Arg Arg
            20                  25                  30

Met His Pro Asn Val Ser Gln Gly Cys Gln Gly Gly Cys Ala Thr Cys
        35                  40                  45

Ser Asp Tyr Asn Gly Cys Leu Ser Cys Lys Pro Arg Leu Phe Phe Ala
    50                  55                  60

Leu Glu Arg Ile Gly Met Lys Gln Ile Gly Val Cys Leu Ser Ser Cys
65              70                  75                  80

Pro Ser Gly Tyr Tyr Gly Thr Arg Tyr Pro Asp Ile Asn Lys Cys Thr
            85                  90                  95

Lys Cys Lys Ala Asp Cys Asp Thr Cys Phe Asn Lys Asn Phe Cys Thr
        100                 105                 110

Lys Cys Lys Ser Gly Phe Tyr Leu His Leu Gly Lys Cys Leu Asp Asn
    115                 120                 125

Cys Pro Glu Gly Leu Glu Ala Asn Asn His Thr Met Glu Cys Val Ser
130                 135                 140

Ile Val His Cys Glu Val Ser Glu Trp Asn Pro Trp Ser Pro Cys Thr
145             150                 155                 160

Lys Lys Gly Lys Thr Cys Gly Phe Lys Arg Gly Thr Glu Thr Arg Val
            165                 170                 175

Arg Glu Ile Ile Gln His Pro Ser Ala Lys Gly Asn Leu Cys Pro Pro
        180                 185                 190

Thr Asn Glu Thr Arg Lys Cys Thr Val Gln Arg Lys Lys Cys Gln Lys
    195                 200                 205

Gly Glu Arg Gly Lys Lys Gly Arg Glu Arg Lys Arg Lys Lys Pro Asn
210                 215                 220

Lys Gly Glu Ser Lys Glu Ala Ile Pro Asp Ser Lys Ser Leu Glu Ser
225             230                 235                 240

Ser Lys Glu Ile Pro Glu Gln Arg Glu Asn Lys Gln Gln Gln Lys Lys
            245                 250                 255

Arg Lys Val Gln Asp Lys Gln Lys Ser Gly Ile Glu Val Thr Leu Ala
        260                 265                 270

Glu Gly Leu Thr Ser Val Ser Gln Arg Thr Gln Pro Thr Pro Cys Arg
    275                 280                 285

Arg Arg Tyr Leu
    290

<210> SEQ ID NO 26
<211> LENGTH: 2339
<212> TYPE: DNA
<213> ORGANISM: Homo sapiens
<220> FEATURE:
<221> NAME/KEY: CDS
<222> LOCATION: (603)..(1394)
<223> OTHER INFORMATION:

<400> SEQUENCE: 26

-continued

```
cgggtcgacg atttcgtcgc gccctcgccc ctcccgggcc tgcccccgtc gcgactggca     60
gcacgaagct gagattgtgg tttcctggtg attcaggtgg gagtgggcca aagatcacc    120 gctggcaagg actggtgttt gtcaactgta aggactcatg aacagatct accagggatt    180 ctcagacctt agtttgagaa atgctgcaat taaaggcaaa tcctatcact ctgagtgatc    240
gctttggtgt cgaggcaatc aaccataaag ataaatgcaa atatggaaat tgcataacag    300
tactcagtat taaggttggt ttttggagta gtccctgctg acgtgacaaa aagatctctc    360
atatgatatt ccgaggtatc tttgaggaag tctctctttg aggacctccc tttgagctga    420
tggagaactg ggctccccac accctctctg tccccagctg agattatggt ggatttgggc    480
tacggcccag gctgggcct cctgctgctg acccagcccc agaggtgtta gcaagagccg    540
tgtgctatcc accctccccg agaccacccc tccgaccagg ggcctggagc tggcgcgtga    600
```

| | | |
|---|---|---|
| ct atg cgg ctt ggg ctg tgt gtg gtg gcc ctg gtt ctg agc tgg acg<br>Met Arg Leu Gly Leu Cys Val Val Ala Leu Val Leu Ser Trp Thr<br>1          5                 10              15 | | 647 |
| cac ctc acc atc agc agc cgg ggg atc aag ggg aaa agg cag agg cgg<br>His Leu Thr Ile Ser Ser Arg Gly Ile Lys Gly Lys Arg Gln Arg Arg<br>               20               25               30 | | 695 |
| atc agt gcc gag ggg agc cag gcc tgt gcc aaa ggc tgt gag ctc tgc<br>Ile Ser Ala Glu Gly Ser Gln Ala Cys Ala Lys Gly Cys Glu Leu Cys<br>         35                 40               45 | | 743 |
| tct gaa gtc aac ggc tgc ctc aag tgc tca ccc aag ctg ttc atc ctg<br>Ser Glu Val Asn Gly Cys Leu Lys Cys Ser Pro Lys Leu Phe Ile Leu<br>50                 55               60 | | 791 |
| ctg gag agg aac gac atc cgc cag gtg ggc gtc tgc ttg ccg tcc tgc<br>Leu Glu Arg Asn Asp Ile Arg Gln Val Gly Val Cys Leu Pro Ser Cys<br>65                 70               75 | | 839 |
| cca cct gga tac ttc gac gcc cgc aac ccc gac atg aac aag tgc atc<br>Pro Pro Gly Tyr Phe Asp Ala Arg Asn Pro Asp Met Asn Lys Cys Ile<br>80               85               90              95 | | 887 |
| aaa tgc aag atc gag cac tgt gag gcc tgc ttc agc cat aac ttc tgc<br>Lys Cys Lys Ile Glu His Cys Glu Ala Cys Phe Ser His Asn Phe Cys<br>         100               105             110 | | 935 |
| acc aag tgt aag gag ggc ttg tac ctg cac aag ggc cgc tgc tat cca<br>Thr Lys Cys Lys Glu Gly Leu Tyr Leu His Lys Gly Arg Cys Tyr Pro<br>         115               120             125 | | 983 |
| gct tgt ccc gag ggc tcc tca gct gcc aat ggc acc atg gag tgc agt<br>Ala Cys Pro Glu Gly Ser Ser Ala Ala Asn Gly Thr Met Glu Cys Ser<br>         130               135             140 | | 1031 |
| agt cct gcg caa tgt gaa atg agc gag tgg tct ccg tgg ggg ccc tgc<br>Ser Pro Ala Gln Cys Glu Met Ser Glu Trp Ser Pro Trp Gly Pro Cys<br>145               150               155 | | 1079 |
| tcc aag aag cag cag ctc tgt ggt ttc cgg agg ggc tcc gag gag cgg<br>Ser Lys Lys Gln Gln Leu Cys Gly Phe Arg Arg Gly Ser Glu Glu Arg<br>160               165              170             175 | | 1127 |
| aca cgc agg gtg cta cat gcc cct gtg ggg gac cat gct gcc tgc tct<br>Thr Arg Arg Val Leu His Ala Pro Val Gly Asp His Ala Ala Cys Ser<br>         180               185             190 | | 1175 |
| gac acc aag gag acc cgg agg tgc aca gtg agg aga gtg ccg tgt cct<br>Asp Thr Lys Glu Thr Arg Arg Cys Thr Val Arg Arg Val Pro Cys Pro<br>         195               200             205 | | 1223 |
| gag ggg cag aag agg agg aag gga ggc cag ggc cgg cgg gag aat gcc<br>Glu Gly Gln Lys Arg Arg Lys Gly Gly Gln Gly Arg Arg Glu Asn Ala<br>         210               215             220 | | 1271 |
| aac agg aac ctg gcc agg aag gag agc aag gag gcg ggt gct ggc tct<br>Asn Arg Asn Leu Ala Arg Lys Glu Ser Lys Glu Ala Gly Ala Gly Ser | | 1319 |

|     |     |     |     |     |     |     |     |     |     |     |     |     |     |     |      |
| --- | --- | --- | --- | --- | --- | --- | --- | --- | --- | --- | --- | --- | --- | --- | ---- |
|     |     | 225 |     |     |     | 230 |     |     |     |     | 235 |     |     |     |      |
| cga | aga | cgc | aag | ggg | cag | caa | cag | cag | cag | cag | caa | ggg | aca | gtg | ggg  | 1367 |
| Arg | Arg | Arg | Lys | Gly | Gln | Gln | Gln | Gln | Gln | Gln | Gln | Gly | Thr | Val | Gly  |
| 240 |     |     |     |     | 245 |     |     |     |     | 250 |     |     |     |     | 255  |

| cca | ctc | aca | tct | gca | ggg | cct | gcc | tag | ggacactgtc cagcctccag | 1414 |
| --- | --- | --- | --- | --- | --- | --- | --- | --- | --- | ---- |
| Pro | Leu | Thr | Ser | Ala | Gly | Pro | Ala |     |     |      |
|     |     |     |     | 260 |     |     |     |     |     |      | gcccatgcag aaagagttca gtgctactct gcgtgattca agctttcctg aactggaacg 1474 tcggggcaa agcatacaca cacactccaa tccatccatg catacacaga cacaagacac 1534 acacgctcaa acccctgtcc acatatacaa ccatacatac ttgcacatgt gtgttcatgt 1594 acacacgcag acacagacac cacacacaca catacacaca cacacacaca cgcacacctg 1654 aggccaccag aagacacttc catccctcgg gcccagcagt acacacttgg tttccagagc 1714 tcccagtgga catgtcagag acaacacttc ccagcatctg agaccaaact gcagaggga 1774 gccttctgga gaagctgctg ggatcggacc agccactgtg gcagatggga gccaagcttg 1834 aggactgctg gtggcctggg aagaaacctt cttcccatcc tgttcagcac tcccagctgt 1894 gtgactttat cgttggagag tattgttacc ttccaggata catatcaggg ttaacctgac 1954 tttgaaaact gcttaaaggt ttatttcaaa ttaaaacaaa aaaatcaacg acagcagtag 2014 acacaggcac cacattcctt tgcagggtgt gagggtttgg cgaggtatgc gtaggagcaa 2074 gaagggacag ggaatttcaa gagaccccaa atagcctgct cagtagaggg tcatgcagac 2134 aaggaagaaa acttaggggc tgctctgacg gtggtaaaca ggctgtctat atccttgtta 2194 ctcagagcat ggcccggcag cagtgttgtc acagggcagc ttgttaggaa tgataatctc 2254 aggtctcatt ccagacctgg agagccatga gtctaaattt taagattcct gatgattggc 2314 atgttaccca aatttgagaa gtgct 2339

<210> SEQ ID NO 27
<211> LENGTH: 263
<212> TYPE: PRT
<213> ORGANISM: Homo sapiens

<400> SEQUENCE: 27

Met Arg Leu Gly Leu Cys Val Val Ala Leu Val Leu Ser Trp Thr His
1               5                   10                  15

Leu Thr Ile Ser Ser Arg Gly Ile Lys Gly Lys Arg Gln Arg Arg Ile
                20                  25                  30

Ser Ala Glu Gly Ser Gln Ala Cys Ala Lys Gly Cys Glu Leu Cys Ser
            35                  40                  45

Glu Val Asn Gly Cys Leu Lys Cys Ser Pro Lys Leu Phe Ile Leu Leu
        50                  55                  60

Glu Arg Asn Asp Ile Arg Gln Val Gly Val Cys Leu Pro Ser Cys Pro
65                  70                  75                  80

Pro Gly Tyr Phe Asp Ala Arg Asn Pro Asp Met Asn Lys Cys Ile Lys
                85                  90                  95

Cys Lys Ile Glu His Cys Glu Ala Cys Phe Ser His Asn Phe Cys Thr
            100                 105                 110

Lys Cys Lys Glu Gly Leu Tyr Leu His Lys Gly Arg Cys Tyr Pro Ala
        115                 120                 125

Cys Pro Glu Gly Ser Ser Ala Ala Asn Gly Thr Met Glu Cys Ser Ser
    130                 135                 140

Pro Ala Gln Cys Glu Met Ser Glu Trp Ser Pro Trp Gly Pro Cys Ser
145                 150                 155                 160

```
-continued

Lys Lys Gln Gln Leu Cys Gly Phe Arg Arg Gly Ser Glu Glu Arg Thr
            165                 170                 175

Arg Arg Val Leu His Ala Pro Val Gly Asp His Ala Ala Cys Ser Asp
            180                 185                 190

Thr Lys Glu Thr Arg Arg Cys Thr Val Arg Arg Val Pro Cys Pro Glu
        195                 200                 205

Gly Gln Lys Arg Arg Lys Gly Gly Gln Gly Arg Arg Glu Asn Ala Asn
        210                 215                 220

Arg Asn Leu Ala Arg Lys Glu Ser Lys Glu Ala Gly Ala Gly Ser Arg
225             230                 235                 240

Arg Arg Lys Gly Gln Gln Gln Gln Gln Gln Gly Thr Val Gly Pro
                245                 250                 255

Leu Thr Ser Ala Gly Pro Ala
            260
```

METHODS AND MATERIALS RELATING TO STEM CELL GROWTH FACTOR-LIKE POLYPEPTIDES AND POLYNUCLEOTIDES

This patent application is a continuation-in-part application of U.S. patent application Ser. No. 10/125,852 filed Apr. 19, 2002 now abandoned, which claims the benefit of provisional U.S. patent application Ser. No. 60/316,368 filed Aug. 30, 2001, which in turn is a continuation-in-part application of U.S. patent application Ser. No. 09/799,451 filed Mar. 5, 2001 now U.S. Pat. No. 6,783,969; and U.S. patent application Ser. No. 60/339,739 filed Dec. 10, 2001; all of which are herein incorporated by reference in their entirety.

1. BACKGROUND

1.1 Technical Field

The present invention provides novel polynucleotides and proteins encoded by such polynucleotides, along with uses for these polynucleotides and proteins, for example in therapeutic, diagnostic and research methods.

1.2 Background Art

Identified polynucleotide and polypeptide sequences have numerous applications in, for example, diagnostics, forensics, gene mapping, identification of mutations responsible for genetic disorders or other traits, to assess biodiversity, and to produce many other types of data and products dependent on DNA and amino acid sequences. Proteins are known to have biological activity, for example, by virtue of their secreted nature in the case of leader sequence cloning, by virtue of their cell or tissue source in the case of PCR-based techniques, or by virtue of structural similarity to other genes of known biological activity. It is to these polypeptides and the polynucleotides encoding them that the present invention is directed. In particular, this invention is directed to novel stem cell growth factor-like polypeptides and polynucleotides.

Stem cells are defined as cells with the capacity for unlimited or prolonged self-renewal that can produce at least one type of highly differentiated descendent. It is believed that between the stem cells and its terminally differentiated progeny there is an intermediate population of committed progenitors with limited capacity and restricted differentiation potential (Watt and Hogan, (2000) Science 287, 1427-1430, incorporated herein by reference). Embryonic stem cell division and differentiation give rise to all the differentiated cells and organs of a multicellular organism. A reserve of stem cells is maintained during the adult life of an organism in order to replenish the terminally differentiated cell populations like hematopoietic cells. It is generally assumed that the adult stem cells are derived from the embryonic stem cells and have only a limited potential for differentiation. Stem cells in general have been extremely difficult to culture and maintain in vitro, let alone directing them on a predetermined differentiation pathway.

However, more recently new research have shown that the adult stem cells do possess much wider potential for differentiation than previously thought It was shown that adult neural stem cells when transplanted in an irradiated host, were able to populate the bone marrow and give rise to myeloid, lymphoid and early hematopoietic cells (Bjornson et al, (1999) Science, 283, 534-537, incorporated herein by reference). Also, for the first time, researchers have been able to culture human embryonic stem cells in vitro. The authors showed that human blastocyst cells can be cultured for a prolonged time and could differentiate into variety of different cell types (Thomson et al, (1998) Science, 282, 1145-1147, incorporated herein by reference). This has opened the doors for using autologous transplantation and organ regeneration for treatment of organ failures and degenerative diseases. Precise interactions of multiple receptors on the stem cells with soluble and stromal cell expressed factors are required for a stem cell to divide and commit to differentiation. It has become apparent that the tissue niches and the microenvironment providing the factors are of the utmost importance. Cytolines like IL-3, IL-6, IL-7, and soluble proteins like and flt-3, erythropoietin, and stem cell factor, all have been shown to act in concert to achieve differentiation down a specific pathway. It is thought precise combinations of growth factors, cytokines, and tissue localization could give rise to different differentiated stem cells populations.

One type of stem cell factor (also know as steel factor, mast cell growth factor and kit ligand) is constitutively produced by endothelial cells and fibroblasts (Broudy, (1997) Blood 90, 1342-1364, incorporated herein by reference). This SCF is expressed during embryonic development along the migratory pathways and in destinations of primordial germ cells and melanocytes, in sites of hemopoiesis (including the yolk sac, fetal liver, and bone marrow), in the gut, and in the central nervous system. This SCF is also required during adult life as has been demonstrated using neutralizing antibodies to SCF or SCF receptor. These antibody treatments lead to pancytopenia and markedly decreased bone morrow cellularity, suggesting that continued production of SCF by marrow endothelial cells sand fibroblasts may be required for normal basal hemopoiesis. Erythroid cell expansion is also reported to be dependent on SCF expression. Spermatogenesis, melanocyte development, gut motility, and response to intestinal helminth infection are also impaired by anti-SCF treatment.

SCF is mapped to human chromosome 12a22-12q24. SCF is expressed as both transmembrane and soluble forms. These forms are generated by alternative splicing that either includes or excludes a proteolytic cleavage site. Both the transmembrane and soluble forms are biologically active. The ratios of soluble to transmembrane forms varies dramatically in various tissues, ranging from 10:1 in brain to 0.4:1 in testis. SCF bind SCF receptor (also called c-kit receptor) on the cell surface. This binging leads to receptor dimerization and intermolecular phosphorylation of tyrosines in the cytoplasmic domain. The tyrosine phosphorylation creates docking sites for SH2 domain containing proteins like phospholipase C-y, phosphatidyl inositol-3-kinase, Syp and jun-activated kinase 2 (JAK2). Activated JAK2 activates signal transducers and activator of transcription (STATs) which leads to cellular migration, proliferation and/or differentiation.

Lack of SCF during embryonic development generally leads to perinatal death. The steel mouse, which lacks only the soluble form of SCF, has defects in mast cell production but not in other lineages suggesting that the transmembrane form of the factor may have roles in stem cell maturation into various other hematopoietic cells. Mice lacking SCF also show subtle neurological defects in learning and memory.

Thus, the stem cell growth factor-like polypeptides and polynucleotides of the invention may be used to induce differentiation of embryonic and adult stem cells to give rise to different cell types including mast cells, melanocytes and primordial germ cells. They may also be used in the treatment of leukemia, hemophilia, and degenerative diseases like Alzheimer's disease. The SCF-like polypeptides and polynucleotides of the invention maybe useful in treating learning and memory disorders. The polynucleotides and polypeptides of the invention may further be utilized to generate new tissues and organs that may aid patients in need of transplanted tissues.

2. SUMMARY OF THE INVENTION

This invention is based on the discovery of novel stem cell growth factor-like polypeptides, novel isolated polynucleotides encoding such polypeptides, including recombinant DNA molecules, cloned genes or degenerate variants thereof, especially naturally occurring variants such as allelic variants, antisense polynucleotide molecules, and antibodies that specifically recognize or more epitopes present on such polypeptides, as well as hybridomas producing such antibodies.

The compositions of the present invention additionally include vectors such as expression vectors containing the polynucleotides of the invention, cells genetically engineered to contain such polynucleotides, and cells genetically engineered to express such polynucleotides.

The compositions of the invention provide isolated polynucleotides that include, but are not limited to, a polynucleotide comprising the nucleotide sequence set forth in SEQ ID NO: 1-2, 4, 8, 10, 12, 14, 16-17, 19, or 26; or a fragment of SEQ ID NO: 1-2, 4, 8, 10, 12, 14, 16-17, 19, or 26; a polynucleotide comprising the full length protein coding sequence of SEQ ID NO: 1-2, 4, 8, 10, 12, 14, 16-17, 19, or 26 (for example, SEQ ID NO: 3, 6, 9, 11, 13, 15, 18, 21, or 27); and a polynucleotide comprising the nucleotide sequence of the mature protein coding sequence of any of SEQ ID NO: 3, 5-7, 9, 11, 13, 15, 18, 20-21, or 27. The polynucleotides of the present invention also include, but are not limited to, a polynucleotide that hybridizes under stringent hybridization conditions to (a) the complement of any of the nucleotide sequences set forth in SEQ ID NO: 1-2, 4, 8, 10, 12, 14, 16-17, 19, or 26; (b) a nucleotide sequence encoding any of SEQ ID NO: 3, 5-7, 9, 11, 13, 15, 18, 20-21, or 27; a polynucleotide which is an allelic variant of any polynucleotides recited above having at least 70% polynucleotide sequence identity to the polynucleotides; a polynucleotide which encodes a species homolog (e.g. orthologs) of any of the peptides recited above; or a polynucleotide that encodes a polypeptide comprising a specific domain or truncation of the polypeptide comprising SEQ ID NO: 3, 5-7, 9, 11, 13, 15, 18, 20-21, or 27.

A collection as used in this application can be a collection of only one polynucleotide. The collection of sequence information or unique identifying information of each sequence can be provided on a nucleic acid array. In one embodiment, segments of sequence information are provided on a nucleic acid array to detect the polynucleotide that contains the segment. The array can be designed to detect full-match or mismatch to the polynucleotide that contains the segment. The collection can also be provided in a computer-readable format.

This invention further provides cloning or expression vectors comprising at least a fragment of the polynucleotides set forth above and host cells or organisms transformed with these expression vectors. Useful vectors include plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

The compositions of the present invention include polypeptides comprising, but not limited to, an isolated polypeptide selected from the group comprising the amino acid sequence of SEQ ID NO: 3, 5-7, 9, 11, 13, 15, 18, 20-21, or 27; or the corresponding full length or mature protein. Polypeptides of the invention also include polypeptides with biological activity that are encoded by (a) any of the polynucleotides having a nucleotide sequence set forth in SEQ ID NO: 1-2, 4, 8, 10, 12, 14, 16-17, 19, or 26; or (b) polynucleotides that hybridize to the complement of the polynucleotides of (a) under stringent hybridization conditions. Biologically or immunologically active variants of any of the protein sequences listed as SEQ ID NO: 3, 5-7, 9, 11, 13, 15, 18, 20-21, or 27 and substantial equivalents thereof that retain biological or immunological activity are also contemplated. The polypeptides of the invention may be wholly or partially chemically synthesized but are preferably produced by recombinant means using the genetically engineered cells (e.g. host cells) of the invention.

The invention also provides compositions comprising a polypeptide of the invention. Pharmaceutical compositions of the invention may comprise a polypeptide of the invention and an acceptable carrier, such as a hydrophilic, e.g., pharmaceutically acceptable, carrier.

The invention also relates to methods for producing a polypeptide of the invention comprising culturing host cells comprising an expression vector containing at least a fragment of a polynucleotide encoding the polypeptide of the invention in a suitable culture medium under conditions permitting expression of the desired polypeptide, and purifying the protein or peptide from the culture or from the host cells. Preferred embodiments include those in which the protein produced by such a process is a mature form of the protein.

Polynucleotides according to the invention have numerous applications in a variety of techniques known to those skilled in the art of molecular biology. These techniques include use as hybridization probes, use as oligomers, or primers, for PCR, use in an array, use in computer-readable media, use for chromosome and gene mapping, use in the recombinant production of protein, and use in generation of antisense DNA or RNA, their chemical analogs and the like. For example, when the expression of an mRNA is largely restricted to a particular cell or tissue type, polynucleotides of the invention can be used as hybridization probes to detect the presence of the particular cell or tissue mRNA in a sample using, e.g., in situ hybridization.

In other exemplary embodiments, the polynucleotides are used in diagnostics as expressed sequence tags for identifying expressed genes or, as well known in the art and exemplified by Vollrath et al., Science 258:52-59 (1992), as expressed sequence tags for physical mapping of the human genome.

The polypeptides according to the invention can be used in a variety of conventional procedures and methods that are currently applied to other proteins. For example, a polypeptide of the invention can be used to generate an antibody that specifically binds the polypeptide. Such antibodies, particularly monoclonal antibodies, are useful for detecting or quantitating the polypeptide in tissue. The polypeptides of the invention can also be used as molecular weight markers, and as a food supplement.

Methods are also provided for preventing, treating, or ameliorating a medical condition which comprises the step of administering to a mammalian subject a therapeutically effective amount of a composition comprising a peptide of the present invention and a pharmaceutically acceptable carrier.

In particular, the stem cell growth factor-like polypeptides and polynucleotides of the invention may be used to induce differentiation of embryonic and adult stem cells to give rise to different cell types. They may also be used in the treatment of diseases, for example, leukemia, hemophilia, and degenerative diseases like Alzheimer's disease. The polynucleotides and polypeptides of the invention may further be utilized to generate new tissues and organs that may aid patients in need of transplanted tissues.

The methods of the invention also provide methods for the treatment of disorders as recited herein which comprise the administration of a therapeutically effective amount of a composition comprising a polynucleotide or polypeptide of the invention and a pharmaceutically acceptable carrier to a mammalian subject exhibiting symptoms or tendencies related to disorders as recited herein. In addition, the invention encompasses methods for treating diseases or disorders as recited herein comprising the step of administering a composition comprising compounds and other substances that modulate the overall activity of the target gene products and a pharmaceutically acceptable carrier. Compounds and other substances can effect such modulation either on the level of target gene/protein expression or target protein activity. Specifically, methods are provided for preventing, treating or ameliorating a medical condition, including viral diseases, which comprises administering to a mammalian subject, including but not limited to humans, a therapeutically effective amount of a composition comprising a polypeptide of the invention or a therapeutically effective amount of a composition comprising a binding partner of (e.g., antibody specifically reactive for) stem cell growth factor-like polypeptides of the invention. The mechanics of the particular condition or pathology will dictate whether the polypeptides of the invention or binding partners (or inhibitors) of these would be beneficial to the individual in need of treatment.

According to this method, polypeptides of the invention can be administered to produce an in vitro or in vivo inhibition of cellular function. A polypeptide of the invention can be administered in vivo alone or as an adjunct to other therapies. Conversely, protein or other active ingredients of the present invention may be included in formulations of a particular agent to minimize side effects of such an agent.

The invention further provides methods for manufacturing medicaments useful in the above-described methods.

The present invention further relates to methods for detecting the presence of the polynucleotides or polypeptides of the invention in a sample (e.g., tissue or sample). Such methods can, for example, be utilized as part of prognostic and diagnostic evaluation of disorders as recited herein and for the identification of subjects exhibiting a predisposition to such conditions.

The invention provides a method for detecting a polypeptide of the invention in a sample comprising contacting the sample with a compound that binds to and forms a complex with the polypeptide under conditions and for a period sufficient to form the complex and detecting formation of the complex, so that if a complex is formed, the polypeptide is detected.

The invention also provides kits comprising polynucleotide probes and/or monoclonal antibodies, and optionally quantitative standards, for carrying out methods of the invention. Furthermore, the invention provides methods for evaluating the efficacy of drugs, and monitoring the progress of patients, involved in clinical trials for the treatment of disorders as recited above.

The invention also provides methods for the identification of compounds that modulate (i.e., increase or decrease) the expression or activity of the polynucleotides and/or polypeptides of the invention. Such methods can be utilized, for example, for the identification of compounds that can ameliorate symptoms of disorders as recited herein. Such methods can include, but are not limited to, assays for identifying compounds and other substances that interact with (e.g., bind to) the polypeptides of the invention.

The invention provides a method for identifying a compound that binds to the polypeptide of the present invention comprising contacting the compound with the polypeptide under conditions and for a time sufficient to form a polypeptide/compound complex and detecting the complex, so that if the polypeptide/compound complex is detected, a compound that binds to the polypeptide is identified.

Also provided is a method for identifying a compound that binds to the polypeptide comprising contacting the compound with the polypeptide in a cell for a time sufficient to form a polypeptide/compound complex wherein the complex drives expression of a reporter gene sequence in the cell and detecting the complex by detecting reporter gene sequence expression so that if the polypeptide/compound complex is detected a compound that binds to the polypeptide is identified.

3. BRIEF DESCRIPTION OF THE DRAWINGS

FIG. 1 shows the BLASTP amino acid sequence alignment between stem cell growth factor-like polypeptide SEQ ID NO: 3 and human clone 1 thrombospondin mRNA SEQ ID NO: 23, indicating that the two sequences share 60% similarity over 232 amino acid residues and 46% identity over the same 232 amino acid residues.

FIG. 2 shows the BLASTP amino acid sequence alignment between stem cell growth factor-like polypeptide SEQ ID NO: 3 and human secreted clone da288_6 SEQ ID NO: 25, indicating that the two sequences share 60% similarity over 232 amino acid residues and 46% identity over the same 232 amino acid residues.

FIG. 3 shows the BLASTP amino acid sequence alignment between stem cell growth factor-like polypeptide SEQ ID NO: 9 and human clone 1 thrombospondin mRNA SEQ ID NO: 23, indicating that the two sequences share 55% similarity over 120 amino acid residues and 44% identity over the same 120 amino acid residues.

FIG. 4 shows the BLASTP amino acid sequence alignment between stem cell growth factor-like polypeptide SEQ ID NO: 9 and human secreted protein clone da288_6 SEQ ID NO: 25, indicating that the two sequences share 55% similarity over 120 amino acid residues and 44% identity over the same 120 amino acid residues in the first High Scoring Pair (HSP).

FIG. 5 shows the BLASTP amino acid sequence alignment between stem cell growth factor-like polypeptide SEQ ID NO: 13 and human clone 1 thrombospondin mRNA SEQ ID NO: 23, indicating that the two sequences share 62% similarity over 262 amino acid residues and 46% identity over the same 226 amino acid residues.

FIG. 6 shows the BLASTP amino acid sequence alignment between stem cell growth factor-like polypeptide SEQ ID NO: 3 and human secreted protein clone da288_6 SEQ ID NO: 25, indicating that the two sequences share 62% similarity over 226 amino acid residues and 46% identity over the same 226 amino acid residues.

FIG. 7 shows the BLASTP amino acid sequence alignment between stem cell growth factor-like polypeptide SEQ ID NO: 18 and mouse thrombospondin type 1 domain SEQ ID NO: 24, indicating that the two sequences share 92% similarity over 262 amino acid residues and 88% identity over the same 262 amino acid residues.

FIG. 8 shows the BLASTP amino acid sequence alignment between stem cell growth factor-like polypeptide SEQ ID NO: 18 and human clone 1 thrombospondin mRNA SEQ ID NO: 23, indicating that the two sequences share 63% similarity over 242 amino acid residues and 46% identity over the same 242 amino acid residues.

FIG. 9 shows the BLASTP amino acid sequence alignment between stem cell growth factor-like polypeptide SEQ ID NO: 18 and human secreted protein clone da288_6 SEQ ID NO: 25, indicating that the two sequences share 63% similarity over 242 amino acid residues and 46% identity over the same 242 amino acid residues.

4. DETAILED DESCRIPTION OF THE INVENTION

FIG. 1 shows the BLASTP amino acid sequence alignment between stem cell growth factor-like polypeptide SEQ ID NO: 3 and human clone 1 thrombospondin mRNA SEQ ID NO: 23, indicating that the two sequences share 60% similarity over 232 amino acid residues and 46% identity over the same 232 amino acid residues, wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine. Gaps are presented as dashes.

FIG. 2 shows the BLASTP amino acid sequence alignment between stem cell growth factor-like polypeptide SEQ ID NO: 3 and human secreted clone da288_6 SEQ ID NO: 25, indicating that the two sequences share 60% similarity over 232 amino acid residues and 46% identity over the same 232 amino acid residues, wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine. Gaps are presented as dashes.

FIG. 3 shows the BLASTP amino acid sequence alignment between stem cell growth factor-like polypeptide SEQ ID NO: 9 and human clone 1 thrombospondin mRNA SEQ ID NO: 23, indicating that the two sequences share 55% similarity over 120 amino acid residues and 44% identity over the same 120 amino acid residues, wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine. Gaps are presented as dashes.

FIG. 4 shows the BLASTP amino acid sequence alignment between stem cell growth factor-like polypeptide SEQ ID NO: 9 and human secreted protein clone da288_6 SEQ ID NO: 25, indicating that the two sequences share 55% similarity over 120 amino acid residues and 44% identity over the same 120 amino acid residues in the first high scoring pair, wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine. Gaps are presented as dashes.

FIG. 5 shows the BLASTP amino acid sequence alignment between stem cell growth factor-like polypeptide SEQ ID NO: 13 and human clone 1 thrombospondin mRNA SEQ ID NO: 23, indicating that the two sequences share 62% similarity over 226 amino acid residues and 46% identity over the same 226 amino acid residues, wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine. Gaps are presented as dashes.

FIG. 6 shows the BLASTP amino acid sequence alignment between stem cell growth factor-like polypeptide SEQ ID NO: 3 and human secreted protein clone da288_6 SEQ ID NO: 25, indicating that the two sequences share 62% similarity over 226 amino acid residues and 46% identity over the same 226 amino acid residues, wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine. Gaps are presented as dashes.

FIG. 7 shows the BLASTP amino acid sequence alignment between stem cell growth factor-like polypeptide SEQ ID NO: 18 and mouse thrombospondin type 1 domain SEQ ID NO: 24, indicating that the two sequences share 92% similarity over 262 amino acid residues and 88% identity over the same 262 amino acid residues, wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine. Gaps are presented as dashes.

FIG. 8 shows the BLASTP amino acid sequence alignment between stem cell growth factor-like polypeptide SEQ ID NO: 18 and human clone 1 thrombospondin mRNA SEQ ID NO: 23, indicating that the two sequences share 63% similarity over 242 amino acid residues and 46% identity over the same 242 amino acid residues, wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine. Gaps are presented as dashes.

FIG. 9 shows the BLASTP amino acid sequence alignment between stem cell growth factor-like polypeptide SEQ ID NO: 18 and human secreted protein clone da288_6 SEQ ID NO: 25, indicating that the two sequences share 63% similarity over 242 amino acid residues and 46% identity over the same 242 amino acid residues, wherein A=Alanine, C=Cysteine, D=Aspartic Acid, E=Glutamic Acid, F=Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W=Tryptophan, Y=Tyrosine. Gaps are presented as dashes.

The stem cell growth factor-like polypeptide of SEQ ID NO: 3 is an approximately 250-amino acid protein with a predicted molecular mass of approximately 28-kDa unglycosylated. The initial methionine starts at position 672 of SEQ ID NO:2 and the putative stop codon begins at positions 1425 of SEQ ID NO:2. Protein database searches with the BLASTP algorithm (Altschul S. F. et al., J. Mol. Evol. 36:290-300 (1993) and Altschul S. F. et al., J. Mol. Biol. 21:403-10 (1990), herein incorporated by reference) indicate that SEQ ID NO: 3 is homologous to human clone 1 thrombospondin in mRNA and human secreted clone da288_6.

The stem cell growth factor-like polypeptide of SEQ ID NO: 9 is an approximately 131-amino acid protein with a predicted molecular mass of approximately 15-kDa unglycosylated. Protein database searches with the BLASTP algorithm (Altschul S. F. et al., J. Mol. Evol. 36:290-300 (1993) and Altschul S. F. et al., J. Mol. Biol. 21:403-10 (1990), herein incorporated by reference) indicate that SEQ ID NO: 9 is homologous human clone 1 thrombospondin mRNA and human secreted clone 288_6.

The stem cell growth factor-like polypeptide of SEQ ID NO: 13 is an approximately 243-amino acid protein with a predicted molecular mass of approximately 27-kDa unglycosylated. Protein database searches with the BLASTP algorithm (Altschul S. F. et al., J. Mol. Evol. 36:290-300 (1993) and Altschul S. et al., J. Mol. Biol. 21:403-10 (1990), herein incorporated by reference) indicate that SEQ ID NO: 13 is homologous to human clone 1 thrombospondin mRNA and human secreted protein clone da 288_6.

The stem cell growth factor-like polypeptide of SEQ ID NO: 18 is an approximately 263-amino acid protein with a predicted molecular mass of approximately 29-kDa unglycosylated. Protein database searches with the BLASTP algorithm (Altschul S. F. et al., J. Mol. Evol. 36:290-300 (1993) and Altschul S. et al., J. Mol. Biol. 21:403-10 (1990), herein incorporated by reference) indicate that SEQ ID NO: 18 is homologous to mouse thrombospondin type 1 domain, human clone 1 thrombospondin mRNA, and secreted protein clone 288_6.

A predicted approximately twenty one-residue signal peptide (SEQ ID NO: 5) is encoded from approximately residue 1 through residue 21 of SEQ ID NO: 3, 9, or 13. A predicted approximately twenty residue signal peptide (SEQ ID NO: 20) is encoded from approximately residue 1 through residue 20 of SEQ ID NO: 18. The extra cellular portion may be useful on its own. It may be confirmed by expression in mammalian cells and sequencing of the cleared product. The signal peptide was predicted using Neural Network SignalP V1.1 program (Nielsen et al, (1997) Int. J. Neur. Syst. 8, 581) (from Center for Biological Sequence Analysis, The Technical University of Denmark). One of skill in the art will recognize that the cleavage site may be different than that predicted by the computer program. SEQ ID NO: 6 is the resulting peptide when the signal is removed from SEQ ID NO: 3. SEQ ID NO: 11 is the resulting peptide when the signal is removed from SEQ ID NO: 9. SEQ ID NO: 15 is the resulting peptide when the signal is removed from SEQ ID NO: 13. SEQ ID NO: 21 is the resulting peptide when the signal is removed from SEQ ID NO: 18.

Thrombospondins are a family of extracellular matrix proteins that are involved in cell-cell and cell-matrix communication (Lawler (200) Curr. Opin. Cell Bio. 12, 634-640). More than five different thrombospondins are known with distinct patterns of tissue distribution. Some tissues like heart, cartilage, and brain express most of the thrombospondin gene products. Thrombospondin-1 is a major constituent of blood platelets. Thrombospondin-1 appears to function at the cell surface to bring together membrane proteins and cytokines and other soluble factors. Membrane proteins that bind thrombospondin-1 include integrins, integrin-associated protein (CD47), CD36, proteoglycans. Transforming growth factor β and platelet-derived growth factor also bind thrombospondin-1.

Thrombospondin-1 is a large protein with many distinct domains. It contains a globular domain at both amino and carboxy terminus, a region o homology with procollagen, and three types of repeated sequence motifs termed thrombospondin (TSP) type 1, type 2, and type 3 repeats. TSP1 repeat has been found in various different proteins including, complement components (C6, C7, C8A etc.) extracellular matrix proteins like ADAMTS, mindin, axonal guidance molecule like F-spondin semaphorins, and also SCO-spondin, and TRAP proteins of *Plasmodium*.

Thrombospondin type 1 (TSP) repeat can activate TGF β in epithelial tissues which is involved in regulation of cell growth, differentiation, adhesion, migration, and death. TSP1 is further involved in protein binding, heparin binging, cell attachment, neurite outgrowth, inhibition of proliferation, inhibition of angiogenesis, and activation of apoptosis. TSP1 domains of *Plasmodium* circumsporozoite (CS) protein and TRAP proteins are implicated in salivary gland invasion by the sporozoite.

TSP1 sequences are characterized by conserved cysteines, closely spaced tryptophans, and a cluster of basic residues. Spatial configuration of TSP1 sequences shows to β-sheet domains which are shown to bind heparin (Kilpelainen et al (200) J. Biol Chem. 275, 13564-13570, incorporated herein by reference). Similar spatial fold has been described for heparin-binding growth associated molecule (HB-GAM). HB-GAM is identical to mitogenic and neurite outgrowth-promoting protein pleitrophin; osteoblast specific factor-1; heparin-binding neurotrophic factor; and heparin affin regulatory peptide. Expression of HB-GAM was shown to be associated with extracellular matrix of axonal tracts and synapses, and also with basement membranes outside of brain and in the cartilage matrix. Recently, N-syndecan has been shown to be receptor for HB-GAM in brain and has been suggested to play roles in regulation o hippocampal long-term potentiation, a form of brain plasticity implicated in memory and learning. Therefore, TSP1 containing proteins may act as growth promoters and may exhibit stem cell factor-like activities.

In addition, thrombospondin, synthesized in bone marrow and deposited within the extracellular matrix, functions as a cytoadhesion molecule for primary pluripotent progenitor cells, as well as for hematopoietic progenitor cells committed to erythroid, granulocytic, and megakaryocytic lineages. Thus thrombospondins may be important in blood cell development (Long and Dixit (1990) Blood 75, 2311-2318, incorporated herein by reference).

Stem cell growth factor-like polypeptides and polynucleotides of the invention may be used to induce differentiation of embryonic and adult stem cells to give rise to different cell types. They may also be used in the treatment of leukemia, hemophilia, and degenerative diseases like Alzheimer's disease. The polynucleotides and polypeptides of the invention may further be utilized to generate new tissues and organs that may aid patients in need of transplanted tissues.

4.1 Definitions

It must be noted that as used herein and in the appended claims, the singular forms "a", "an" and "the" include plural references unless the context clearly dictates otherwise.

The term "active" refers to those forms of the polypeptide that retain the biologic and/or immunologic activities of any naturally occurring polypeptide. According to the invention, the terms "biologically active" or "biological activity" refer to a protein or peptide having structural, regulatory or biochemical functions of a naturally occurring molecule. Likewise "biologically active" or "biological activity" refers to the capability of the natural, recombinant or synthetic stem cell growth factor-like peptide, or any peptide thereof, to induce a specific biological response in appropriate animals or cells and to bind with specific antibodies. The term "stem cell growth factor-like biological activity" refers to biological activity that is similar to the biological activity of a stem cell growth factor-like.

The term "activated cells" as used in this application are those cells which are engaged in extracellular or intracellular membrane trafficking, including the export of secretory or enzymatic molecules as part of a normal or disease process.

The terms "complementary" or "complementarity" refer to the natural binding of polynucleotides by base pairing. For example, the sequence 5'-AGT-3' binds to the complementary sequence 3'-TCA-5'. Complementarity between two single-stranded molecules may be "partial" such that only some of the nucleic acids bind or it may be "complete" such that total complementarity exists between the single stranded molecules. The degree of complementarity between the nucleic acid strands has significant effects on the efficiency and strength of the hybridization between the nucleic acid strands.

The term "embryonic stem cells (ES)" refers to a cell that can give rise to many differentiated cell types in an embryo or an adult, including the germ cells. The term "germ line stem cells (GSCs)" refers to stem cells derived from primordial stem cells that provide a steady and continuous source of germ cells for the production of gametes. The term "primordial germ cells (PGCs)" refers to a small population of cells set aside from other cell lineages particularly from the yolk sac, mesenteries, or gonadal ridges during embryogenesis that have the potential to differentiate into germ cells and other cells. PGCs are the source from which GSCs and ES cells are derived The PGCs, the GSCs and the ES cells are capable of self-renewal. Thus these cells not only populate the germ line and give rise to a plurality of terminally differentiated cells that comprise the adult specialized organs, but are able to regenerate themselves. The term "totipotent" refers to the capability of a cell to differentiate into all of the cell types of an adult organism. The term "pluripotent" refers to the capability of a cell to differentiate into a number of differentiated cell types that are present in an adult organism. A pluripotent cell is restricted in its differentiation capability in comparison to a totipotent cell.

The term "expression modulating fragment," EMF, means a series of nucleotides that modulates the expression of an operably linked ORF or another EMF.

As used herein, a sequence is said to "modulate the expression of an operably linked sequence" when the expression of the sequence is altered by the presence of the EMF. EMFs include, but are not limited to, promoters, and promoter modulating sequences (inducible elements). One class of EMFs is nucleic acid fragments which induce the expression of an operably linked ORF in response to a specific regulatory factor or physiological event.

The terms "nucleotide sequence" or "nucleic acid" or "polynucleotide" or "oligonculeotide" are used interchangeably and refer to a heteropolymer of nucleotides or the sequence of these nucleotides. These phrases also refer to DNA or RNA of genomic or synthetic origin which may be single-stranded or double-stranded and may represent the sense or the antisense strand, to peptide nucleic acid (PNA) or to any DNA-like or RNA-like material. In the sequences, A is adenine, C is cytosine, G is guanine, and T is thymine; while N is A, T, G, or C. It is contemplated that where the polynucleotide is RNA, the T (thymine) in the sequence herein may be replaced with U (uracil). Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene.

The terms "oligonucleotide fragment" or a "polynucleotide fragment", "portion," or "segment" or "probe" or "primer" are used interchangeably and refer to a sequence of nucleotide residues which are at least about 5 nucleotides, more preferably at least about 7 nucleotides, more preferably at least about 9 nucleotides, more preferably at least about 11 nucleotides and most preferably at least about 17 nucleotides. The fragment is preferably less than about 500 nucleotides, preferably less than about 200 nucleotides, more preferably less than about 100 nucleotides, more preferably less than about 50 nucleotides and most preferably less than 30 nucleotides. Preferably the probe is from about 6 nucleotides to about 200 nucleotides, preferably from about 15 to about 50 nucleotides, more preferably from about 17 to 30 nucleotides and most preferably from about 20 to 25 nucleotides. Preferably the fragments can be used in polymerase chain reaction (PCR), various hybridization procedures or microarray procedures to identify or amplify identical or related parts of mRNA or DNA molecules. A fragment or segment may uniquely identify each polynucleotide sequence of the present invention. Preferably the fragment comprises a sequence substantially similar to a portion of SEQ ID NO: 1-2, 4, 8, 10, 12, 14, 16-17, 19, or 26.

Probes may, for example, be used to determine whether specific mRNA molecules are present in a cell or tissue or to isolate similar nucleic acid sequences from chromosomal DNA as described by Walsh et al. (Walsh, P. S. et al., 1992, PCR Methods Appl 1:241-250). They may be labeled by nick translation, Klenow fill-in reaction, PCR, or other methods well known in the art. Probes of the present invention, their preparation and/or labeling are elaborated in Sambrook, J. et al., 1989, Molecular Cloning: A Laboratory Manual, Cold Spring Harbor Laboratory, NY; or Ausubel, F. M. et al., 1989, Current Protocols in Molecular Biology, John Wiley & Sons, New York N.Y., both of which are incorporated herein by reference in their entirety.

The nucleic acid sequences of the present invention also include the sequence information from any of the nucleic acid sequences of SEQ ID NO: 1-2, 4, 8, 10, 12, 14, 16-17, 19, or 26. The sequence information can be a segment of SEQ ID NO: 1-2, 4, 8, 10, 12, 14, 16-17, 19, or 26 that uniquely identifies or represents the sequence information of SEQ ID NO: 1-2, 4, 8, 10, 12, 14, 16-17, 19, or 26. One such segment can be a twenty-mer nucleic acid sequence because the probability that a twenty-mer is fully matched in the human genome is 1 in 300. In the human genome, there are three billion base pairs in one set of chromosomes. Because $4^{20}$ possible twenty-mers exist, there are 300 times more twenty-mers than there are base pairs in a set of human chromosomes. Using the same analysis, the probability for a seventeen-mer to be fully matched in the human genome is approximately 1 in 5. When these segments are used in arrays for expression studies, fifteen-mer segments can be used. The probability that the fifteen-mer is fully matched in the expressed sequences is also approximately one in five because expressed sequences comprise less than approximately 5% of the entire genome sequence.

Similarly, when using sequence information for detecting a single mismatch, a segment can be a twenty-five mer. The probability that the twenty-five mer would appear in a human genome with a single mismatch is calculated by multiplying the probability for a full match $(1 \div 4^{25})$ times the increased probability for mismatch at each nucleotide position ($3 \times 25$). The probability that an eighteen mer with a single mismatch can be detected in an array for expression studies is approximately one in five. The probability that a twenty-mer with a single mismatch can be detected in a human genome is approximately one in five.

The term "open reading frame," ORF, means a series of nucleotide triplets coding for amino acids without any termination codons and is a sequence translatable into protein.

The terms "operably linked" or "operably associated" refer to functionally related nucleic acid sequences. For example, a promoter is operably associated or operably linked with a coding sequence if the promoter controls the transcription of the coding sequence. While operably linked nucleic acid sequences can be contiguous and in the same reading frame, certain genetic elements e.g. repressor genes are not contiguously linked to the coding sequence but still control transcription/translation of the coding sequence.

The term "pluripotent" refers to the capability of a cell to differentiate into a number of differentiated cell types that are present in an adult organism. A pluripotent cell is restricted in its differentiation capability in comparison to a totipotent cell.

The terms "polypeptide" or "peptide" or "amino acid sequence" refer to an oligopeptide, peptide, polypeptide or protein sequence or fragment thereof and to naturally occurring or synthetic molecules. A polypeptide "fragment," "portion," or "segment" is a stretch of amino acid residues of at least about 5 amino acids, preferably at least about 7 amino acids, more preferably at least about 9 amino acids and most preferably at least about 17 or more amino acids. The peptide preferably is not greater than about 200 amino acids, more preferably less than 150 amino acids and most preferably less than 100 amino acids. Preferably the peptide is from about 5 to about 200 amino acids. To be active, any polypeptide must have sufficient length to display biological and/or immunological activity.

The term "naturally occurring polypeptide" refers to polypeptides produced by cells that have not been genetically engineered and specifically contemplates various polypeptides arising from post-translational modifications of the polypeptide including, but not limited to, acetylation, carboxylation, glycosylation, phosphorylation, lipidation and acylation.

The term "translated protein coding portion" means a sequence which encodes for the full length protein which may include any leader sequence or a processing sequence.

The term "mature protein coding sequence" refers to a sequence which encodes a peptide or protein without any leader/signal sequence. The "mature protein portion" refers to that portion of the protein without the leader/signal sequence. The peptide may have the leader sequences removed during processing in the cell or the protein may have been produced synthetically or using a polynucleotide only encoding for the mature protein coding sequence. It is contemplated that the mature protein portion may or may not include an initial methionine residue. The initial methionine is often removed during processing of the peptide.

The term "derivative" refers to polypeptides chemically modified by such techniques as ubiquitination, labeling (e.g., with radionuclides or various enzymes), covalent polymer attachment such as pegylation (derivatization with polyethylene glycol) and insertion or substitution by chemical synthesis of amino acids such as ornithine, which do not normally occur in human proteins.

The term "variant" (or "analog") refers to any polypeptide differing from naturally occurring polypeptides by amino acid insertions, deletions, and substitutions, created using, e.g., recombinant DNA techniques. Guidance in determining which amino acid residues may be replaced, added or deleted without abolishing activities of interest, may be found by comparing the sequence of the particular polypeptide with that of homologous peptides and minimizing the number of amino acid sequence changes made in regions of high homology (conserved regions) or by replacing amino acids with consensus sequence.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

Preferably, amino acid "substitutions" are the result of replacing one amino acid with another amino acid having similar structural and/or chemical properties, i.e., conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are preferably in the range of about 1 to 20 amino acids, more preferably 1 to 10 amino acids. The variation allowed may be experimentally determined by systematically making insertions, deletions, or substitutions of amino acids in a polypeptide molecule using recombinant DNA techniques and assaying the resulting recombinant variants for activity.

Alternatively, where alteration of function is desired, insertions, deletions or non-conservative alterations can be engineered to produce altered polypeptides. Such alterations can, for example, alter one or more of the biological functions or biochemical characteristics of the polypeptides of the invention. For example, such alterations may change polypeptide characteristics such as ligand-binding affinities, interchain affinities, or degradation/turnover rate. Further, such alterations can be selected so as to generate polypeptides that are better suited for expression, scale up and the like in the host cells chosen for expression. For example, cysteine residues can be deleted or substituted with another amino acid residue in order to eliminate disulfide bridges.

The terms "purified" or "substantially purified" as used herein denotes that the indicated nucleic acid or polypeptide is present in the substantial absence of other biological macromolecules, e.g., polynucleotides, proteins, and the like. In one embodiment, the polynucleotide or polypeptide is purified such that it constitutes at least 95% by weight, more preferably at least 99% by weight, of the indicated biological macromolecules present (but water, buffers, and other small molecules, especially molecules having a molecular weight of less than 1000 daltons, can be present).

The term "isolated" as used herein refers to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other components normally present in a solution of the same. The terms "isolated" and "purified" do not encompass nucleic acids or polypeptides present in their natural source.

The term "recombinant," when used herein to refer to a polypeptide or protein, means that a polypeptide or protein is derived from recombinant (e.g., microbial, insect, or mammalian) expression systems. "Microbial" refers to recombinant polypeptides or proteins made in bacterial or fungal (e.g., yeast) expression systems. As a product, "recombinant microbial" defines a polypeptide or protein essentially free of native endogenous substances and unaccompanied by associated native glycosylation. Polypeptides or proteins expressed in most bacterial cultures, e.g., *E. coli*, will be free of glycosylation modifications; polypeptides or proteins expressed in yeast will have a glycosylation pattern in general different from those expressed in mammalian cells.

The term "recombinant expression vehicle or vector" refers to a plasmid or phage or virus or vector, for expressing a polypeptide from a DNA (RNA) sequence. An expression vehicle can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an amino terminal methionine residue. This residue may or may not be subsequently cleaved from the expressed recombinant protein to provide a final product.

The term "recombinant expression system" means host cells which have stably integrated a recombinant transcriptional unit into chromosomal DNA or carry the recombinant transcriptional unit extrachromosomally. Recombinant expression systems as defined herein will express heterologous polypeptides or proteins upon induction of the regulatory elements linked to the DNA segment or synthetic gene to be expressed. This term also means host cells which have stably integrated a recombinant genetic element or elements having a regulatory role in gene expression, for example, promoters or enhancers. Recombinant expression systems as defined herein will express polypeptides or proteins endogenous to the cell upon induction of the regulatory elements linked to the endogenous DNA segment or gene to be expressed. The cells can be prokaryotic or eukaryotic.

The term "secreted" includes a protein that is transported across or through a membrane, including transport as a result of signal sequences in its amino acid sequence when it is expressed in a suitable host cell. "Secreted" proteins include without limitation proteins secreted wholly (e.g., soluble proteins) or partially (e.g., receptors) from the cell in which they are expressed. "Secreted" proteins also include without limitation proteins that are transported across the membrane of the endoplasmic reticulum. "Secreted" proteins are also intended to include proteins containing non-typical signal sequences (e.g. Interleukin-1 Beta, see Krasney, P. A. and Young, P. R. (1992) Cytokine 4(2):134-143) and factors released from damaged cells (e.g. Interleukin-1 Receptor Antagonist, see Arend, W. P. et. al. (1998) Annu. Rev. Immunol. 16:27-55)

Where desired, an expression vector may be designed to contain a "signal or leader sequence" which will direct the polypeptide through the membrane of a cell. Such a sequence may be naturally present on the polypeptides of the present invention or provided from heterologous protein sources by recombinant DNA techniques.

The term "stringent" is used to refer to conditions that are commonly understood in the art as stringent. Stringent conditions can include highly stringent conditions (i.e., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C.), and moderately stringent conditions (i.e., washing in 0.2×SSC/0.1% SDS at 42° C.). Other exemplary hybridization conditions are described herein in the examples.

In instances of hybridization of deoxyoligonucleotides, additional exemplary stringent hybridization conditions include washing in 6×SSC/0.05% sodium pyrophosphate at 37° C. (for 14-base oligonucleotides), 48° C. (for 17-base oligonucleotides), 55° C. (for 20-base oligonucleotides), and 60° C. (for 23-base oligonucleotides).

As used herein, "substantially equivalent" can refer both to nucleotide and amino acid sequences, for example a mutant sequence, that varies from a reference sequence by one or more substitutions, deletions, or additions, the net effect of which does not result in an adverse functional dissimilarity between the reference and subject sequences. Typically, such a substantially equivalent sequence varies from one of those listed herein by no more than about 35% (i.e., the number of individual residue substitutions, additions, and/or deletions in a substantially equivalent sequence, as compared to the corresponding reference sequence, divided by the total number of residues in the substantially equivalent sequence is about 0.35 or less). Such a sequence is said to have 65% sequence identity to the listed sequence. In one embodiment, a substantially equivalent, e.g., mutant, sequence of the invention varies from a listed sequence by no more than 30% (70% sequence identity); in a variation of this embodiment, by no more than 25% (75% sequence identity); and in a further variation of this embodiment, by no more than 20% (80% sequence identity) and in a further variation of this embodiment, by no more than 10% (90% sequence identity) and in a further variation of this embodiment, by no more that 5% (95% sequence identity). Substantially equivalent, e.g., mutant, amino acid sequences according to the invention preferably have at least 80% sequence identity with a listed amino acid sequence, more preferably at least 90% sequence identity. Substantially equivalent nucleotide sequence of the invention can have lower percent sequence identities, taking into account, for example, the redundancy or degeneracy of the genetic code. Preferably, nucleotide sequence has at least about 65% identity, more preferably at least about 75% identity, and most preferably at least about 95% identity. For the purposes of the present invention, sequences having substantially equivalent biological activity and substantially equivalent expression characteristics are considered substantially equivalent. For the purposes of determining equivalence, truncation of the mature sequence (e.g., via a mutation which creates a spurious stop codon) should be disregarded. Sequence identity may be determined, e.g., using the Jotun Hein method (Hein, J. (1990) Methods Enzymol. 183:626-645). Identity between sequences can also be determined by other methods known in the art, e.g. by varying hybridization conditions.

The term "totipotent" refers to the capability of a cell to differentiate into all of the cell types of an adult organism.

The term "transformation" means introducing DNA into a suitable host cell so that the DNA is replicable, either as an extrachromosomal element, or by chromosomal integration. The term "transfection" refers to the taking up of an expression vector by a suitable host cell, whether or not any coding sequences are in fact expressed. The term "infection" refers to the introduction of nucleic acids into a suitable host cell by use of a virus or viral vector.

As used herein, an "uptake modulating fragment," UMF, means a series of nucleotides which mediate the uptake of a linked DNA fragment into a cell. UMFs can be readily identified using known UMFs as a target sequence or target motif with the computer-based systems described below. The presence and activity of a UMF can be confirmed by attaching the suspected UMF to a marker sequence. The resulting nucleic acid molecule is then incubated with an appropriate host under appropriate conditions and the uptake of the marker sequence is determined. As described above, a UMF will increase the frequency of uptake of a linked marker sequence.

Each of the above terms is meant to encompass all that is described for each, unless the context dictates otherwise.

4.2 Nucleic Acids of the Invention

The invention is based on the discovery of a novel stem cell growth factor-like polypeptide, the polynucleotides encoding the stem cell growth factor-like polypeptide and the use of these compositions for the diagnosis, treatment or prevention of cancers and other immunological disorders.

The isolated polynucleotides of the invention include, but are not limited to a polynucleotide comprising any of the nucleotide sequences of SEQ ID NO: 1-2, 4, 8, 10, 12, 14, 16-17, 19, or 26; a fragment of SEQ ID NO: 1-2, 4, 8, 10, 12, 14, 16-17, 19, or 26; a polynucleotide comprising the full length protein coding sequence of SEQ ID NO: 1-2, 4, 8, 10, 12, 14, 16-17, 19, or 26 (for example coding for SEQ ID NO: 3, 6, 9, 11, 13, 15, 18, 21, or 27); and a polynucleotide comprising the nucleotide sequence encoding the mature protein coding sequence of the polypeptides of any one of SEQ ID NO: 3, 5-7, 9, 11, 13, 15, 18, 20-21, or 27. The polynucleotides of the present invention also include, but are not limited to, a polynucleotide that hybridizes under stringent conditions to (a) the complement of any of the nucleotides sequences of SEQ ID NO: 1-2, 4, 8, 10, 12, 14, 16-17, 19, or 26; (b) a polynucleotide encoding any one of the polypeptides of SEQ ID NO: 3, 5-7, 9, 11, 13, 15, 18, 20-21, or 27; (c) a polynucleotide which is an allelic variant of any polynucleotides recited above; (d) a polynucleotide which encodes a species homolog of any of the proteins recited above; or (e) a polynucleotide that encodes a polypeptide comprising a specific domain or truncation of the polypeptides of SEQ ID NO: 3, 5-7, 9, 11, 13, 15, 18, 20-21, or 27. Domains of interest may depend on the nature of the encoded polypeptide; e.g., domains in receptor-like polypeptides include ligand-binding, extracellular, transmembrane, or cytoplasmic domains, or combinations thereof; domains in immunoglobulin-like proteins include the variable immunoglobulin-like domains; domains in enzyme-like polypeptides include catalytic and substrate binding domains; and domains in ligand polypeptides include receptor-binding domains.

The polynucleotides of the invention include naturally occurring or wholly or partially synthetic DNA, e.g., cDNA and genomic DNA, and RNA, e.g., mRNA. The polynucleotides may include all of the coding region of the cDNA or may represent a portion of the coding region of the cDNA.

The present invention also provides genes corresponding to the cDNA sequences disclosed herein. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials. Further 5' and 3' sequence can be obtained using methods known in the art. For example, full length cDNA or genomic DNA that corresponds to any of the polynucleotides of SEQ ID NO: 1-2, 4, 8, 10, 12, 14, 16-17, 19, or 26 can be obtained by screening appropriate cDNA or genomic DNA libraries under suitable hybridization conditions using any of the polynucleotides of SEQ ID NO: 1-2, 4, 8, 10, 12, 14, 16-17, 19, or 26 or a portion thereof as a probe. Alternatively, the polynucleotides of SEQ ID NO: 1-2, 4, 8, 10, 12, 14, 16-17, 19, or 26 may be used as the basis for suitable primer(s) that allow identification and/or amplification of genes in appropriate genomic DNA or cDNA libraries.

The nucleic acid sequences of the invention can be assembled from ESTs and sequences (including cDNA and genomic sequences) obtained from one or more public databases, such as dbEST, gbpri, and UniGene. The EST sequences can provide identifying sequence information, representative fragment or segment information, or novel segment information for the full-length gene.

The polynucleotides of the invention also provide polynucleotides including nucleotide sequences that are substantially equivalent to the polynucleotides recited above. Polynucleotides according to the invention can have, e.g., at least about 65%, at least about 70%, at least about 75%, at least about 80%, 81%, 82%, 83%, 84%, 85%, 86%, 87%, 88%, or 89%, more typically at least about 90%, 91%, 92%, 93%, or 94% and even more typically at least about 95%, 96%, 97%, 98% or 99% sequence identity to a polynucleotide recited above.

Included within the scope of the nucleic acid sequences of the invention are nucleic acid sequence fragments that hybridize under stringent conditions to any of the nucleotide sequences of SEQ ID NO: 1-2, 4, 8, 10, 12, 14, 16-17, 19, or 26, or complements thereof, which fragment is greater than about 5 nucleotides, preferably 7 nucleotides, more preferably greater than 9 nucleotides and most preferably greater than 17 nucleotides. Fragments of, e.g. 15, 17, or 20 nucleotides or more that are selective for (i.e. specifically hybridize to any one of the polynucleotides of the invention) are contemplated. Probes capable of specifically hybridizing to a polynucleotide can differentiate polynucleotide sequences of the invention from other polynucleotide sequences in the same family of genes or can differentiate human genes from genes of other species, and are preferably based on unique nucleotide sequences.

The sequences falling within the scope of the present invention are not limited to these specific sequences, but also include allelic and species variations thereof. Allelic and species variations can be routinely determined by comparing the sequence provided in SEQ ID NO: 1-2, 4, 8, 10, 12, 14, 16-17, 19, or 26, a representative fragment thereof, or a nucleotide sequence at least 90% identical, preferably 95% identical, to SEQ ID NO: 1-2, 4, 8, 10, 12, 14, 16, 17, 19, or 26 with a sequence from another isolate of the same species. Furthermore, to accommodate codon variability, the invention includes nucleic acid molecules coding for the same amino acid sequences as do the specific ORFs disclosed herein. In other words, in the coding region of an ORF, substitution of one codon for another codon that encodes the same amino acid is expressly contemplated.

The nearest neighbor result for the nucleic acids of the present invention can be obtained by searching a database using an algorithm or a program. Preferably, a BLAST which stands for Basic Local Alignment Search Tool is used to search for local sequence alignments (Altshul, S. F. J. Mol. Evol. 36 290-300 (1993) and Altschul S. F. et al. J. Mol. Biol. 21:403-410 (1990))

Species homologs (or orthologs) of the disclosed polynucleotides and proteins are also provided by the present invention. Species homologs may be isolated and identified by making suitable probes or primers from the sequences provided herein and screening a suitable nucleic acid source from the desired species.

The invention also encompasses allelic variants of the disclosed polynucleotides or proteins; that is, naturally-occurring alternative forms of the isolated polynucleotide which also encode proteins which are identical, homologous or related to that encoded by the polynucleotides.

The nucleic acid sequences of the invention are further directed to sequences which encode variants of the described nucleic acids. These amino acid sequence variants may be prepared by methods known in the art by introducing appropriate nucleotide changes into a native or variant polynucleotide. There are two variables in the construction of amino acid sequence variants: the location of the mutation and the nature of the mutation. Nucleic acids encoding the amino acid sequence variants are preferably constructed by mutating the polynucleotide to encode an amino acid sequence that does not occur in nature. These nucleic acid alterations can be made at sites that differ in the nucleic acids from different species (variable positions) or in highly conserved regions (constant regions). Sites at such locations will typically be modified in series, e.g., by substituting first with conservative choices (e.g., hydrophobic amino acid to a different hydrophobic amino acid) and then with more distant choices (e.g., hydrophobic amino acid to a charged amino acid), and then deletions or insertions may be made at the target site. Amino acid sequence deletions generally range from about 1 to 30 residues, preferably about 1 to 10 residues, and are typically contiguous. Amino acid insertions include amino- and/or carboxyl-terminal fusions ranging in length from one to one hundred or more residues, as well as intrasequence insertions of single or multiple amino acid residues. Intrasequence insertions may range generally from about 1 to 10 amino residues, preferably from 1 to 5 residues. Examples of terminal insertions include the heterologous signal sequences necessary for secretion or for intracellular targeting in different host cells and sequences such as FLAG or poly-histidine sequences useful for purifying the expressed protein.

In a preferred method, polynucleotides encoding the novel amino acid sequences are changed via site-directed mutagenesis. This method uses oligonucleotide sequences to alter a polynucleotide to encode the desired amino acid variant, as well as sufficient adjacent nucleotides on both sides of the changed amino acid to form a stable duplex on either side of the site being changed. In general, the techniques of site-directed mutagenesis are well known to those of skill in the art and this technique is exemplified by publications such as, Edelman et al., *DNA* 2:183 (1983). A versatile and efficient method for producing site-specific changes in a polynucleotide sequence was published by Zoller and Smith, *Nucleic Acids Res.* 10:6487-6500 (1982). PCR may also be used to create amino acid sequence variants of the novel nucleic acids. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the polypeptide at the position specified by the primer. The product DNA fragments replace the corresponding region in the plasmid and this gives a polynucleotide encoding the desired amino acid variant.

A further technique for generating amino acid variants is the cassette mutagenesis technique described in Wells et al., *Gene* 34:315 (1985); and other mutagenesis techniques well known in the art, such as, for example, the techniques in Sambrook et al., supra, and *Current Protocols in Molecular Biology*, Ausubel et al. Due to the inherent degeneracy of the genetic code, other DNA sequences which encode substantially the same or a functionally equivalent amino acid sequence may be used in the practice of the invention for the cloning and expression of these novel nucleic acids. Such DNA sequences include those which are capable of hybridizing to the appropriate novel nucleic acid sequence under stringent conditions.

Polynucleotides encoding preferred polypeptide truncations of the invention can be used to generate polynucleotides encoding chimeric or fusion proteins comprising one or more domains of the invention and heterologous protein sequences.

The polynucleotides of the invention additionally include the complement of any of the polynucleotides recited above. The polynucleotide can be DNA (genomic, cDNA, amplified, or synthetic) or RNA. Methods and algorithms for obtaining such polynucleotides are well known to those of skill in the art and can include, for example, methods for determining hybridization conditions that can routinely isolate polynucleotides of the desired sequence identities.

In accordance with the invention, polynucleotide sequences comprising the mature protein coding sequences, coding for any one of SEQ ID NO: 3, 5-7, 9, 11, 13, 15, 18, 20-21, or 27; or functional equivalents thereof, may be used to generate recombinant DNA molecules that direct the expression of that nucleic acid, or a functional equivalent thereof, in appropriate host cells. Also included are the cDNA inserts of any of the clones identified herein.

A polynucleotide according to the invention can be joined to any of a variety of other nucleotide sequences by well-established recombinant DNA techniques (see Sambrook J et al. (1989) Molecular Cloning: A Laboratory Manual, Cold Spring Harbor Laboratory, NY). Useful nucleotide sequences for joining to polynucleotides include an assortment of vectors, e.g., plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

The present invention further provides recombinant constructs comprising a nucleic acid having any of the nucleotide sequences of SEQ ID NO: 1-2, 4, 8, 10, 12, 14, 16-17, 19, or 26 or a fragment thereof or any other polynucleotides of the invention. In one embodiment, the recombinant constructs of the present invention comprise a vector, such as a plasmid or viral vector, into which a nucleic acid having any of the nucleotide sequences of SEQ ID NO: 1-2, 4, 8, 10, 12, 14, 16-17, 19, or 26 or a fragment thereof is inserted, in a forward or reverse orientation. In the case of a vector comprising one of the ORFs of the present invention, the vector may further comprise regulatory sequences, including for example, a promoter, operably linked to the ORF. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, PXTI, pSG (Stratagene) pSVK3, pBPV, pMSG, and pSVL (Pharmacia).

The isolated polynucleotide of the invention may be operably linked to an expression control sequence such as the pMT2 or pED expression vectors disclosed in Kaufman et al., *Nucleic Acids Res.* 19, 4485-4490 (1991), in order to produce the protein recombinantly. Many suitable expression control sequences are known in the art. General methods of expressing recombinant proteins are also known and are exemplified in R. Kaufman, *Methods in Enzymology* 185, 537-566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda PR, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an amino terminal identification peptide imparting desired characteristics, e.g., stabilization or simplified purification of expressed recombinant product. Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM 1 (Promega Biotech, Madison, Wis., USA). These pBR322 "backbone" sections are combined with an appropriate promoter and the structural sequence to be expressed. Following transformation of a suitable host strain and growth of the host strain to an appropriate cell density, the selected promoter is induced or derepressed by appropriate means (e.g., temperature shift or chemical induction) and cells are cultured for an additional period. Cells are typically harvested by centrifugation, disrupted by physical or chemical means, and the resulting crude extract retained for further purification.

Polynucleotides of the invention can also be used to induce immune responses. For example, as described in Fan et al., *Nat. Biotech.* 17:870-872 (1999), incorporated herein by reference, nucleic acid sequences encoding a polypeptide may be used to generate antibodies against the encoded polypeptide following topical administration of naked plasmid DNA or following injection, and preferably intramuscular injection of the DNA. The nucleic acid sequences are preferably inserted in a recombinant expression vector and may be in the form of naked DNA.

4.2.1 Antisense Nucleic Acids

Another aspect of the invention pertains to isolated antisense nucleic acid molecules that can hybridize to, or are complementary to, the nucleic acid molecule comprising the stem cell growth factor-like nucleotide sequence, or fragments, analogs or derivatives thereof. An "antisense" nucleic acid comprises a nucleotide sequence that is complementary to a "sense" nucleic acid encoding a protein (e.g., complementary to the coding strand of a double-stranded cDNA molecule or complementary to an mRNA sequence). In specific aspects, antisense nucleic acid molecules are provided that comprise a sequence complementary to at least about 10, 25, 50, 100, 250 or 500 nucleotides or an entire stem cell growth factor-like coding strand, or to only a portion thereof. Nucleic acid molecules encoding fragments, homologs, derivatives and analogs of a stem cell growth factor-like or antisense nucleic acids complementary to a stem cell growth factor-like nucleic acid sequence of are additionally provided.

In one embodiment, an antisense nucleic acid molecule is antisense to a "coding region" of the coding strand of a nucleotide sequence encoding a stem cell growth factor-like protein. The term "coding region" refers to the region of the nucleotide sequence comprising codons which are translated into amino acid residues. In another embodiment, the antisense nucleic acid molecule is antisense to a "conceding region" of the coding strand of a nucleotide sequence encoding the stem cell growth factor-like protein. The term "conceding region" refers to 5' and 3' sequences which flank the coding region that are not translated into amino acids (i.e., also referred to as 5' and 3' untranslated regions).

Given the coding strand sequences encoding the stem cell growth factor-like protein disclosed herein, antisense nucleic acids of the invention can be designed according to the rules of Watson and Crick or Hoogsteen base pairing. The antisense nucleic acid molecule can be complementary to the entire coding region of stem cell growth factor-like mRNA, but more preferably is an oligonucleotide that is antisense to only a portion of the coding or noncoding region of stem cell growth factor-like mRNA. For example, the antisense oligonucleotide can be complementary to the region surrounding the translation start site of stem cell growth factor-like mRNA. An antisense oligonucleotide can be, for example, about 5, 10, 15, 20, 25, 30, 35, 40, 45, or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids (e.g., phosphorothioate derivatives and acridine substituted nucleotides can be used).

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following section).

The antisense nucleic acid molecules of the invention are typically administered to a subject or generated in situ such that they hybridize with or bind to cellular mRNA and/or genomic DNA encoding a stem cell growth factor-like protein to thereby inhibit expression of the protein (e.g., by inhibiting transcription and/or translation). The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface (e.g., by linking the antisense nucleic acid molecules to peptides or antibodies that bind to cell surface receptors or antigens). The antisense nucleic acid molecules can also be delivered to cells using the vectors described herein. To achieve sufficient nucleic acid molecules, vector constructs in which the antisense nucleic acid molecule is placed under the control of a strong pol II or pol III promoter are preferred.

In yet another embodiment, the antisense nucleic acid molecule of the invention is an alpha-anomeric nucleic acid molecule. An alpha-anomeric nucleic acid molecule forms specific double-stranded hybrids with complementary RNA in which, contrary to the usual alpha-units, the strands run parallel to each other. See, e.g., Gaultier, et al., 1987. Nucl. Acids Res. 15: 6625-6641. The antisense nucleic acid molecule can also comprise a 2'-o-methylribonucleotide (see, e.g., Inoue, et al. 1987. Nucl. Acids Res. 15: 6131-6148) or a chimeric RNA-DNA analogue (see, e.g., Inoue, et al., 1987. FEBS Lett. 215: 327-330.

4.2.2 Ribozymes and PNA Moieties

Nucleic acid modifications include, by way of non-limiting example, modified bases, and nucleic acids whose sugar phosphate backbones are modified or derivatized. These modifications are carried out at least in part to enhance the chemical stability of the modified nucleic acid, such that they can be used, for example, as antisense binding nucleic acids in therapeutic applications in a subject.

In one embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes as described in Haselhoff and Gerlach 1988. Nature 334: 585-591) can be used to catalytically cleave stem cell growth factor-like mRNA transcripts to thereby inhibit translation of stem cell growth factor-like mRNA. A ribozyme having specificity for a stem cell growth factor-like-encoding nucleic acid can be designed based upon the nucleotide sequence of a stem cell growth factor-like cDNA disclosed herein. For example, a derivative of a Tetrahymena L-19 IVS RNA can be constructed in which the nucleotide sequence of the active site is complementary to the nucleotide sequence to be cleaved in a stem cell growth factor-like-encoding mRNA. See, e.g., U.S. Pat. No. 4,987,071 to Cech, et al. and U.S. Pat. No. 5,116,742 to Cech, et al. Stem cell growth factor-like mRNA can also be used to select a catalytic RNA having a specific ribonuclease activity from a pool of RNA molecules. See, e.g., Bartel et al., (1993) Science 261:1411-1418.

Alternatively, stem cell growth factor-like gene expression can be inhibited by targeting nucleotide sequences complementary to the regulatory region of the stem cell growth factor-like nucleic acid (e.g., the stem cell growth factor-like promoter and/or enhancers) to form triple helical structures that prevent transcription of the stem cell growth factor-like gene in target cells. See, e.g., Helene, 1991. Anticancer Drug Des. 6: 569-84; Helene, et al. 1992. Ann. N.Y. Acad. Sci. 660: 27-36; Maher, 1992. Bioassays 14: 807-15.

In various embodiments, the stem cell growth factor-like nucleic acids can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids. See, e.g., Hyrup, et al., 1996. Bioorg Med Chem 4: 5-23. As used herein, the terms "peptide nucleic acids" or "PNAs" refer to nucleic acid mimics (e.g., DNA mimics) in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup, et al., 1996. supra; Perry-O'Keefe, et al., 1996. Proc. Natl. Acad. Sci. USA 93: 14670-14675.

PNAs of stem cell growth factor-like can be used in therapeutic and diagnostic applications. For example, PNAs can be used as antisense or antigene agents for sequence-specific modulation of gene expression by, e.g., inducing transcription or translation arrest or inhibiting replication. PNAs of stem cell growth factor-like can also be used, for example, in the analysis of single base pair mutations in a gene (e.g., PNA directed PCR clamping; as artificial restriction enzymes when used in combination with other enzymes, e.g., S1 nucleases (see, Hyrup, et al., 1996. supra); or as probes or primers for DNA sequence and hybridization (see, Hyrup, et al., 1996, supra; Perry-O'Keefe, et al., 1996. supra).

In another embodiment, PNAs of stem cell growth factor-like can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of stem cell growth factor-like can be generated that may combine the advantageous properties of PNA and DNA. Such chimeras allow DNA recognition enzymes (e.g., RNase H and DNA polymerases) to interact with the DNA portion while the PNA portion would provide high binding affinity and specificity. PNA-DNA chimeras can be linked using linkers of appropriate lengths selected in terms of base stacking, number of bonds between the nucleobases, and orientation (see, Hyrup, et al., 1996. supra). The synthesis of PNA-DNA chimeras can be performed as described in Hyrup, et al., 1996. Supra, et al., 1996. Nucl Acids Res 24: 3357-3363. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA. See, e.g., Mag, et al., 1989. Nucl Acid Res 17: 5973-5988. PNA monomers are then coupled in a stepwise manner to produce a chimeric molecule with a 5' PNA segment and a 3' DNA segment. See, e.g., Finn, et al., 1996. supra. Alternatively, chimeric molecules can be synthesized with a 5' DNA segment and a 3' PNA segment. See, e.g., Petersen, et al., 1975. Bioorg. Med. Chem. Lett. 5: 1119-11124.

In other embodiments, the oligonucleotide may include other appended groups such as peptides (e.g., for targeting host cell receptors in vivo), or agents facilitating transport across the cell membrane (see, e.g., Letsinger, et al., 1989. Proc. Natl. Acad. Sci. U.S.A. 86: 6553-6556; Lemaitre, et al., 1987. Proc. Natl. Acad. Sci. 84: 648-652; PCT Publication No. WO88/09810) or the blood-brain barrier (see, e.g., PCT Publication No. WO 89/10134). In addition, oligonucleotides can be modified with hybridization-triggered cleavage agents (see, e.g., Krol, et al., 1988. BioTechniques 6:958-976) or intercalating agents (see, e.g., Zon, 1988. Pharm. Res. 5: 539-549). To this end, the oligonucleotide can be conjugated to another molecule, e.g., a peptide, a hybridization triggered cross-linking agent, a transport agent, a hybridization-triggered cleavage agent, and the like.

4.3 Hosts

The present invention further provides host cells genetically engineered to contain the polynucleotides of the invention. For example, such host cells may contain nucleic acids of the invention introduced into the host cell using known transformation, transfection or infection methods. The present invention still further provides host cells genetically engineered to express the polynucleotides of the invention, wherein such polynucleotides are in operative association with a regulatory sequence heterologous to the host cell which drives expression of the polynucleotides in the cell.

The host cell can be a higher eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected by calcium phosphate transfection, DEAE, dextran mediated transfection, or electroporation (Davis, L. et al., Basic Methods in Molecular Biology (1986)). The host cells containing one of polynucleotides of the invention, can be used in conventional manners to produce the gene product encoded by the isolated fragment (in the case of an ORF) or can be used to produce a heterologous protein under the control of the EMF.

Any host/vector system can be used to express one or more of the ORFs of the present invention. These include, but are not limited to, eukaryotic hosts such as HeLa cells, Cv-1 cell, COS cells, and Sf9 cells, as well as prokaryotic host such as E. coli and B. subtilis. The most preferred cells are those which do not normally express the particular polypeptide or protein or which expresses the polypeptide or protein at low natural level. Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., in Molecular Cloning: A Laboratory Manual, Second Edition, Cold Spring Harbor, N.Y. (1989), the disclosure of which is hereby incorporated by reference.

Various mammalian cell culture systems can also be employed to express recombinant protein. Examples of mammalian expression systems include the COS-7 lines of monkey kidney fibroblasts, described by Gluzinan, Cell 23:175 (1981), and other cell lines capable of expressing a compatible vector, for example, the C127, 3T3, CHO, HeLa and BHK cell tines. Mammalian expression vectors will comprise an origin of replication, a suitable promoter, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Recombinant polypeptides and proteins produced in bacterial culture are usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe, Kluyveromyces strains, Candida*, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

In another embodiment of the present invention, cells and tissues may be engineered to express an endogenous gene comprising the polynucleotides of the invention under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods. Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting, including polyadenylation signals, mRNA stability elements, splice sites, leader sequences for enhancing or modifying transport or secretion properties of the protein, or other sequences which alter or improve the function or stability of protein or RNA molecules.

The targeting event may be a simple insertion of the regulatory sequence, placing the gene under the control of the new regulatory sequence, e.g., inserting a new promoter or enhancer or both upstream of a gene. Alternatively, the targeting event may be a simple deletion of a regulatory element, such as the deletion of a tissue-specific negative regulatory element. Alternatively, the targeting event may replace an existing element; for example, a tissue-specific enhancer can be replaced by an enhancer that has broader or different cell-type specificity than the naturally occurring elements. Here, the naturally occurring sequences are deleted and new sequences are added. In all cases, the identification of the targeting event may be facilitated by the use of one or more selectable marker genes that are contiguous with the targeting DNA, allowing for the selection of cells in which the exogenous DNA has integrated into the host cell genome. The identification of the targeting event may also be facilitated by the use of one or more marker genes exhibiting the property of negative selection, such that the negatively selectable marker is linked to the exogenous DNA, but configured such that the negatively selectable marker flanks the targeting sequence, and such that a correct homologous recombination event with sequences in the host cell genome does not result in the stable integration of the negatively selectable marker. Markers useful for this purpose include the Herpes Simplex Virus thymidine kinase (TK) gene or the bacterial xanthine-guanine phosphoribosyl-transferase (gpt) gene.

The gene targeting or gene activation techniques which can be used in accordance with this aspect of the invention are more particularly described in U.S. Pat. No. 5,272,071 to Chappel; U.S. Pat. No. 5,578,461 to Sherwin et al.; International Application No. PCT/US92/09627 (WO93/09222) by Selden et al.; and International Application No. PCT/US90/06436 (WO91/06667) by Skoultchi et al., each of which is incorporated by reference herein in its entirety.

4.3.1 Chimeric and Fusion Proteins

The invention also provides stem cell growth factor-like chimeric or fusion proteins. As used herein, a stem cell growth factor-like "chimeric protein" or "fusion protein" comprises a stem cell growth factor-like polypeptide operatively-linked to a non-stem cell growth factor-like polypeptide. A "stem cell growth factor-like polypeptide" refers to a polypeptide having an amino acid sequence corresponding to a stem cell growth factor-like protein, whereas a "non-stem cell growth factor-like polypeptide" refers to a polypeptide having an amino acid sequence corresponding to a protein that is not substantially homologous to the stem cell growth factor-like protein, e.g., a protein that is different from the stem cell growth factor-like protein and that is derived from the same or a different organism. Within a stem cell growth factor-like fusion protein the stem cell growth factor-like polypeptide can correspond to all or a portion of a stem cell growth factor-like protein. In one embodiment, a stem cell growth factor-like fusion protein comprises at least one biologically active portion of a stem cell growth factor-like protein. In another embodiment, a stem cell growth factor-like fusion protein comprises at least two biologically active portions of a stem cell growth factor-like protein. In yet another embodiment, a stem cell growth factor-like fusion protein comprises at least three biologically active portions of a stem cell growth factor-like protein. Within the fusion protein, the term "operatively-linked" is intended to indicate that the stem cell growth factor-like polypeptide and the non-stem cell growth factor-like polypeptide are fused in-frame with one another. The non-stem cell growth factor-like polypeptide can be fused to the N-terminus or C-terminus of the stem cell growth factor-like polypeptide.

In one embodiment, the fusion protein is a GST-stem cell growth factor-like fusion protein in which the stem cell growth factor-like sequences are fused to the C-terminus of the GST (glutathione S-transferase) sequences. Such fusion proteins can facilitate the purification of recombinant stem cell growth factor-like polypeptides. In another embodiment, the fusion protein is a stem cell growth factor-like protein containing a heterologous signal sequence at its N-terminus. In certain host cells (e.g., mammalian host cells), expression and/or secretion of stem cell growth factor-like can be increased through use of a heterologous signal sequence.

In yet another embodiment, the fusion protein is a stem cell growth factor-like-immunoglobulin fusion protein in which the stem cell growth factor-like sequences are fused to sequences derived from a member of the immunoglobulin protein family. The stem cell growth factor-like-immunoglobulin fusion proteins of the invention can be incorporated into pharmaceutical compositions and administered to a subject to inhibit an interaction between a stem cell growth factor-like ligand and a stem cell growth factor-like protein on the surface of a cell, to thereby suppress stem cell growth factor-like-mediated signal transduction in vivo. The stem cell growth factor-like-immunoglobulin fusion proteins can be used to affect the bioavailability of a stem cell growth factor-like cognate ligand. Inhibition of the stem cell growth factor-like ligand/stem cell growth factor-like interaction can be useful therapeutically for both the treatment of proliferative and differentiative disorders, as well as modulating (e.g. promoting or inhibiting) cell survival. Moreover, the stem cell growth factor-like-immunoglobulin fusion proteins of the invention can be used as immunogens to produce anti-stem cell growth factor-like antibodies in a subject, to purify stem cell growth factor-like ligands, and in screening assays to identify molecules that inhibit the interaction of stem cell growth factor-like with a stem cell growth factor-like ligand.

A stem cell growth factor-like chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel, et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). A stem cell growth factor-like-encoding nucleic acid can be cloned into such an expression vector such that the fusion moiety is linked in-frame to the stem cell growth factor-like protein.

4.4 Polypeptides of the Invention

The isolated polypeptides of the invention include, but are not limited to, a polypeptide comprising: the amino acid sequence set forth as any one of SEQ ID NO: 3, 5-7, 9, 11, 13, 15, 18, 20-21, or 27 or an amino acid sequence encoded by any one of the nucleotide sequences SEQ ID NO: 1-2, 4, 8, 10, 12, 14, 16-17, 19, or 26 or the corresponding full length or mature protein. Polypeptides of the invention also include polypeptides preferably with biological or immunological activity that are encoded by: (a) a polynucleotide having any one of the nucleotide sequences set forth in SEQ ID NO: 1-2, 4, 8, 10, 12, 14, 16-17, 19, or 26 or (b) polynucleotides encoding any one of the amino acid sequences set forth as SEQ ID NO: 3, 5-7, 9, 11, 13, 15, 18, 20-21, or 27 or (c) polynucleotides that hybridize to the complement of the polynucleotides of either (a) or (b) under stringent hybridization conditions. The invention also provides biologically active or immunologically active variants of any of the amino acid sequences set forth as SEQ ID NO: 3, 5-7, 9, 11, 13, 15, 18, 20-21, or 27 or the corresponding full length or mature protein; and "substantial equivalents" thereof (e.g., with at least about 65%, at least about 70%, at least about 75%, at least about 80%, 81%, 82%, 83%, 84%, 85%, 86%, 87%, 88%, or 89%, more typically at least about 90%, 91%, 92%, 93%, or 94% and even more typically at least about 95%, 96%, 97%, 98% or 99%, most typically at least about 99% amino acid identity) that retain biological activity. Polypeptides encoded by allelic variants may have a similar, increased, or decreased activity compared to polypeptides comprising SEQ ID NO: 3, 5-7, 9, 11, 13, 15, 18, 20-21, or 27.

Fragments of the proteins of the present invention which are capable of exhibiting biological activity are also encompassed by the present invention. Fragments of the protein may be in linear form or they may be cyclized using known methods, for example, as described in H. U. Saragovi, et al., Bio/Technology 10, 773-778 (1992) and in R. S. McDowell, et al., J. Amer. Chem. Soc. 114, 9245-9253 (1992), both of which are incorporated herein by reference. Such fragments may be fused to carrier molecules such as immunoglobulins for many purposes, including increasing the valency of protein binding sites.

The present invention also provides both full-length and mature forms (for example, without a signal sequence or precursor sequence) of the disclosed proteins. The protein coding sequence is identified in the sequence listing by translation of the disclosed nucleotide sequences. The mature form of such protein may be obtained by expression of a full-length polynucleotide in a suitable mammalian cell or other host cell. The sequence of the mature form of the protein is also determinable from the amino acid sequence of the full-length form. Where proteins of the present invention are membrane bound, soluble forms of the proteins are also provided. In such forms, part or all of the regions causing the proteins to be membrane bound are deleted so that the proteins are fully secreted from the cell in which it is expressed.

Protein compositions of the present invention may further comprise an acceptable carrier, such as a hydrophilic, e.g., pharmaceutically acceptable, carrier.

The present invention further provides isolated polypeptides encoded by the nucleic acid fragments of the present invention or by degenerate variants of the nucleic acid fragments of the present invention. By "degenerate variant" is intended nucleotide fragments which differ from a nucleic acid fragment of the present invention (e.g., an ORF) by nucleotide sequence but, due to the degeneracy of the genetic code, encode an identical polypeptide sequence. Preferred nucleic acid fragments of the present invention are the ORFs that encode proteins.

A variety of methodologies known in the art can be utilized to obtain any one of the isolated polypeptides or proteins of the present invention. At the simplest level, the amino acid sequence can be synthesized using commercially available peptide synthesizers. The synthetically-constructed protein sequences, by virtue of sharing primary, secondary or tertiary structural and/or conformational characteristics with proteins may possess biological properties in common therewith, including protein activity. This technique is particularly useful in producing small peptides and fragments of larger polypeptides. Fragments are useful, for example, in generating antibodies against the native polypeptide. Thus, they may be employed as biologically active or immunological substitutes for natural, purified proteins in screening of therapeutic compounds and in immunological processes for the development of antibodies.

The polypeptides and proteins of the present invention can alternatively be purified from cells which have been altered to express the desired polypeptide or protein. As used herein, a cell is said to be altered to express a desired polypeptide or protein when the cell, through genetic manipulation, is made to produce a polypeptide or protein which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the polypeptides or proteins of the present invention.

The invention also relates to methods for producing a polypeptide comprising growing a culture of host cells of the invention in a suitable culture medium, and purifying the protein from the cells or the culture in which the cells are grown. For example, the methods of the invention include a process for producing a polypeptide in which a host cell containing a suitable expression vector that includes a polynucleotide of the invention is cultured under conditions that allow expression of the encoded polypeptide. The polypeptide can be recovered from the culture, conveniently from the culture medium, or from a lysate prepared from the host cells and further purified. Preferred embodiments include those in which the protein produced by such process is a full length or mature form of the protein.

In an alternative method, the polypeptide or protein is purified from bacterial cells which naturally produce the polypeptide or protein. One skilled in the art can readily follow known methods for isolating polypeptides and proteins in order to obtain one of the isolated polypeptides or proteins of the present invention. These include, but are not limited to, immunochromatography, HPLC, size-exclusion chromatography, ion-exchange chromatography, and immuno-affinity chromatography. See, e.g., Scopes, *Protein Purification: Principles and Practice*, Springer-Verlag (1994); Sambrook, et al., in Molecular Cloning: *A Laboratory Manual*; Ausubel et al., *Current Protocols in Molecular Biology*. Polypeptide fragments that retain biological/immunological activity include fragments comprising greater than about 100 amino acids, or greater than about 200 amino acids, and fragments that encode specific protein domains.

The purified polypeptides can be used in in vitro binding assays which are well known in the art to identify molecules which bind to the polypeptides. These molecules include but are not limited to, for e.g., small molecules, molecules from combinatorial libraries, antibodies or other proteins. The molecules identified in the binding assay are then tested for antagonist or agonist activity in in vivo tissue culture or animal models that are well known in the art. In brief, the molecules are titrated into a plurality of cell cultures or animals and then tested for either cell/animal death or prolonged survival of the animal/cells.

In addition, the peptides of the invention or molecules capable of binding to the peptides may be complexed with toxins, e.g., ricin or cholera, or with other compounds that are toxic to cells. The toxin-binding molecule complex is then targeted to a tumor or other cell by the specificity of the binding molecule for SEQ ID NO: 3, 5-7, 9, 11, 13, 15, 18, 20-21, or 27.

The protein of the invention may also be expressed as a product of transgenic animals, e.g., as a component of the milk of transgenic cows, goats, pigs, or sheep which are characterized by somatic or germ cells containing a nucleotide sequence encoding the protein.

The proteins provided herein also include proteins characterized by amino acid sequences similar to those of purified proteins but into which modification are naturally provided or deliberately engineered. For example, modifications, in the peptide or DNA sequence, can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein. Regions of the protein that are important for the protein function can be determined by various methods known in the art including the alanine-scanning method which involved systematic substitution of single or strings of amino acids with alanine, followed by testing the resulting alanine-containing variant for biological activity. This type of analysis determines the importance of the substituted amino acid(s) in biological activity. Regions of the protein that are important for protein function may be determined by the eMATRIX program.

Other fragments and derivatives of the sequences of proteins which would be expected to retain protein activity in whole or in part and are useful for screening or other immunological methodologies may also be easily made by those skilled in the art given the disclosures herein. Such modifications are encompassed by the present invention.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBat™ kit), and such methods are well known in the art, as described in Summers and Smith, Texas Agricultural Experiment Station Bulletin No. 1555 (1987), incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, Heparin-Toyopearl™ or Cibacrom blue 3GA Sepharose™; one or more steps involving hydrophobic interaction chromatography using such resins as phenyl ether, butyl ether, or propyl ether, or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX), or as a His tag. Kits for expression and purification of such fusion proteins are commercially available from New England BioLab (Beverly, Mass.), Pharmacia (Piscataway, N.J.) and Invitrogen, respectively. The protein can also be tagged with an epitope and subsequently purified by using a specific antibody directed to such epitope. One such epitope ("FLAG®") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The polypeptides of the invention include analogs (variants). The polypeptides of the invention include stem cell growth factor-like analogs. This embraces fragments of stem cell growth factor-like polypeptide of the invention, as well stem cell growth factor-like polypeptides which comprise one or more amino acids deleted, inserted, or substituted. Also, analogs of the stem cell growth factor-like polypeptide of the invention embrace fusions of the stem cell growth factor-like polypeptides or modifications of the stem cell growth factor-like polypeptides, wherein the stem cell growth factor-like polypeptide or analog is fused to another moiety or moieties, e.g., targeting moiety or another therapeutic agent. Such analogs may exhibit improved properties such as activity and/or stability. Examples of moieties which may be fused to the stem cell growth factor-like polypeptide or an analog include, for example, targeting moieties which provide for the delivery of polypeptide to neurons, e.g., antibodies to central nervous system, or antibodies to receptor and ligands expressed on neuronal cells. Other moieties which may be fused to stem cell growth factor-like polypeptide include therapeutic agents which are used for treatment, for example anti-depressant drugs or other medications for neurological disorders. Also, stem cell growth factor-like polypeptides may be fused to neuron growth modulators, and other chemokines for targeted delivery.

4.4.1 Determining Polypeptide and Polynucleotide Identity and Similarity

Preferred identity and/or similarity are designed to give the largest match between the sequences tested. Methods to determine identity and similarity are codified in computer programs including, but are not limited to, the GCG program package, including GAP (Devereux, J., et al., Nucleic Acids Research 12(1):387 (1984); Genetics Computer Group, University of Wisconsin, Madison, Wis.), BLASTP, BLASTN, BLASIX, FASTA (Altschul, S. F. et al., J. Molec. Biol. 215: 403-410 (1990), PSI-BLAST (Altschul S. et al., Nucleic Acids Res. vol. 25, pp. 3389-3402, herein incorporated by reference), the eMatrix software (Wu et al., J. Comp. Biol., vol. 6, pp. 219-235 (1999), herein incorporated by reference), eMotif software (Nevill-Manning et al, ISMB-97, vol 4, pp. 202-209, herein incorporated by reference), the GeneAtlas software (Molecular Simulations Inc. (MSI), San Diego, Calif.) (Sanchez and Sali (1998) Proc. Natl. Acad. Sci., 95, 13597-13602; Kitson D H et al, (2000) "Remote homology detection using structural modeling—an evaluation" Submitted; Fischer and Eisenberg (1996) Protein Sci. 5, 947-955), and the Kyte-Doolittle hydrophobocity prediction algorithm (J. Mol. Biol, 157, pp. 105-31 (1982), incorporated herein by reference). The BLAST programs are publicly available from the National Center for Biotechnology Information (NCBI) and other sources (BLAST Manual, Altschul, S., et al. NCB NLM NIH Bethesda, Md. 20894; Altschul, S., et al., J. Mol. Biol. 215:403-410 (1990).

4.5 Gene Therapy

Mutations in the polynucleotides of the invention gene may result in loss of normal function of the encoded protein. The invention thus provides gene therapy to restore normal activity of the polypeptides of the invention; or to treat disease states involving polypeptides of the invention. Delivery of a functional gene encoding polypeptides of the invention to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson, Nature, supplement to vol. 392, no. 6679, pp. 25-20 (1998). For additional reviews of gene therapy technology see Friedmann, Science, 244: 1275-1281 (1989); Verma, Scientific American: 68-84 (1990); and Miller, Nature, 357: 455-460 (1992). Introduction of any one of the nucleotides of the present invention or a gene encoding the polypeptides of the present invention can also be accomplished with extrachromosomal substrates (transient expression) or artificial chromosomes (stable expression). Cells may also be cultured ex vivo in the presence of proteins of the present invention in order to proliferate or to produce a desired effect on or activity in such cells. Treated cells can then be introduced in vivo for therapeutic purposes. Alternatively, it is contemplated that in other human disease states, preventing the expression of or inhibiting the activity of polypeptides of the invention will be useful in treating the disease states. It is contemplated that antisense therapy or gene therapy could be applied to negatively regulate the expression of polypeptides of the invention.

Other methods inhibiting expression of a protein include the introduction of antisense molecules to the nucleic acids of the present invention, their complements, or their translated RNA sequences, by methods known in the art. Further, the polypeptides of the present invention can be inhibited by using targeted deletion methods, or the insertion of a negative regulatory element such as a silencer, which is tissue specific.

The present invention still further provides cells genetically engineered in vivo to express the polynucleotides of the invention, wherein such polynucleotides are in operative association with a regulatory sequence heterologous to the host cell which drives expression of the polynucleotides in the cell. These methods can be used to increase or decrease the expression of the polynucleotides of the present invention.

Knowledge of DNA sequences provided by the invention allows for modification of cells to permit, increase, or decrease, expression of endogenous polypeptide. Cells can be modified (e.g., by homologous recombination) to provide increased polypeptide expression by replacing, in whole or in part, the naturally occurring promoter with all or part of a heterologous promoter so that the cells express the protein at higher levels. The heterologous promoter is inserted in such a manner that it is operatively linked to the desired protein encoding sequences. See, for example, PCr International Publication No. WO 94/12650, PCT International Publication No. WO 92/20808, and PCT International Publication No. WO 91/09955. It is also contemplated that, in addition to heterologous promoter DNA, amplifiable marker DNA (e.g., ada, dhfr, and the multifunctional CAD gene which encodes carbamyl phosphate synthase, aspartate transcarbamylase, and dihydroorotase) and/or intron DNA may be inserted along with the heterologous promoter DNA. If linked to the desired protein coding sequence, amplification of the marker DNA by standard selection methods results in co-amplification of the desired protein coding sequences in the cells.

In another embodiment of the present invention, cells and tissues may be engineered to express an endogenous gene comprising the polynucleotides of the invention under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods. Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting. These sequences include polyadenylation signals, mRNA stability elements, splice sites, leader sequences for enhancing or modifying transport or secretion properties of the protein, or other sequences which alter or improve the function or stability of protein or RNA molecules.

The targeting event may be a simple insertion of the regulatory sequence, placing the gene under the control of the new regulatory sequence, e.g., inserting a new promoter or enhancer or both upstream of a gene. Alternatively, the targeting event may be a simple deletion of a regulatory element, such as the deletion of a tissue-specific negative regulatory element. Alternatively, the targeting event may replace an existing element; for example, a tissue-specific enhancer can be replaced by an enhancer that has broader or different cell-type specificity than the naturally occurring elements. Here, the naturally occurring sequences are deleted and new sequences are added. In all cases, the identification of the targeting event may be facilitated by the use of one or more selectable marker genes that are contiguous with the targeting DNA, allowing for the selection of cells in which the exogenous DNA has integrated into the cell genome. The identification of the targeting event may also be facilitated by the use of one or more marker genes exhibiting the property of negative selection, such that the negatively selectable marker is linked to the exogenous DNA, but configured such that the negatively selectable marker flanks the targeting sequence, and such that a correct homologous recombination event with sequences in the host cell genome does not result in the stable integration of the negatively selectable marker. Markers useful for this purpose include the Herpes Simplex Virus thymidine kinase (TK) gene or the bacterial xanthine-guanine phosphoribosyl-transferase (gpt) gene.

The gene targeting or gene activation techniques which can be used in accordance with this aspect of the invention are more particularly described in U.S. Pat. No. 5,272,071 to Chappel; U.S. Pat. No. 5,578,461 to Sherwin et al.; International Application No. PCT/US92/09627 (WO93/09222) by Selden et al.; and International Application No. PCT/US90/06436 (WO91/06667) by Skoultchi et al., each of which is incorporated by reference herein in its entirety.

4.6 Transgenic Animals

In preferred methods to determine biological functions of the polypeptides of the invention in vivo, one or more genes provided by the invention are either over expressed or inactivated in the germ line of animals using homologous recombination [Capecchi, Science 244:1288-1292 (1989)]. Animals in which the gene is over expressed, under the regulatory control of exogenous or endogenous promoter elements, are known as transgenic animals. Animals in which an endogenous gene has been inactivated by homologous recombination are referred to as "knockout" animals. Knockout animals, preferably non-human mammals, can be prepared as described in U.S. Pat. No. 5,557,032, incorporated herein by reference. Transgenic animals are useful to determine the roles polypeptides of the invention play in biological processes, and preferably in disease states. Transgenic animals are useful as model systems to identify compounds that modulate lipid metabolism. Transgenic animals, preferably non-human mammals, are produced using methods as described in U.S. Pat. No. 5,489,743 and PCT Publication No. WO94/28122, incorporated herein by reference.

Transgenic animals can be prepared wherein all or part of a promoter of the polynucleotides of the invention is either activated or inactivated to alter the level of expression of the polypeptides of the invention. Inactivation can be carried out using homologous recombination methods described above. Activation can be achieved by supplementing or even replacing the homologous promoter to provide for increased protein expression. The homologous promoter can be supplemented by insertion of one or more heterologous enhancer elements known to confer promoter activation in a particular tissue.

The polynucleotides of the present invention also make possible the development, through, e.g., homologous recombination or knock out strategies; of animals that fail to express functional stem cell growth factor-like polypeptide or that express a variant of stem cell growth factor-like polypeptide. Such animals are useful as models for studying the in vivo activities of stem cell growth factor-like polypeptide as well as for studying modulators of the stem cell growth factor-like polypeptide.

In preferred methods to determine biological functions of the polypeptides of the invention in vivo, one or more genes provided by the invention are either over expressed or inactivated in the germ line of animals using homologous recombination [Capecchi, Science 244:1288-1292 (1989)]. Animals in which the gene is over expressed, under the regulatory control of exogenous or endogenous promoter elements, are known as transgenic animals. Animals in which an endogenous gene has been inactivated by homologous recombination are referred to as "knockout" animals. Knockout animals, preferably non-human mammals, can be prepared as described in U.S. Pat. No. 5,557,032, incorporated herein by reference. Transgenic animals are useful to determine the roles polypeptides of the invention play in biological processes, and preferably in disease states. Transgenic animals are useful as model systems to identify compounds that modulate lipid metabolism. Transgenic animals, preferably non-human mammals, are produced using methods as described in U.S. Pat. No. 5,489,743 and PCT Publication No. WO94/28122, incorporated herein by reference.

Transgenic animals can be prepared wherein all or part of the polynucleotides of the invention promoter is either activated or inactivated to alter the level of expression of the polypeptides of the invention. Inactivation can be carried out using homologous recombination methods described above. Activation can be achieved by supplementing or even replacing the homologous promoter to provide for increased protein expression. The homologous promoter can be supplemented by insertion of one or more heterologous enhancer elements known to confer promoter activation in a particular tissue.

4.7 Uses and Biological Activity of Human Stem Cell Growth Factor-Like Polypeptide The polynucleotides and proteins of the present invention are expected to exhibit one or more of the uses or biological activities (including those associated with assays cited herein) identified herein. Uses or activities described for proteins of the present invention may be provided by administration or use of such proteins or of polynucleotides encoding such proteins (such as, for example, in gene therapies or vectors suitable for introduction of DNA). The mechanism underlying the particular condition or pathology will dictate whether the polypeptides of the invention, the polynucleotides of the invention or modulators (activators or inhibitors) thereof would be beneficial to the subject in need of treatment. Thus, "therapeutic compositions of the invention" include compositions comprising isolated polynucleotides (including recombinant DNA molecules, cloned genes and degenerate variants thereof) or polypeptides of the invention (including full length protein, mature protein and truncations or domains thereof), or compounds and other substances that modulate the overall activity of the target gene products, either at the level of target gene/protein expression or target protein activity. Such modulators include polypeptides, analogs, (variants), including fragments and fusion proteins, antibodies and other binding proteins; chemical compounds that directly or indirectly activate or inhibit the polypeptides of the invention (identified, e.g., via drug screening assays as described herein); antisense polynucleotides and polynucleotides suitable for triple helix formation; and in particular antibodies or other binding partners that specifically recognize one or more epitopes of the polypeptides of the invention.

The polypeptides of the present invention may likewise be involved in cellular activation or in one of the other physiological pathways described herein.

4.7.1 Research Uses and Utilities

The polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on gels; as chromosome markers or tags (when labeled) to identify chromosomes or to map related gene positions; to compare with endogenous DNA sequences in patients to identify potential genetic disorders;

as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791-803 (1993)) to identify polynucleotides encoding the other protein with which binding occurs or to identify inhibitors of the binding interaction.

The polypeptides provided by the present invention can similarly be used in assays to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding polypeptide is preferentially expressed (either constitutively or at a particular stage of tissue differentiation or development or in a disease state); and, of course, to isolate correlative receptors or ligands. Proteins involved in these binding interactions can also be used to screen for peptide or small molecule inhibitors or agonists of the binding interaction.

The polypeptides of the invention are also useful for making antibody substances that are specifically immunoreactive with stem cell growth factor-like proteins. Antibodies and portions thereof (e.g., Fab fragments) which bind to the polypeptides of the invention can be used to identify the presence of such polypeptides in a sample. Such determinations are carried out using any suitable immunoassay format, and any polypeptide of the invention that is specifically bound by the antibody can be employed as a positive control.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

4.7.2 Nutritional Uses

Polynucleotides and polypeptides of the present invention can also be used as nutritional sources or supplements. Such uses include without limitation use as a protein or amino acid supplement, use as a carbon source, use as a nitrogen source and use as a source of carbohydrate. In such cases the polypeptide or polynucleotide of the invention can be added to the feed of a particular organism or can be administered as a separate solid or liquid preparation, such as in the form of powder, pills, solutions, suspensions or capsules. In the case of microorganisms, the polypeptide or polynucleotide of the invention can be added to the medium in or on which the microorganism is cultured.

Additionally, the polypeptides of the invention can be used as markers, and as a food supplement A polypeptide consisting of SEQ ID NO: 6, for example, has a molecular mass of approximately 26 kDa in its unprocessed and unglycosylated state. Protein food supplements are well known and the formulation of suitable food supplements including polypeptides of the invention is within the level of skill in the food preparation art.

4.7.3 Cytokine and Cell Proliferation/Differentiation Activity

A polypeptide of the present invention may exhibit activity relating to cytokine, cell proliferation (either inducing or inhibiting) or cell differentiation (either inducing or inhibiting) activity or may induce production of other cytokines in certain cell populations. A polynucleotide of the invention can encode a polypeptide exhibiting such attributes. Many protein factors discovered to date, including all known cytokines, have exhibited activity in one or more factor-dependent cell proliferation assays, and hence the assays serve as a convenient confirmation of cytokine activity. The activity of therapeutic compositions of the present invention is evidenced by any one of a number of routine factor dependent cell proliferation assays for cell lines including, without limitation, 32D, DA2, DA1G, T10, B9, B9/11, BaF3, MC9/G, M+(preB M+), 2E8, RB5, DA1, 123, T1165, HT2, CTLL2, TF-1, Mo7e, CMK, HUVEC, and Caco. Therapeutic compositions of the invention can be used in the following:

Assays for T-cell or thymocyte proliferation include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1-3.19; Chapter 7, Immunologic studies in Humans); Takai et al., J. Immunol. 137: 3494-3500, 1986; Bertagnolli et al., J. Immunol. 145:1706-1712, 1990; Bertagnolli et al., Cellular Immunology 133: 327-341, 1991; Bertagnori, et al., I. Immunol. 149:3778-3783, 1992; Bowman et al., I. Immunol. 152:1756-1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In Current Protocols in Immunology. J. E. e.a. Coligan eds. Vol 1 pp. 3.12.1-3.12.14, John Wiley and Sons, Toronto. 1994; and Measurement of mouse and human interleukin-□, Schreiber, R. D. In Current Protocols in Immunology. J. E. e.a. Coligan eds. Vol 1 pp. 6.8.1-6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S, and Lipsky, P. E. In Current Protocols in Immunology. J. E. e.a. Coligan eds. Vol 1 pp. 6.3.1-6.3.12, John Wiley and Sons, Toronto. 1991; deVries et al., J. Exp. Med. 173:1205-1211, 1991; Moreau et al., Nature 336:690-692, 1988; Greenberger et al., Proc. Natl. Acad. Sci. U.S.A. 80:2931-2938, 1983; Measurement of mouse and human interleukin 6-Nordan, R. In Current Protocols in Immunology. J. B. Coligan eds. Vol 1 pp. 6.6.1-6.6.5, John Wiley and Sons, Toronto. 1991; Smith et al., Proc. Natl. Aced. Sci. U.S.A. 83:1857-1861, 1986; Measurement of human Interleulin 11—Bennett, F., Giannotti, J., Clark, S. C. and Turner, K. J. In Current Protocols in Immunology. J. E. Coligan eds. Vol 1 pp. 6.15.1 John Wiley and Sons, Toronto. 1991; Measurement of mouse and human Interleukin 9-Carletta, A., Giannotti, J., Clark, S. C. and Turner, K. J. In Current Protocols in Immunology. J. E. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margilies, E. M. Shevach, W Strober, Pub. Greene Publishing Associates and Wiley-Interscience (Chapter 3, In Vitro assays for Mouse Lymphocyte Function; Chapter 6, Cytolines and their cellular receptors; Chapter 7, Immunologic studies in Humans); Weinberger et al., Proc. Natl. Acad. Sci. USA 77:6091-6095, 1980; Weinberger et al., Eur. J. Immun. 11:405-411, 1981; Takai et al., J. Immunol. 137:3494-3500, 1986; Takai et al., J. Immunol. 140:508-512, 1988.

4.7.4 Stem Cell Growth Factor Activity

A polypeptide of the present invention may exhibit stem cell growth factor activity and be involved in the proliferation, differentiation and survival of pluripotent and totipotent stem cells including primordial germ cells, embryonic stem cells, hematopoietic stem cells and/or germ line stem cells. Administration of the polypeptide of the invention to stem cells in vivo or ex vivo may maintain and expand cell populations in a totipotential or pluripotential state which would be useful for re-engineering damaged or diseased tissues, transplantation, manufacture of bio-pharmaceuticals and the development of bio-sensors. The ability to produce large quantities of human cells has important working applications for the production of human proteins which currently must be obtained from non-human sources or donors, implantation of cells to treat diseases such as Parkinson's, Alzheimer's and other neurodegenerative diseases; tissues for grafting such as bone marrow, skin, cartilage, tendons, bone, muscle (including cardiac muscle), blood vessels, cornea, neural cells, gastrointestinal cells and others; and organs for transplantation such as kidney, liver, pancreas (including islet cells), heart and lung.

It is contemplated that multiple different exogenous growth factors and/or cytokines may be administered in combination with the polypeptide of the invention to achieve the desired effect, including any of the growth factors listed herein, other stem cell maintenance factors, and specifically including stem cell factor (SCF), leukemia inhibitory factor (LIF), Flt-3 ligand (Flt-3L), any of the interleukins, recombinant soluble IL=6 receptor fused to IL-6, macrophage inflammatory protein 1-alpha (MIP-1-alpha), G-CSF, GM-CSF, thrombopoietin (TPO), platelet factor 4 (PF4), platelet-derived growth factor (PDGF), neural growth factors and basic fibroblast growth factor (bFGF).

Since totipotent stem cells can give rise to virtually any mature cell type, expansion of these cells in culture will facilitate the production of large quantities of mature cells. Techniques for culturing stem cells are known in the art and administration of polypeptides of the invention, optionally with other growth factors and/or cytokines, is expected to enhance the survival and proliferation of the stem cell populations. This can be accomplished by direct administration of the polypeptide of the invention to the culture medium. Alternatively, stroma cells transfected with a polynucleotide that encodes for the polypeptide of the invention can be used as a feeder layer for the stem cell populations in culture or in vivo. Stromal support cells for feeder layers may include embryonic bone marrow fibroblasts, bone marrow stromal cells, fetal liver cells, or cultured embryonic fibroblasts (see U.S. Pat. No. 5,690,926).

Stem cells themselves can be transfected with a polynucleotide of the invention to induce autocrine expression of the polypeptide of the invention. This will allow for generation of undifferentiated totipotential/pluripotential stem cell lines that are useful as is or that can then be differentiated into the desired mature cell types. These stable cell lines can also serve as a source of undifferentiated totipotential/pluripotential mRNA to create cDNA libraries and templates for polymerase chain reaction experiments. These studies would allow for the isolation and identification of differentially expressed genes in stem cell populations that regulate stem cell proliferation and/or maintenance.

Expansion and maintenance of totipotent stem cell populations will be useful in the treatment of many pathological conditions. For example, polypeptides of the present invention may be used to manipulate stem cells in culture to give rise to neuroepithelial cells that can be used to augment or replace cells damaged by illness, autoimmune disease, accidental damage or genetic disorders. The polypeptide of the invention may be useful for inducing the proliferation of neural cells and for the regeneration of nerve and brain tissue, i.e. for the treatment of central and peripheral nervous system diseases and neuropathies, as well as mechanical and traumatic disorders which involve degeneration, death or trauma to neural cells or nerve tissue. Furthermore, these cells can be cultured in vitro to form other differentiated cells, such as skin tissue that can be used for transplantation. In addition, the expanded stem cell populations can also be genetically altered for gene therapy purposes and to decrease host rejection of replacement tissues after grafting or implantation.

Expression of the polypeptide of the invention and its effect on stem cells can also be manipulated to achieve controlled differentiation of the stem cells into more differentiated cell types. A broadly applicable method of obtaining pure populations of a specific differentiated cell type from undifferentiated stem cell populations involves the use of a cell-type specific promoter driving a selectable marker. The selectable marker allows only cells of the desired type to survive. For example, stem cells can be induced to differentiate into cardiomyocytes (Wobus et al., Differentiation, 48: 173-182, (1991); Kiug et al., J. Clin. Invest., 98(1): 216-224, (1998)) or skeletal muscle cells (Browder, L. W. In: *Principles of Tissue Engineering eds*. Lanza et al., Academic Press (1997)). Alternatively, directed differentiation of stem cells can be accomplished by culturing the stem cells in the presence of a differentiation factor such as retinoic acid and an antagonist of the polypeptide of the invention which would inhibit the effects of endogenous stem cell factor activity and allow differentiation to proceed.

In vitro cultures of stem cells can be used to determine if the polypeptide of the invention exhibits stem cell growth factor activity. Stem cells are isolated from any one of various cell sources (including hematopoietic stem cells and embryonic stem cells) and cultured on a feeder layer, as described by Thompson et al. Proc. Natl. Acad. Sci, U.S.A., 92: 7844-7848 (1995), in the presence of the polypeptide of the invention alone or in combination with other growth factors or cytokines. The ability of the polypeptide of the invention to induce stem cells proliferation is determined by colony formation on semi-solid support e.g. as described by Bernstein et al., Blood, 77: 2316-2321 (1991).

4.7.5 Hematopoiesis Regulating Activity

A polypeptide of the present invention may be involved in regulation of hematopoiesis and, consequently, in the treatment of myeloid or lymphoid cell disorders. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional colony stimulating factor activity) useful, for example, in conjunction with chemotherapy to prevent or treat consequent myelosuppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

Therapeutic compositions of the invention can be used in the following:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. Cellular Biology 15:141-151, 1995; Keller et al., Molecular and Cellular Biology 13:473-486, 1993; McClanahan et al., Blood 81:2903-2915, 1993.

Assays for stem cell survival and differentiation (which will identify, among others, proteins that regulate lympho-hematopoiesis) include, without limitation, those described in: Methylcellulose colony forming assays, Freshney, M. G. In Culture of Hematopoietic Cells. R. I. Freshney, et al. eds. Vol pp. 265-268, Wiley-Liss, Inc., New York, N.Y. 1994; Hirayama et al., Proc. Natl. Acad. Sci. USA 89:5907-5911, 1992; Primitive hematopoietic colony forming cells with high proliferative potential, McNiece, I. K and Briddell, R. A. In Culture of Hematopoietic Cells. R. I. Freshney, et al. eds. Vol pp. 23-39, Wiley-Liss, Inc., New York, N.Y. 1994; Neben et al., Experimental Hematology 22:353-359, 1994; Cobblestone area forming cell assay, Ploemacher, R. E. In Culture of Hematopoietic Cells. R. I. Freshney, et al. eds. Vol pp. 1-21, Wiley-Liss, Inc., New York, N.Y. 1994; Long term bone marrow cultures in the presence of stromal cells, Spooncer, E., Dexter, M. and Allen, T. In Culture of Hematopoietic Cells. R. I. Freshney, et al. eds. Vol pp. 163-179, Wiley-Liss, Inc., New York, N.Y. 1994; Long term culture initiating cell assay, Sutherland, H. J. In Culture of Hematopoietic Cells. R. I. Freshney, et al. eds. Vol pp. 139-162, Wiley-Liss, Inc., New York, N.Y. 1994.

4.7.6 Tissue Growth Activity

A polypeptide of the present invention also may be involved in bone, cartilage, tendon, ligament and/or nerve tissue growth or regeneration, as well as in wound healing and tissue repair and replacement, and in healing of burns, incisions and ulcers.

A polypeptide of the present invention which induces cartilage and/or bone growth in circumstances where bone is not normally formed, has application in the healing of bone fractures and cartilage damage or defects in humans and other animals. Compositions of a polypeptide, antibody, binding partner, or other modulator of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A polypeptide of this invention may also be involved in attracting bone-forming cells, stimulating growth of bone-forming cells, or inducing differentiation of progenitors of bone-forming cells. Treatment of osteoporosis, osteoarthritis, bone degenerative disorders, or periodontal disease, such as through stimulation of bone and/or cartilage repair or by blocking inflammation or processes of tissue destruction (collagenase activity, osteoclast activity, etc.) mediated by inflammatory processes may also be possible using the composition of the invention.

Another category of tissue regeneration activity that may involve the polypeptide of the present invention is tendon/ligament formation. Induction of tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The compositions of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a composition may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a composition of the invention.

Compositions of the invention may also be useful to promote better or faster closure of non-healing wounds, including without limitation pressure ulcers, ulcers associated with vascular insufficiency, surgical and traumatic wounds, and the like.

Compositions of the present invention may also be involved in the generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring may allow normal tissue to regenerate. A polypeptide of the present invention may also exhibit angiogenic activity.

A composition of the present invention may also be useful for gut protection or regeneration and treatment of lung or liver fibrosis, reperfusion injury in various tissues, and conditions resulting from systemic cytokine damage.

A composition of the present invention may also be useful for promoting or inhibiting differentiation of tissues described above from precursor tissues or cells; or for inhibiting the growth of tissues described above.

Therapeutic compositions of the invention can be used in the following:

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium).

Assays for wound healing activity include, without limitation, those described in: Winter, Epidermal Wound Healing, pp. 71-112 (Maibach, H. I. and Rovee, D. T., eds.), Year Book Medical Publishers, Inc., Chicago, as modified by Eaglstein and Mertz, J. Invest. Dermatol 71:382-84 (1978).

4.7.7 Immune Function Stimulating or Suppressing Activity

A polypeptide of the present invention may also exhibit immune stimulating or immune suppressing activity, including without limitation the activities for which assays are described herein. A polynucleotide of the invention can encode a polypeptide exhibiting such activities. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases causes by viral, bacterial, fungal or other infection may be treatable using a protein of the present invention, including infections by HIV, hepatitis viruses, herpes viruses, mycobacteria, *Leishmania* spp., malaria spp. and various fungal infections such as candidiasis. Of course, in this regard, proteins of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitis, myasthenia gravis, graft-versus-host disease and autoimmune inflammatory eye disease. Such a protein (or antagonists thereof, including antibodies) of the present invention may also to be useful in the treatment of allergic reactions and conditions (e.g., anaphylaxis, serum sickness, drug reactions, food allergies, insect venom allergies, mastocytosis, allergic rhinitis, hypersensitivity pneumonitis, urticaria, angioedema, eczema, atopic dermatitis, allergic contact dermatitis, erythema multiforme, Stevens-Johnson syndrome, allergic conjunctivitis, atopic keratoconjunctivitis, venereal keratoconjunctivitis, giant papillary conjunctivitis and contact allergies), such as asthma particularly allergic asthma) or other respiratory problems. Other conditions, in which immune suppression is desired (including, for example, organ transplantation), may also be treatable using a protein (or antagonists thereof) of the present invention. The therapeutic effects of the polypeptides or antagonists thereof on allergic reactions can be evaluated by in vivo animals models such as the cumulative contact enhancement test (Lastbom et al., Toxicology 125: 59-66, 1998), skin prick test (Hoffmann et al., Allergy 54: 446-54, 1999), guinea pig skin sensitization test (Vohr et al., Arch. Toxocol. 73: 501-9), and murine local lymph node assay (Kimber et al., J. Toxicol. Environ. Health 53: 563-79).

Using the proteins of the invention it may also be possible to modulate immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a therapeutic composition of the invention may prevent cytokine synthesis by immune cells, such as T cells, and thus acts as an immunosuppressant. Moreover, a lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular therapeutic compositions in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789-792 (1992) and Turka et al., Proc. Natl. Acad. Sci. USA, 89:11102-11105 (1992). In addition, murine models of GVHD (see Paul ed., Fundamental Immunology, Raven Press, New York, 1989, pp. 846-847) can be used to determine the effect of therapeutic compositions of the invention on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block stimulation of T cells can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythematosus in MRL/lpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840-856).

Upregulation of an antigen function (e.g., a B lymphocyte antigen function), as a means of up regulating immune responses, may also be useful in therapy. Upregulation of immune responses may be in the form of enhancing an existing immune response or eliciting an initial immune response. For example, enhancing an immune response may be useful in cases of viral infection, including systemic viral diseases such as influenza, the common cold, and encephalitis.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

A polypeptide of the present invention may provide the necessary stimulation signal to T cells to induce a T cell mediated immune response against the transfected tumor cells. In addition, tumor cells which lack MHC class I or MHC class II molecules, or which fail to reexpress sufficient mounts of MHC class I or MHC class II molecules, can be transfected with nucleic acid encoding all or a portion of (e.g., a cytoplasmic-domain truncated portion) of an MHC class I alpha chain protein and $\beta_2$ microglobulin protein or an MHC class II alpha chain protein and an MHC class II beta chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1-3.19; Chapter 7, Immunologic studies in Humans); Herrmann et al., Proc. Natl. Acad. Sci. USA 78:2488-2492, 1981; Herrmann et al., J. Immunol. 128:1968-1974, 1982; Handa et al., J. Immunol. 135:1564-1572, 1985; Takai et al., I. Immunol. 137: 3494-3500, 1986; Takai et al., J. Immunol. 140:508-512, 1988; Bowman et al., J. Virology 61:1992-1998; Bertagnolli et al., Cellular Immunology 133:327-341, 1991; Brown et al., J. Immunol. 153:3079-3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028-3033, 1990; and Assays for B cell function: In vitro antibody production, Mond, J. J. and Brunswick, M. In Current Protocols in Immunology. J. E. e.a. Coligan eds. Vol 1 pp. 3.8.1-3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1-3.19; Chapter 7, Immunologic studies in Humans); Takai et al., J. Immunol. 137:3494-3500, 1986; Takai et al., J. Immunol. 140:508-512, 1988; Bertagnolli et al., J. Immunol. 149:3778-3783, 1992.

Dendritic cell-dependent assays (which will identify, among others, proteins expressed by dendritic cells that activate naive T-cells) include, without limitation, those described in: Guery et al., J. Immunol. 134:536-544, 1995; Inaba et al., Journal of Experimental Medicine 173:549-559, 1991; Macatonia et al., Journal of Immunology 154:5071-5079, 1995; Porgador et al., Journal of Experimental Medicine 182:255-260, 1995; Nair et al., Journal of Virology 67:4062-4069, 1993; Huang et al., Science 264:961-965, 1994; Macatonia et al., Journal of Experimental Medicine 169:1255-1264, 1989; Bhardwaj et al., Journal of Clinical Investigation 94:797-807, 1994; and Inaba et al., Journal of Experimental Medicine 172:631-640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795-808, 1992; Gorczyca et al., Leukemia 7:659-670, 1993; Gorczyca et al., Cancer Research 53:1945-1951, 1993; Itoh et al., Cell 66:233-243, 1991; Zacharchuk, Journal of Immunology 145:4037-4045, 1990; Zamai et al., Cytometry 14:891-897, 1993; Gorczyca et al., International Journal of Oncology 1:639-648, 1992.

Assays for proteins that influence early steps of T-cell commitment and development include, without limitation, those described in: Antica et al., Blood 84:111-117, 1994; Fine et al., Cellular Immunology 155:111-122, 1994; Galy et al., Blood 85:2770-2778, 1995; Toki et al., Proc. Nat. Acad. Sci. USA 88:7548-7551, 1991.

4.7.8 Chemotactic/Chemokinetic Activity

A polypeptide of the present invention may be involved in chemotactic or chemokinetic activity for mammalian cells, including, for example, monocytes, fibroblasts, neutrophils, T-ells, mast cells, eosinophils, epithelial and/or endothelial cells. A polynucleotide of the invention can encode a polypeptide exhibiting such attributes. Chemotactic and chemokinetic receptor activation can be used to mobilize or attract a desired cell population to a desired site of action. Chemotactic or chemokinetic compositions (e.g. proteins, antibodies, binding partners, or modulators of the invention) provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

Therapeutic compositions of the invention can be used in the following:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Marguiles, E. M. Shevach, W. Strober, Pub. Greene Publishing Associates and Wiley-Interscience (Chapter 6.12, Measurement of alpha and beta Chemokines 6.12.1-6.12.28; Taub et al. J. Clin. Invest. 95:1370-1376, 1995; Lind et al. APMIS 103:140-146, 1995; Muller et al Eur. J. Immunol. 25:1744-1748; Gruber et al. J. of Immunol. 152:5860-5867, 1994; Johnston et al. J. of Immunol. 153:1762-1768, 1994.

4.7.9 Hemostatic and Thrombolytic Activity

A polypeptide of the invention may also be involved in hemostatis or thrombolysis or thrombosis. A polynucleotide of the invention can encode a polypeptide exhibiting such attributes. Compositions may be useful in treatment of various coagulation disorders (including hereditary disorders, such as hemophilias) or to enhance coagulation and other hemostatic events in treating wounds resulting from trauma, surgery or other causes. A composition of the invention may also be useful for dissolving or inhibiting formation of thromboses and for treatment and prevention of conditions resulting therefrom (such as, for example, infarction of cardiac and central nervous system vessels (e.g., stroke).

Therapeutic compositions of the invention can be used in the following:

Assay for hemostatic and thrombolytic activity include, without limitation, those described in: Linet et al., J. Clin. Pharmacol. 26:131-140, 1986; Burdick et al., Thrombosis Res. 45:413-419, 1987; Humphrey et al., Fibrinolysis 5:71-79 (1991); Schaub, Prostaglandins 35:467-474, 1988.

4.7.10 Cancer Diagnosis and Therapy

Polypeptides of the invention may be involved in cancer cell generation, proliferation or metastasis. Detection of the presence or amount of polynucleotides or polypeptides of the invention may be useful for the diagnosis and/or prognosis of one or more types of cancer. For example, the presence or increased expression of a polynucleotide/polypeptide of the invention may indicate a hereditary risk of cancer, a precancerous condition, or an ongoing malignancy. Conversely, a defect in the gene or absence of the polypeptide may be associated with a cancer condition. Identification of single nucleotide polymorphisms associated with cancer or a predisposition to cancer may also be useful for diagnosis or prognosis.

Cancer treatments promote tumor regression by inhibiting tumor cell proliferation, inhibiting angiogenesis (growth of new blood vessels that is necessary to support tumor growth) and/or prohibiting metastasis by reducing tumor cell motility or invasiveness. Therapeutic compositions of the invention may be effective in adult and pediatric oncology including in solid phase tumors/malignancies, locally advanced tumors, human soft tissue sarcomas, metastatic cancer, including lymphatic metastases, blood cell malignancies including multiple myeloma, acute and chronic leukemias, and lymphomas, head and neck cancers including mouth cancer, larynx cancer and thyroid cancer, lung cancers including small cell carcinoma and non-small cell cancers, breast cancers including small cell carcinoma and ductal carcinoma, gastrointestinal cancers including esophageal cancer, stomach cancer, colon cancer, colorectal cancer and polyps associated with colorectal neoplasia, pancreatic cancers, liver cancer, urologic cancers including bladder cancer and prostate cancer, malignancies of the female genital tract including ovarian carcinoma, uterine (including endometrial) cancers, and solid tumor in the ovarian follicle, kidney cancers including renal cell carcinoma, brain cancers including intrinsic brain tumors, neuroblastoma, astrocytic brain tumors, gliomas, metastatic tumor cell invasion in the central nervous system, bone cancers including osteomas, skin cancers including malignant melanoma, tumor progression of human skin keratinocytes, squamous cell carcinoma, basal cell carcinoma, hemangiopericytoma and Karposi's sarcoma.

Polypeptides, polynucleotides, or modulators of polypeptides of the invention (including inhibitors and stimulators of the biological activity of the polypeptide of the invention) may be administered to treat cancer. Therapeutic compositions can be administered in therapeutically effective dosages alone or in combination with adjuvant cancer therapy such as surgery, chemotherapy, radiotherapy, thermotherapy, and laser therapy, and may provide a beneficial effect, e.g. reducing tumor size, slowing rate of tumor growth, inhibiting metastasis, or otherwise improving overall clinical condition, without necessarily eradicating the cancer.

The composition can also be administered in therapeutically effective amounts as a portion of an anti-cancer cocktail. An anti-cancer cocktail is a mixture of the polypeptide or modulator of the invention with one or more anti-cancer drugs in addition to a pharmaceutically acceptable carrier for delivery. The use of anti-cancer cocktails as a cancer treatment is routine. Anti-cancer drugs that are well known in the art and can be used as a treatment in combination with the polypeptide or modulator of the invention include: Actinomycin D, Aminoglutethimide, Asparaginase, Bleomycin, Busulfan, Carboplatin, Carmustine, Chlorambucil, Cisplatin (cis-DDP), Cyclophosphamide, Cytarabine HCl (Cytosine arabinoside), Dacarbazine, Dactinomycin, Daunorubicin HCl, Doxorubicin HCl, Estramustine phosphate sodium, Etoposide (V16-213), Floxuridine, 5-Fluorouracil (5-Fu), Flutamide, Hydroxyurea (hydroxycarbamide), Ifosfamide, Interferon Alpha-2a, Interferon Alpha-2b, Leuprolide acetate (LHRH-releasing factor analog), Lomustine, Mechlorethamine HCl (nitrogen mustard), Melphalan, Mercaptopurine, Mesna, Methotrexate (MTX), Mitomycin, Mitoxantrone HCl, Octreotide, Plicamycin, Procarbazine HCl, Streptozocin, Tamoxifen citrate, Thioguanine, Thiotepa, Vinblastine sulfate, Vincristine sulfate, Amsacrine, Azacitidine, Hexamethylmelamine, Interleukin-2, Mitoguazone, Pentostatin, Semustine, Teniposide, and Vindesine sulfate.

In addition, therapeutic compositions of the invention may be used for prophylactic treatment of cancer. There are hereditary conditions and/or environmental situations (e.g. exposure to carcinogens) known in the art that predispose an individual to developing cancers. Under these circumstances, it may be beneficial to treat these individuals with therapeutically effective doses of the polypeptide of the invention to reduce the risk of developing cancers.

In vitro models can be used to determine the effective doses of the polypeptide of the invention as a potential cancer treatment. These in vitro models include proliferation assays of cultured tumor cells, growth of cultured tumor cells in soft agar (see Freshney, (1987) Culture of Animal Cells: A Manual of Basic Technique, Wily-Liss, New York, N.Y. Ch 18 and Ch 21), tumor systems in nude mice as described in Giovanella et al., J. Nad. Can. Inst., 52: 921-30 (1974), mobility and invasive potential of tumor cells in Boyden Chamber assays as described in Pilkington et al., Anticancer Res., 17: 4107-9 (1997), and angiogenesis assays such as induction of vascularization of the chick chorioallantoic membrane or induction of vascular endothelial cell migration as described in Ribatta et al., Intl. J. Dev. Biol., 40: 1189-97 (1999) and Li et al., Clin. Exp. Metastasis, 17:423-9 (1999), respectively. Suitable tumor cells lines are available, e.g. from American Type Tissue Culture Collection catalogs.

4.7.11 Receptor/Ligand Activity

A polypeptide of the present invention may also demonstrate activity as receptor, receptor ligand or inhibitor or agonist of receptor/ligand interactions. A polynucleotide of the invention can encode a polypeptide exhibiting such characteristics. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as selectins, integrins and their ligands) and receptor/ligand pairs involved in antigen presentation, antigen recognition and development of cellular and humoral immune responses. Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity of a polypeptide of the invention may, among other means, be measured by the following methods:

Suitable assays for receptor-ligand activity include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 7.28, Measurement of Cellular Adhesion under static conditions 7.28.1-7.28.22), Takai et al., Proc. Natl. Acad. Sci. USA 84:6864-6868, 1987; Bierer et al., J. Exp. Med. 168:1145-1156, 1988; Rosenstein et al., J. Exp. Med. 169:149-160 1989; Stoltenborg et al., J. Immunol. Methods 175:59-68, 1994; Stitt et al., Cell 80:661-670, 1995.

By way of example, the polypeptides of the invention may be used as a receptor for a ligand(s) thereby transmitting the biological activity of that ligand(s). Ligands may be identified through binding assays, affinity chromatography, dihybrid screening assays, BIAcore assays, gel overlay assays, or other methods known in the art.

Studies characterizing drugs or proteins as agonist or antagonist or partial agonists or a partial antagonist require the use of other proteins as competing ligands. The polypeptides of the present invention or ligand(s) thereof may be labeled by being coupled to radioisotopes, colorimetric molecules or a toxin molecules by conventional methods. ("Guide to Protein Purification" Murray P. Deutscher (ed) Methods in Enzymology Vol. 182 (1990) Academic Press, Inc. San Diego). Examples of radioisotopes include, but are not limited to, tritium and carbon-14. Examples of colorimetric molecules include, but are not limited to, fluorescent molecules such as fluorescamine, or rhodamine or other colorimetric molecules. Examples of toxins include, but are not limited, to ricin.

4.7.12 Drug Screening

This invention is particularly useful for screening chemical compounds by using the novel polypeptides or binding fragments thereof in any of a variety of drug screening techniques. The polypeptides or fragments employed in such a test may either be free in solution, affixed to a solid support, borne on a cell surface or located intracellularly. One method of drug screening utilizes eukaryotic or prokaryotic host cells which are stably transformed with recombinant nucleic acids expressing the polypeptide or a fragment thereof. Drugs are screened against such transformed cells in competitive binding assays. Such cells, either in viable or fixed form, can be used for standard binding assays. One may measure, for example, the formation of complexes between polypeptides of the invention or fragments and the agent being tested or examine the diminution in complex formation between the novel polypeptides and an appropriate cell line, which are well known in the art.

Sources for test compounds that may be screened for ability to bind to or modulate (i.e., increase or decrease) the activity of polypeptides of the invention include (1) inorganic and organic chemical libraries, (2) natural product libraries, and (3) combinatorial libraries comprised of either random or mimetic peptides, oligonucleotides or organic molecules.

Chemical libraries may be readily synthesized or purchased from a number of commercial sources, and may include structural analogs of known compounds or compounds that are identified as "hits" or "leads" via natural product screening.

The sources of natural product libraries are microorganisms (including bacteria and fungi), animals, plants or other vegetation, or marine organisms, and libraries of mixtures for screening may be created by: (1) fermentation and extraction of broths from soil, plant or marine microorganisms or (2) extraction of the organisms themselves. Natural product libraries include polyketides, non-ribosomal peptides, and (non-naturally occurring) variants thereof. For a review, see *Science* 282:63-68 (1998).

Combinatorial libraries are composed of large numbers of peptides, oligonucleotides or organic compounds and can be readily prepared by traditional automated synthesis methods, PCR, cloning or proprietary synthetic methods. Of particular interest are peptide and oligonucleotide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, *Curr. Opin. Biotechnol.* 8:701-707 (1997). For reviews and examples of peptidomimetic libraries, see Al-Obeidi et al.,

*Mol. Biotechnol*, 9(3):205-23 (1998); Hruby et al., *Curr Opin Chem Biol*, 1(1): 114-19 (1997); Dorner et al., *Bioorg Med Chem*, 4(5):709-15 (1996) (alkylated dipeptides).

Identification of modulators through use of the various libraries described herein permits modification of the candidate "hit" (or "lead") to optimize the capacity of the "hit" to bind a polypeptide of the invention. The molecules identified in the binding assay are then tested for antagonist or agonist activity in in vivo tissue culture or animal models that are well known in the art. In brief, the molecules are titrated into a plurality of cell cultures or animals and then tested for either cell/animal death or prolonged survival of the animal/cells.

The binding molecules thus identified may be complexed with toxins, e.g., ricin or cholera, or with other compounds that are toxic to cells such as radioisotopes. The toxin-binding molecule complex is then targeted to a tumor or other cell by the specificity of the binding molecule for a polypeptide of the invention. Alternatively, the binding molecules may be complexed with imaging agents for targeting and imaging purposes.

4.7.13 Assay for Receptor Activity

The invention also provides methods to detect specific binding of a polypeptide e.g. a ligand or a receptor. The art provides numerous assays particularly useful for identifying previously unknown binding partners for receptor polypeptides of the invention. For example, expression cloning using mammalian or bacterial cells, or dihybrid screening assays can be used to identify polynucleotides encoding binding partners. As another example, affinity chromatography with the appropriate immobilized polypeptide of the invention can be used to isolate polypeptides that recognize and bind polypeptides of the invention. There are a number of different libraries used for the identification of compounds, and in particular small molecules, that modulate (i.e., increase or decrease) biological activity of a polypeptide of the invention. Ligands for receptor polypeptides of the invention can also be identified by adding exogenous ligands, or cocktails of ligands to two cells populations that are genetically identical except for the expression of the receptor of the invention: one cell population expresses the receptor of the invention whereas the other does not. The response of the two cell populations to the addition of ligands(s) are then compared. Alternatively, an expression library can be co-expressed with the polypeptide of the invention in cells and assayed for an autocrine response to identify potential ligand(s). As still another example, BIAcore assays, gel overlay assays, or other methods known in the art can be used to identify binding partner polypeptides, including, (1) organic and inorganic chemical libraries, (2) natural product libraries, and (3) combinatorial libraries comprised of random peptides, oligonucleotides or organic molecules.

The role of downstream intracellular signaling molecules in the signaling cascade of the polypeptide of the invention can be determined. For example, a chimeric protein in which the cytoplasmic domain of the polypeptide of the invention is fused to the extracellular portion of a protein, whose ligand has been identified, is produced in a host cell. The cell is then incubated with the ligand specific for the extracellular portion of the chimeric protein, thereby activating the chimeric receptor. Known downstream proteins involved in intracellular signaling can then be assayed for expected modifications i.e. phosphorylation. Other methods known to those in the art can also be used to identify signaling molecules involved in receptor activity.

4.7.14 Leukemias

Leukemias and related disorders may be treated or prevented by administration of a therapeutic that promotes or inhibits function of the polynucleotides and/or polypeptides of the invention. Such leukemias and related disorders include but are not limited to acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia and chronic lymphocytic leukemia (for a review of such disorders, see Fishman et al., 1985, Medicine, 2d Ed., J.B. Lippincott Co., Philadelphia).

4.7.15 Nervous System Disorders

Nervous system disorders, involving cell types which can be tested for efficacy of intervention with compounds that modulate the activity of the polynucleotides and/or polypeptides of the invention, and which can be treated upon thus observing an indication of therapeutic utility, include but are not limited to nervous system injuries, and diseases or disorders which result in either a disconnection of axons, a diminution or degeneration of neurons, or demyelination. Nervous system lesions which may be treated in a patient (including human and non-human mammalian patients) according to the invention include but are not limited to the following lesions of either the central (including spinal cord, brain) or peripheral nervous systems:

(i) traumatic lesions, including lesions caused by physical injury or associated with surgery, for example, lesions which sever a portion of the nervous system, or compression injuries;

(ii) ischemic lesions, in which a lack of oxygen in a portion of the nervous system results in neuronal injury or death, including cerebral infarction or ischemia, or spinal cord infarction or ischemia;

(iii) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis;

(iv) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis;

(v) lesions associated with nutritional diseases or disorders, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(vi) neurological lesions associated with systemic diseases including but not limited to diabetes (diabetic neuropathy, Bell's palsy), systemic lupus erythematosus, carcinoma, or sarcoidosis;

(vii) lesions caused by toxic substances including alcohol, lead, or particular neurotoxins; and (viii) demyelinated lesions in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

Therapeutics which are useful according to the invention for treatment of a nervous system disorder may be selected by testing for biological activity in promoting the survival or differentiation of neurons. For example, and not by way of limitation, therapeutics which elicit any of the following effects may be useful according to the invention:

(i) increased survival time of neurons in culture;

(ii) increased sprouting of neurons in culture or in vivo;

(iii) increased production of a neuron-associated molecule in culture or in vivo, e.g., choline acetyltransferase or acetylcholinesterase with respect to motor neurons; or (iv) decreased symptoms of neuron dysfunction in vivo.

Such effects may be measured by any method known in the art. In preferred, non-limiting embodiments, increased survival of neurons may be measured by the method set forth in Arakawa et al. (1990, J. Neurosci. 10:3507-3515); increased sprouting of neurons may be detected by methods set forth in Pestronk et al. (1980, Exp. Neurol. 70:65-82) or Brown et al. (1981, Ann. Rev. Neurosci. 4:17-42); increased production of neuron-associated molecules may be measured by bioassay, enzymatic assay, antibody binding, Northern blot assay, etc., depending on the molecule to be measured; and motor neuron dysfunction may be measured by assessing the physical manifestation of motor neuron disorder, e.g., weakness, motor neuron conduction velocity, or functional disability.

In specific embodiments, motor neuron disorders that may be treated according to the invention include but are not limited to disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including but not limited to progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

4.7.16 Other Activities

A polypeptide of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or circadian cycles or rhythms; effecting the fertility of male or female subjects; effecting the metabolism, catabolism, anabolism, processing, utilization, storage or elimination of dietary fat, lipid, protein, carbohydrate, vitamins, minerals, co-factors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

4.7.17 Identification of Polymorphisms

The demonstration of polymorphisms makes possible the identification of such polymorphisms in human subjects and the pharmacogenetic use of this information for diagnosis and treatment. Such polymorphisms may be associated with, e.g., differential predisposition or susceptibility to various disease states (such as disorders involving inflammation or immune response) or a differential response to drug administration, and this genetic information can be used to tailor preventive or therapeutic treatment appropriately. For example, the existence of a polymorphism associated with a predisposition to inflammation or autoimmune disease makes possible the diagnosis of this condition in humans by identifying the presence of the polymorphism.

Polymorphisms can be identified in a variety of ways known in the art which all generally involve obtaining a sample from a patient, analyzing DNA from the sample, optionally involving isolation or amplification of the DNA, and identifying the presence of the polymorphism in the DNA. For example, PCR may be used to amplify an appropriate fragment of genomic DNA which may then be sequenced. Alternatively, the DNA may be subjected to allele-specific oligonucleotide hybridization (in which appropriate oligonucleotides are hybridized to the DNA under conditions permitting detection of a single base mismatch) or to a single nucleotide extension assay (in which an oligonucleotide that hybridizes immediately adjacent to the position of the polymorphism is extended with one or more labeled nucleotides). In addition, traditional restriction fragment length polymorphism analysis (using restriction enzymes that provide differential digestion of the genomic DNA depending on the presence or absence of the polymorphism) may be performed. Arrays with nucleotide sequences of the present invention can be used to detect polymorphisms. The array can comprise modified nucleotide sequences of the present invention in order to detect the nucleotide sequences of the present invention. In the alternative, any one of the nucleotide sequences of the present invention can be placed on the array to detect changes from those sequences.

Alternatively a polymorphism resulting in a change in the amino acid sequence could also be detected by detecting a corresponding change in amino acid sequence of the protein, e.g., by an antibody specific to the variant sequence.

4.7.18 Arthritis and Inflammation

The immunosuppressive effects of the compositions of the invention against rheumatoid arthritis is determined in an experimental animal model system. The experimental model system is adjuvant induced arthritis in rats, and the protocol is described by J. Holoshitz, et al., 1983, Science, 219:56, or by B. Waksman et al., 1963, Int. Arch. Allergy Appl. Immunol., 23:129. Induction of the disease can be caused by a single injection, generally intradermally, of a suspension of killed *Mycobacterium tuberculosis* in complete Freund's adjuvant (CFA). The route of injection can vary, but rats may be injected at the base of the tail with an adjuvant mixture. The polypeptide is administered in phosphate buffered solution (PBS) at a dose of about 1-5 mg/kg. The control consists of administering PBS only.

The procedure for testing the effects of the test compound would consist of intradermally injecting killed *Mycobacterium tuberculosis* in CFA followed by immediately administering the test compound and subsequent treatment every other day until day 24. At 14, 15, 18, 20, 22, and 24 days after injection of *Mycobacterium* CFA, an overall arthritis score may be obtained as described by J. Holoskitz above. An analysis of the data would reveal that the test compound would have a dramatic affect on the swelling of the joints as measured by a decrease of the arthritis score.

4.8 Therapeutic Methods

The compositions (including polypeptide fragments, analogs, variants and antibodies or other binding partners or modulators including antisense polynucleotides) of the invention have numerous applications in a variety of therapeutic methods. Examples of therapeutic applications include, but are not limited to, those exemplified herein.

4.8.1 Example

One embodiment of the invention is the administration of an effective amount of the stem cell growth factor-like polypeptides or other composition of the invention to individuals affected by a disease or disorder that can be modulated by regulating the peptides of the invention. While the mode of administration is not particularly important, parenteral administration is preferred. An exemplary mode of administration is to deliver an intravenous bolus. The dosage of stem cell growth factor-like polypeptides or other composition of the invention will normally be determined by the prescribing physician. It is to be expected that the dosage will vary according to the age, weight, condition and response of the individual patient. Typically, the amount of polypeptide administered per dose will be in the range of about 0.01 µg/kg to 100 mg/kg of body weight, with the preferred dose being about 0.1 g4 kg to 10 mg/kg of patient body weight. For parenteral administration, stem cell growth factor-like polypeptides of the invention will be formulated in an injectable form combined with a pharmaceutically acceptable parenteral vehicle. Such vehicles are well known in the art and examples include water, saline, Ringer's solution, dextrose solution, and solutions consisting of small amounts of the human serum albumin. The vehicle may contain minor amounts of additives that maintain the isotonicity and stability of the polypeptide or other active ingredient. The preparation of such solutions is within the sldll of the art.

4.9 Pharmaceutical Formulations and Routes of Administration

A protein or other composition of the present invention (from whatever source derived, including without limitation from recombinant and non-recombinant sources and including antibodies and other binding partners of the polypeptides of the invention) may be administered to a patient in need, by itself, or in pharmaceutical compositions where it is mixed with suitable carriers or excipient(s) at doses to treat or ameliorate a variety of disorders. Such a composition may optionally contain (in addition to protein or other active ingredient and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IFN, TNF0, TNF1, TNF2, G-CSF, Meg-CSF, thrombopoietin, stem cell factor, and erythropoietin. In further compositions, proteins of the invention may be combined with other agents beneficial to the treatment of the disease or disorder in question. These agents include various growth factors such as epidermal growth factor (EGF), platelet-derived growth factor (PDGF), transforming growth factors (TGF-α and TGF-β), insulin-like growth factor (IGF), as well as cytokines described herein.

The pharmaceutical composition may further contain other agents which either enhance the activity of the protein or other active ingredient or complement its activity or use in treatment. Such additional factors and/or agents may be included in the pharmaceutical composition to produce a synergistic effect with protein or other active ingredient of the invention, or to minimize side effects. Conversely, protein or other active ingredient of the present invention may be included in formulations of the particular clotting factor, cytokine, lymphokine, other hematopoietic factor, thrombolytic or anti-thrombotic factor, or anti-inflammatory agent to minimize side effects of the clotting factor, cytokine, lymphokine, other hematopoietic factor, thrombolytic or anti-thrombotic factor, or anti-inflammatory agent (such as IL-1Ra, IL-1 Hy1, IL-1 Hy2, anti-TNF, corticosteroids, immunosuppressive agents). A protein of the present invention may be active in multimers (e.g., heterodimers or homodimers) or complexes with itself or other proteins. As a result, pharmaceutical compositions of the invention may comprise a protein of the invention in such multimeric or complexed form.

As an alternative to being included in a pharmaceutical composition of the invention including a first protein, a second protein or a therapeutic agent may be concurrently administered with the first protein (e.g., at the same time, or at differing times provided that therapeutic concentrations of the combination of agents is achieved at the treatment site). Techniques for formulation and administration of the compounds of the instant application may be found in "Remington's Pharmaceutical Sciences," Mack Publishing Co., Easton, Pa., latest edition. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient, administered alone, a therapeutically effective dose refers to that ingredient alone. When applied to a combination, a therapeutically effective dose refers to combined amounts of the active ingredients that result in the therapeutic effect, whether administered in combination, serially or simultaneously.

In practicing the method of treatment or use of the present invention, a therapeutically effective amount of protein or other active ingredient of the present invention is administered to a mammal having a condition to be treated. Protein or other active ingredient of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein or other active ingredient of the present invention may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering protein or other active ingredient of the present invention in combination with cytokine(s), lymphokine(s), other hematopoietic factor(s), thrombolytic or anti-thrombotic factors.

4.9.1 Routes of Administration

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration of protein or other active ingredient of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

Alternately, one may administer the compound in a local rather than systemic manner, for example, via injection of the compound directly into a arthritic joints or in fibrotic tissue, often in a depot or sustained release formulation. In order to prevent the scarring process frequently occurring as complication of glaucoma surgery, the compounds may be administered topically, for example, as eye drops. Furthermore, one may administer the drug in a targeted drug delivery system, for example, in a liposome coated with a specific antibody, targeting, for example, arthritic or fibrotic tissue. The liposomes will be targeted to and taken up selectively by the afflicted tissue.

The polypeptides of the invention are administered by any route that delivers an effective dosage to the desired site of action. The determination of a suitable route of administration and an effective dosage for a particular indication is within the level of skill in the art. Preferably for wound treatment, one administers the therapeutic compound directly to the site. Suitable dosage ranges for the polypeptides of the invention can be extrapolated from these dosages or from similar studies in appropriate animal models. Dosages can then be adjusted as necessary by the clinician to provide maximal therapeutic benefit.

4.9.2 Compositions/Formulations

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen. When a therapeutically effective amount of protein or other active ingredient of the present invention is administered orally, protein or other active ingredient of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein or other active ingredient of the present invention, and preferably from about 25 to 90% protein or other active ingredient of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein or other active ingredient of the present invention, and preferably from about 1 to 50% protein or other active ingredient of the present invention.

When a therapeutically effective amount of protein or other active ingredient of the present invention is administered by intravenous, cutaneous or subcutaneous injection, protein or other active ingredient of the present invention will be in the form of a pyrogen-free, parenterally acceptable aqueous solution. The preparation of such parenterally acceptable protein or other active ingredient solutions, having due regard to pH, isotonicity, stability, and the like, is within the still in the art. A preferred pharmaceutical composition for intravenous, cutaneous, or subcutaneous injection should contain, in addition to protein or other active ingredient of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the arL For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added All formulations for oral administration should be in dosages suitable for such administration. For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafiuoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a co-solvent system comprising benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5 W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose. Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein or other active ingredient stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Many of the active ingredients of the invention may be provided as salts with pharmaceutically compatible counter ions. Such pharmaceutically acceptable base addition salts are those salts which retain the biological effectiveness and properties of the free acids and which are obtained by reaction with inorganic or organic bases such as sodium hydroxide, magnesium hydroxide, ammonia, trialkylamine, dialkylamine, monoalkylamine, dibasic amino acids, sodium acetate, potassium benzoate, triethanol amine and the like.

The pharmaceutical composition of the invention may be in the form of a complex of the protein(s) or other active ingredient of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunoglobulin and other molecules on B cells as well as antibodies able to bind the TCR and other molecules on T cells can be combined with the pharmaceutical composition of the invention.

The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithins, phospholipids, saponin, bile acids, and the like. Preparation of Such Liposomal Formulations is within the Level of Skill in the Art, as Disclosed, for example, in U.S. Pat. Nos. 4,235,871; 4,501,728; 4,837,028; and 4,737,323, all of which are incorporated herein by reference.

The amount of protein or other active ingredient of the present invention in the pharmaceutical composition of the present invention will depend upon the nature and severity of the condition being treated, and on the nature of prior treatments which the patient has undergone. Ultimately, the attending physician will decide the amount of protein or other active ingredient of the present invention with which to treat each individual patient. Initially, the attending physician will administer low doses of protein or other active ingredient of the present invention and observe the patient's response. Larger doses of protein or other active ingredient of the present invention may be administered until the optimal therapeutic effect is obtained for the patient, and at that point the dosage is not increased further. It is contemplated that the various pharmaceutical compositions used to practice the method of the present invention should contain about 0.01 µg to about 100 mg (preferably about 0.1 µg to about 10 mg, more preferably about 0.1 µg to about 1 mg) of protein or other active ingredient of the present invention per kg body weight. For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein or other active ingredient of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing or other active ingredient-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalcium phosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability. Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as allylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5-20 wt %, preferably 1-10 wt % based on total formulation weight, which represents the amount necessary to prevent desorption of the protein from the polymer matrix and to provide appropriate handling of the composition, yet not so much that the progenitor cells are prevented from infiltrating the matrix, thereby providing the protein the opportunity to assist the osteogenic activity of the progenitor cells. In further compositions, proteins or other active ingredient of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-α and TGF-β), and insulin-like growth factor (IGF).

The therapeutic compositions are also presently valuable for veterinary applications. Particularly domestic animals and thoroughbred horses, in addition to humans, are desired patients for such treatment with proteins or other active ingredient of the present invention. The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA). Cells may also be cultured ex vivo in the presence of proteins of the present invention in order to proliferate or to produce a desired effect on or activity in such cells. Treated cells can then be introduced in vivo for therapeutic purposes.

4.9.3 Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amount is well within the capability of those skilled in the art, especially in light of the detailed disclosure provided herein. For any compound used in the method of the invention, the therapeutically effective dose can be estimated initially from appropriate in vitro assays. For example, a dose can be formulated in animal models to achieve a circulating concentration range that can be used to more accurately determine useful doses in humans. For example, a dose can be formulated in animal models to achieve a circulating concentration range that includes the $IC_{50}$ as determined in cell culture (i.e., the concentration of the test compound which achieves a half-maximal inhibition of the protein's biological activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. See, e.g., Fingl et al., 1975, in "The Pharmacological Basis of Therapeutics", Ch. 1 p.1. Dosage amount and interval may be adjusted individually to provide plasma levels of the active moiety which are sufficient to maintain the desired effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

An exemplary dosage regimen for polypeptides or other compositions of the invention will be in the range of about 0.01 μg/kg to 100 mg/kg of body weight daily, with the preferred dose being about 0.1 μg/kg to 25 mg/kg of patient body weight daily, varying in adults and children. Dosing may be once daily, or equivalent doses may be delivered at longer or shorter intervals.

The amount of composition administered will, of course, be dependent on the subject being treated, on the subject's age and weight, the severity of the affliction, the manner of administration and the judgment of the prescribing physician.

4.9.4 Packaging

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

4.10 Antibodies 4.10.1 Human Antibodies

Fully human antibodies relate to antibody molecules in which essentially the entire sequences of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized in the practice of the present invention and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries (Hoogenboom and Winter, *J. Mol. Biol.*, 227:381 (1991); Marks et al., *J. Mol. Biol.*, 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (*Bio/Technology* 10, 779-783 (1992)); Lonberg et al. (*Nature* 368 856-859 (1994)); Morrison (*Nature* 368, 812-13 (1994)); Fishwild et al, (*Nature Biotechnology* 14, 845-51 (1996)); Neuberger (*Nature Biotechnology* 14, 826 (1996)); and Lonberg and Huszar (*Intern. Rev. Immunol.* 13 65-93 (1995)).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker, and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

4.10.2 Fab Fragments and Single Chain Antibodies

According to the invention, techniques can be adapted for the production of single-chain antibodies specific to an antigenic protein of the invention (see e.g., U.S. Pat. No. 4,946, 778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

4.10.3 Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit.

Methods for making bispecific antibodies are known in the art Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., 1991 EMBO J., 10:3655-3659.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavychain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full-length antibodies or antibody fragments (e.g. $F_{(ab')2}$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from E. coli and chemically coupled to form bispecific antibodies. Shalaby et al., J. Exp. Med. 175:217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD 16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

4.10.4 Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

4.10.5 Effector Function Engineering

It can be desirable to modify the antibody of the invention with respect to effector function, so as to enhance, e.g., the effectiveness of the antibody in treating cancer. For example, cysteine residue(s) can be introduced into the Pc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., J. Exp Med., 176: 1191-1195 (1992) and Shopes, J. Immunol., 148: 2918-2922 (1992). Homodimeric antibodies with enhanced anti-tumor activity can also be prepared using heterobifunctional cross-linkers as described in Wolff et al. Cancer Research, 53: 2560-2565 (1993). Alternatively, an antibody can be engineered that has dual Fc regions and can thereby have enhanced complement lysis and ADCC capabilities. See Stevenson et al., Anti-Cancer Drug Design, 3: 219-230 (1989).

4.10.6 Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody can be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is in turn conjugated to a cytotoxic agent.

4.11 Computer Readable Sequences

In one application of this embodiment, a nucleotide sequence of the present invention can be recorded on computer readable media. As used herein, "computer readable media" refers to any medium which can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention. As used herein, "recorded" refers to a process for storing information on computer readable medium. A skilled artisan can readily adopt any of the presently known methods for recording information on computer readable medium to generate manufactures comprising the nucleotide sequence information of the present invention.

A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of data processor structuring formats (e.g. text file or database) in order to obtain computer readable medium having recorded thereon the nucleotide sequence information of the present invention.

By providing any of the nucleotide sequences SEQ ID NO: 1-2, 4, 8, 10, 12, 14, 16-17, 19, or 26 or a representative fragment thereof; or a nucleotide sequence at least 95% identical to any of the nucleotide sequences of SEQ ID NO: 1-2, 4, 8, 10, 12, 14, 16-17, 19, or 26 in computer readable form, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., J. Mol. Biol. 215: 403-410 (1990)) and BLAZE (Brutlag et al., Comp. Chem. 17:203-207 (1993)) search algorithms on a Sybase system is used to identify open reading frames (ORFs) within a nucleic acid sequence. Such ORFs may be protein encoding fragments and may be useful in producing commercially important proteins such as enzymes used in fermentation reactions and in the production of commercially useful metabolites.

As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based systems are suitable for use in the present invention. As stated above, the computer-based systems of the present invention comprise a data storage means having stored therein a nucleotide sequence of the present invention and the necessary hardware means and software means for supporting and implementing a search means. As used herein, "data storage means" refers to memory which can store nucleotide sequence information of the present invention, or a memory access means which can access manufactures having recorded thereon the nucleotide sequence information of the present invention.

As used herein, "search means" refers to one or more programs which are implemented on the computer-based system to compare a target sequence or target structural motif with the sequence information stored within the data storage means. Search means are used to identify fragments or regions of a known sequence which match a particular target sequence or target motif. A variety of known algorithms are disclosed publicly and a variety of commercially available software for conducting search means are and can be used in the computer-based systems of the present invention. Examples of such software includes, but is not limited to, Smith-Waterman, MacPattern (EMBL), BLASTN and BLASTA (NPOLYPEPTIDEIA). A skilled artisan can readily recognize that any one of the available algorithms or implementing software packages for conducting homology searches can be adapted for use in the present computer-based systems. As used herein, a "target sequence" can be any nucleic acid or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids, or from about 30 to 300 nucleotide residues. However, it is well recognized that searches for commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based upon a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

4.12 Triple Helix Formation

In addition, the fragments of the present invention, as broadly described, can be used to control gene expression through triple helix formation or antisense DNA or RNA, both of which methods are based on the binding of a polynucleotide sequence to DNA or RNA. Polynucleotides suitable for use in these methods are usually 20 to 40 bases in length and are designed to be complementary to a region of the gene involved in transcription (triple helix—see Lee et al., Nucl. Acids Res. 6:3073 (1979); Cooney et al., Science 15241:456 (1988); and Dervan et al., Science 251:1360 (1991)) or to the mRNA itself (antisense—Olmmo, J. Neurochem. 56:560 (1991); Oligodeoxynucleotides as Antisense Ihibitors of Gene Expression, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide.

4.13 Diagnostic Assays and Kits

The present invention further provides methods to identify the presence or expression of one of the ORFs of the present invention, or homolog thereof, in a test sample, using a nucleic acid probe or antibodies of the present invention, optionally conjugated or otherwise associated with a suitable label.

In general, methods for detecting a polynucleotide of the invention can comprise contacting a sample with a compound that binds to and forms a complex with the polynucleotide for a period sufficient to form the complex, and detecting the complex, so that if a complex is detected, a polynucleotide of the invention is detected in the sample. Such methods can also comprise contacting a sample under stringent hybridization conditions with nucleic acid primers that anneal to a polynucleotide of the invention under such conditions, and amplifying annealed polynucleotides, so that if a polynucleotide is amplified, a polynucleotide of the invention is detected in the sample.

In general, methods for detecting a polypeptide of the invention can comprise contacting a sample with a compound that binds to and forms a complex with the polypeptide for a period sufficient to form the complex, and detecting the complex, so that if a complex is detected, a polypeptide of the invention is detected in the sample.

In detail, such methods comprise incubating a test sample with one or more of the antibodies or one or more of the nucleic acid probes of the present invention and assaying for binding of the nucleic acid probes or antibodies to components within the test sample.

Conditions for incubating a nucleic acid probe or antibody with a test sample vary. Incubation conditions depend on the format employed in the assay, the detection methods employed, and the type and nature of the nucleic acid probe or antibody used in the assay. One skilled in the art will recognize that any one of the commonly available hybridization, amplification or immunological assay formats can readily be adapted to employ the nucleic acid probes or antibodies of the present invention. Examples of such assays can be found in Chard, T., An Introduction to Radioimmunoassay and Related Techniques, Elsevier Science Publishers, Amsterdam, The Netherlands (1986); Bullock, G. R. et al., Techniques in Immunocytochemistry, Academic Press, Orlando, Fla. Vol. 1 (1982), Vol. 2 (1983), Vol. 3 (1985); Tijssen, P., Practice and Theory of immunoassays: Laboratory Techniques in Biochemistry and Molecular Biology, Elsevier Science Publishers, Amsterdam, The Netherlands (1985). The test samples of the present invention include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is compatible with the system utilized.

In another embodiment of the present invention, kits are provided which contain the necessary reagents to carry out the assays of the present invention. Specifically, the invention provides a compartment kit to receive, in close confinement, one or more containers which comprises: (a) a first container comprising one of the probes or antibodies of the present invention; and (b) one or more other containers comprising one or more of the following: wash reagents, reagents capable of detecting presence of a bound probe or antibody.

In detail, a compartment kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody or probe. Types of detection reagents include labeled nucleic acid probes, labeled secondary antibodies, or in the alternative, if the primary antibody is labeled, the enzymatic, or antibody binding reagents which are capable of reacting with the labeled antibody. One skilled in the art will readily recognize that the disclosed probes and antibodies of the present invention can be readily incorporated into one of the established kit formats which are well known in the art.

4.14 Medical Imaging

The novel polypeptides and binding partners of the invention are useful in medical imaging of sites expressing the molecules of the invention (e.g., where the polypeptide of the invention is involved in the immune response, for imaging sites of inflammation or infection). See, e.g., Kunkel et al., U.S. Pat. No. 5,413,778. Such methods involve chemical attachment of a labeling or imaging agent, administration of the labeled polypeptide to a subject in a pharmaceutically acceptable carrier, and imaging the labeled polypeptide in vivo at the target site.

4.15 Screening Assays

Using the isolated proteins and polynucleotides of the invention, the present invention further provides methods of obtaining and identifying agents which bind to a polypeptide encoded by an ORF corresponding to any of the nucleotide sequences set forth in SEQ ID NO: 1-2, 4, 8, 10, 12, 14, 16-17, 19, or 26, or bind to a specific domain of the polypeptide encoded by the nucleic acid. In detail, said method comprises the steps of:

(a) contacting an agent with an isolated protein encoded by an ORF of the present invention, or nucleic acid of the invention; and (b) determining whether the agent binds to said protein or said nucleic acid.

In general, therefore, such methods for identifying compounds that bind to a polynucleotide of the invention can comprise contacting a compound with a polynucleotide of the invention for a time sufficient to form a polynucleotide/compound complex, and detecting the complex, so that if a polynucleotide/compound complex is detected, a compound that binds to a polynucleotide of the invention is identified.

Likewise, in general, therefore, such methods for identifying compounds that bind to a polypeptide of the invention can comprise contacting a compound with a polypeptide of the invention for a time sufficient to form a polypeptide/compound complex, and detecting the complex, so that if a polypeptide/compound complex is detected, a compound that binds to a polynucleotide of the invention is identified.

Methods for identifying compounds that bind to a polypeptide of the invention can also comprise contacting a compound with a polypeptide of the invention in a cell for a time sufficient to form a polypeptide/compound complex, wherein the complex drives expression of a receptor gene sequence in the cell, and detecting the complex by detecting reporter gene sequence expression, so that if a polypeptide/compound complex is detected, a compound that binds a polypeptide of the invention is identified.

Compounds identified via such methods can include compounds which modulate the activity of a polypeptide of the invention (that is, increase or decrease its activity, relative to activity observed in the absence of the compound). Alternatively, compounds identified via such methods can include compounds which modulate the expression of a polynucleotide of the invention (that is, increase or decrease expression relative to expression levels observed in the absence of the compound). Compounds, such as compounds identified via the methods of the invention, can be tested using standard assays well known to those of skill in the art for their ability to modulate activity/expression.

The agents screened in the above assay can be, but are not limited to, peptides, carbohydrates, vitamin derivatives, or other pharmaceutical agents. The agents can be selected and screened at random or rationally selected or designed using protein modeling techniques.

For random screening, agents such as peptides, carbohydrates, pharmaceutical agents and the like are selected at random and are assayed for their ability to bind to the protein encoded by the ORF of the present invention. Alternatively, agents may be rationally selected or designed. As used herein, an agent is said to be "rationally selected or designed" when the agent is chosen based on the configuration of the particular protein. For example, one skilled in the art can readily adapt currently available procedures to generate peptides, pharmaceutical agents and the like, capable of binding to a specific peptide sequence, in order to generate rationally designed antipeptide peptides, for example see Hurby et al., Application of Synthetic Peptides: Antisense Peptides," In Synthetic Peptides, A User's Guide, W. H. Freeman, NY (1992), pp. 289-307, and Kaspczak et al., Biochemistry 28:9230-8 (1989), or pharmaceutical agents, or the like.

In addition to the foregoing, one class of agents of the present invention, as broadly described, can be used to control gene expression through binding to one of the ORFs or EMFs of the present invention. As described above, such agents can be randomly screened or rationally designed/selected. Targeting the ORF or EMF allows a skilled artisan to design sequence specific or element specific agents, modulating the expression of either a single ORF or multiple ORFs which rely on the same EMF for expression control. One class of DNA binding agents are agents which contain base residues which hybridize or form a triple helix formation by binding to DNA or RNA. Such agents can be based on the classic phosphodiester, ribonucleic acid backbone, or can be a variety of sulfhydryl or polymeric derivatives which have base attachment capacity.

Agents suitable for use in these methods usually contain 20 to 40 bases and are designed to be complementary to a region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxynucleotides as Antisense inhibitors of Gene Expression, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide and other DNA binding agents.

Agents which bind to a protein encoded by one of the ORFs of the present invention can be used as a diagnostic agent Agents which bind to a protein encoded by one of the ORFs of the present invention can be formulated using known techniques to generate a pharmaceutical composition.

4.16 Use of Nucleic Acids as Probes

Another aspect of the subject invention is to provide for polypeptide-specific nucleic acid hybridization probes capable of hybridizing with naturally occurring nucleotide sequences. The hybridization probes of the subject invention may be derived from any of the nucleotide sequences SEQ ID NO: 1-2, 4, 8, 10, 12, 14, 16-17, 19, or 26. Because the corresponding gene is only expressed in a limited number of tissues, a hybridization probe derived from of any of the nucleotide sequences SEQ ID NO: 1-2, 4, 8, 10, 12, 14, 16, 17, 19, or 26 can be used as an indicator of the presence of RNA of cell type of such a tissue in a sample.

Any suitable hybridization technique can be employed, such as, for example, in situ hybridization. PCR as described in U.S. Pat. Nos. 4,683,195 and 4,965,188 provides additional uses for oligonucleotides based upon the nucleotide sequences. Such probes used in PCR may be of recombinant origin, may be chemically synthesized, or a mixture of both. The probe will comprise a discrete nucleotide sequence for the detection of identical sequences or a degenerate pool of possible sequences for identification of closely related genomic sequences.

Other means for producing specific hybridization probes for nucleic acids include the cloning of nucleic acid sequences into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides. The nucleotide sequences may be used to construct hybridization probes for mapping their respective genomic sequences. The nucleotide sequence provided herein may be mapped to a chromosome or specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes: A Manual of Basic Techniques, Pergamon Press, New York N.Y.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a nucleic acid on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

4.17 Preparation of Support Bound Oligonucleotides

Oligonucleotides, i.e., small nucleic acid segments, may be readily prepared by, for example, directly synthesizing the oligonucleotide by chemical means, as is commonly practiced using an automated oligonucleotide synthesizer.

Support bound oligonucleotides may be prepared by any of the methods known to those of skill in the art using any suitable support such as glass, polystyrene or Teflon. One strategy is to precisely spot oligonucleotides synthesized by standard synthesizers. Immobilization can be achieved using passive adsorption (Inouye & Hondo, 1990 J. Clin Microbiol 28(6) 1462-72); using UV light (Nagata et al., 1985; Dahlen et al., 1987; Morrissey & Collins, Mol. Cell. Probes 1989 3(2) 189-207) or by covalent binding of base modified DNA (Keller et al., 1988; 1989); all references being specifically incorporated herein.

Another strategy that may be employed is the use of the strong biotin-streptavidin interaction as a linker. For example, Broude et al. (1994) Proc. Natl. Acad. Sci. USA 91(8) 3072-6 describe the use of biotinylated probes, although these are duplex probes, that are immobilized on streptavidin-coated magnetic beads. Streptavidin-coated beads may be purchased from Dynal, Oslo. Of course, this same linking chemistry is applicable to coating any surface with streptavidin. Biotinylated probes may be purchased from various sources, such as, e.g., Operon Technologies (Alameda, Calif.).

Nunc Laboratories (Naperville, Ill.) is also selling suitable material that could be used. Nunc Laboratories have developed a method by which DNA can be covalently bound to the microwell surface termed Covalink NH. Covalink NH is a polystyrene surface grafted with secondary amino groups (>NH) that serve as bridge-heads for further covalent coupling. CovaLink Modules may be purchased from Nunc Laoratories. DNA molecules may be bound to CovaLink exclusively at the 5'-end by a phosphoramidate bond, allowing immobilization of more than 1 μmol of DNA (Rasmussen et al, (1991) Anal Biochem 198(1) 13842.

The use of CovaLink NH strips for covalent binding of DNA molecules at the 5'-end has been described (Rasmussen et al., 1991). In this technology, a phosphoramidate bond is employed (Chu et al., 1983 Nucleic Acids 11(18) 6513-29). This is beneficial as immobilization using only a single covalent bond is preferred. The phosphoramidate bond joins the DNA to the CovaLink NH secondary amino groups that are positioned at the end of spacer arms covalently grafted onto the polystyrene surface through a 2 nm long spacer arm. To link an oligonucleotide to CovaLink NH via an phosphoramidate bond, the oligonucleotide terminus must have a 5'-end phosphate group. It is, perhaps, even possible for biotin to be covalently bound to CovaLink and then streptavidin used to bind the probes.

More specifically, the linkage method includes dissolving DNA in water (7.5 ng/ul) and denaturing for 10 min. at 95° C.

and cooling on ice for 10 min. Ice-cold 0.1 M 1-methylimidazole, pH 7.0 (1-MeIm$_7$), is then added to a final concentration of 10 mM 1-MeIm$_7$. A ss DNA solution is then dispensed into CovaLink NH strips (75 ul/well) standing on ice.

Carbodiimide 0.2 M 1-ethyl-3-(3-dimethylaminopropyl)-carbodiimide (EDC), dissolved in 10 mM 1-MeIm$_7$, is made fresh and 25 ul added per well. The strips are incubated for 5 hours at 50° C. After incubation the strips are washed using, e.g., Nunc-Immuno Wash; first the wells are washed 3 times, then they are soaked with washing solution for 5 min., and finally they are washed 3 times (where in the washing solution is 0.4 N NaOH, 0.25% SDS heated to 50° C.).

It is contemplated that a further suitable method for use with the present invention is that described in PCT Patent Application WO 90/03382 (Southern & Maskos), incorporated herein by reference. This method of preparing an oligonucleotide bound to a support involves attaching a nucleoside 3'-reagent through the phosphate group by a covalent phosphodiester link to aliphatic hydroxyl groups carried by the support. The oligonucleotide is then synthesized on the supported nucleoside and protecting groups removed from the synthetic oligonucleotide chain under standard conditions that do not cleave the oligonucleotide from the support. Suitable reagents include nucleoside phosphoramidite and nucleoside hydrogen phosphorate.

An on-chip strategy for the preparation of DNA probe for the preparation of DNA probe arrays may be employed. For example, addressable laser-activated photodeprotection may be employed in the chemical synthesis of oligonucleotides directly on a glass surface, as described by Fodor et al. (1991) Science 251(4995) 767-73, incorporated herein by reference. Probes may also be immobilized on nylon supports as described by Van Ness et al. (1991) Nucleic Acids Res. 19(12) 3345-50; or linked to Teflon using the method of Duncan & Cavalier (1988) Anal Biochem 169(1) 104-8; all references being specifically incorporated herein.

To link an oligonucleotide to a nylon support, as described by Van Ness et al. (1991), requires activation of the nylon surface via alkylation and selective activation of the 5'-amine of oligonucleotides with cyanuric chloride.

One particular way to prepare support bound oligonucleotides is to utilize the light-generated synthesis described by Pease et al, (1994) Proc. Natl. Acad. Sci. USA 91(11) 5022-6. These authors used current photolithographic techniques to generate arrays of immobilized oligonucleotide probes (DNA chips). These methods, in which light is used to direct the synthesis of oligonucleotide probes in high-density, miniaturized arrays, utilize photolabile 5'-protected N-acyl-deoxynucleoside phosphoramidites, surface linker chemistry and versatile combinatorial synthesis strategies. A matrix of 256 spatially defined oligonucleotide probes may be generated in this manner.

4.18 Preparation of Nucleic Acid Fragments

The nucleic acids may be obtained from any appropriate source, such as cDNAs, genomic DNA, chromosomal DNA, microdissected chromosome bands, cosmid or YAC inserts, and RNA, including mRNA without any amplification steps. For example, Sambrook et al. (1989) describes three protocols for the isolation of high molecular weight DNA from mammalian cells (p. 9.14-9.23).

DNA fragments may be prepared as clones in M13, plasmid or lambda vectors and/or prepared directly from genomic DNA or cDNA by PCR or other amplification methods. Samples may be prepared or dispensed in multiwell plates. About 100-1000 ng of DNA samples may be prepared in 2-500 ml of final volume.

The nucleic acids would then be fragmented by any of the methods known to those of skill in the art including, for example, using restriction enzymes as described at 9.24-9.28 of Sambrook et al (1989), shearing by ultrasound and NaOH treatment Low pressure shearing is also appropriate, as described by Schriefer et al. (1990) Nucleic Acids Res. 18(24) 7455-6. In this method, DNA samples are passed through a small French pressure cell at a variety of low to intermediate pressures. A lever device allows controlled application of low to intermediate pressures to the cell. The results of these studies indicate that low-pressure shearing is a useful alternative to sonic and enzymatic DNA fragmentation methods.

One particularly suitable way for fragmenting DNA is contemplated to be that using the two base recognition endonuclease, CviJI, described by Fitzgerald et al. (1992) Nucleic Acids Res. 20(14) 3753-62. These authors described an approach for the rapid fragmentation and fractionation of DNA into particular sizes that they contemplated to be suitable for shotgun cloning and sequencing.

The restriction endonuclease CviJI normally cleaves the recognition sequence PuGCPy between the G and C to leave blunt ends. Atypical reaction conditions, which alter the specificity of this enzyme (CviJI), yield a quasi-random distribution of DNA fragments form the small molecule pUC19 (2688 base pairs). Fitzgerald et al. (1992) quantitatively evaluated the randomness of this fragmentation strategy, using a CviJI digest of pUC19 that was size fractionated by a rapid gel filtration method and directly ligated, without end repair, to a lac Z minus M13 cloning vector. Sequence analysis of 76 clones showed that CviJI** restricts pyGCPy and PuGCPu, in addition to PuGCPy sites, and that new sequence data is accumulated at a rate consistent with random fragmentation.

As reported in the literature, advantages of this approach compared to sonication and agarose gel fractionation include: smaller amounts of DNA are required (0.2-0.5 ug instead of 2-5 ug); and fewer steps are involved (no preligation, end repair, chemical extraction, or agarose gel electrophoresis and elution are needed).

Irrespective of the manner in which the nucleic acid fragments are obtained or prepared, it is important to denature the DNA to give single stranded pieces available for hybridization. This is achieved by incubating the DNA solution for 2-5 minutes at 80-90° C. The solution is then cooled quickly to 2° C. to prevent renaturation of the DNA fragments before they are contacted with the chip. Phosphate groups must also be removed from genomic DNA by methods known in the art 4.19 Preparation of DNA Arrays Arrays may be prepared by spotting DNA samples on a support such as a nylon membrane. Spotting may be performed by using arrays of metal pins (the positions of which correspond to an array of wells in a microtiter plate) to repeated by transfer of about 20 nl of a DNA solution to a nylon membrane. By offset printing, a density of dots higher than the density of the wells is achieved. One to 25 dots may be accommodated in 1 m$^2$, depending on the type of label used. By avoiding spotting in some preselected number of rows and columns, separate subsets (subarrays) may be formed Samples in one subarray may be the same genomic segment of DNA (or the same gene) from different individuals, or may be different, overlapped genomic clones. Each of the subarrays may represent replica spotting of the same samples. In one example, a selected gene segment may be amplified from 64 patients. For each patient, the amplified gene segment may be in one 96-well plate (all 96 wells containing the same sample). A plate for each of the 64 patients is prepared. By using a 96-pin device, all samples may be spotted on one 8×12 cm membrane. Subarrays may contain 64 samples, one from each patient. Where the 96 subarrays are identical, the dot span may be 1 mm and there may be a 1 mm space between subarrays.

Another approach is to use membranes or plates (available from NUNC, Naperville, Ill.) which may be partitioned by physical spacers e.g. a plastic grid molded over the membrane, the grid being similar to the sort of membrane applied to the bottom of multiwell plates, or hydrophobic strips. A fixed physical spacer is not preferred for imaging by exposure to flat phosphor-storage screens or x-ray films.

The present invention is illustrated in the following examples. Upon consideration of the present disclosure, one of skill in the art will appreciate that many other embodiments and variations may be made in the scope of the present invention. Accordingly, it is intended that the broader aspects of the present invention not be limited to the disclosure of the following examples. The present invention is not to be limited in scope by the exemplified embodiments which are intended as illustrations of single aspects of the invention, and compositions and methods which are functionally equivalent are within the scope of the invention. Indeed, numerous modifications and variations in the practice of the invention are expected to occur to those skilled in the art upon consideration of the present preferred embodiments Consequently, the only limitations which should be placed upon the scope of the invention are those which appear in the appended claims.

All references cited within the body of the instant specification are hereby incorporated by reference in their entirety.

5. EXAMPLES

Example 1

Isolation of SEQ ID NO:1 and 16 from a cDNA Libraries of Human Cells

The novel nucleic acid of SEQ ID NO: 1 was obtained from a human cDNA library prepared from adult brain (Clontech), using standard PCR, sequencing by hybridization sequence signature analysis, and Sanger sequencing techniques. The novel nucleic acid of SEQ ID NO: 16 was obtained from a human cDNA library prepared from fetal skin (Invitrogen), using standard PCR, sequencing by hybridization sequence signature analysis, and Sanger sequencing techniques. The inserts of the library were amplified with PCR using primers specific for vector sequences flanking the inserts. These samples were spotted onto nylon membranes and interrogated with oligonucleotide probes to give sequence signatures. The clones were clustered into groups of similar or identical sequences, and single representative clones were selected from each group for gel sequencing. The 5' sequence of the amplified inserts was then deduced using the reverse M13 sequencing primer in a typical Sanger sequencing protocol. PCR products were purified and subjected to fluorescent dye terminator cycle sequencing. Single-pass gel sequencing was done using a 377 Applied Biosystems (ABI) sequencer. These inserts was identified as a novel sequence not previously obtained from this library and not previously reported in public databases. These sequences are designated as SEQ ID NO: 1 and 16 in the attached sequence listing.

Example 2

Assemblage of SEQ ID NO: 8

The novel nucleic acid (SEQ ID NO: 8) of the invention was assembled from sequences that were obtained from various cDNA libraries by methods described in Example 1 above, and in some cases obtained from one or more public databases. The final sequence was assembled using the EST sequence as seed. Then a recursive algorithm was used to extend the seed into an extended assemblage, by pulling additional sequences from different databases (i.e. Hyseq's database containing EST sequences, dbEST version 119, gb pri 119, and UniGene version 119) that belong to this assemblage. The algorithm terminated when there was no additional sequences from the above databases that would extend the assemblage. Inclusion of component sequences into the assemblage was based on a BLASTN hit to the extending assemblage with BLAST score greater than 300 and percent identity greater than 95%.

Using PHRAP (Univ. of Washington) or CAP4 (Paracel), a full-length gene cDNA sequence and its corresponding protein sequence were generated from the assemblage. Any frame shifts and incorrect sop codons were corrected by hand editing. During editing, the sequence was checked using FASTY and BLAST against Genbank (i.e. dbEST version 121, gb pri 1221, UniGene version 121, Genpept release 121). Other computer programs which may have been used in the editing process were phredPhrap and Consed (University of Washington) and ed-ready, ed-ext and cg-zip-2 (Hyseq, Inc.). The full-length nucleotide and amino acid sequences are shown in the Sequence Listing as SEQ ID NOS: 8 and 9.

SEQ ID NO: 8 is expressed in adult brain tissue.

The homology for SEQ ID NO: 8 was obtained by BLASTP version 2.0 al 19 MP-Wash U search against Genpept release 120 and the amino acid version of Geneseq released on Oct. 26, 2000, using BLAST algorithm. The results showed homologues for SEQ ID NO:8 from Genpept. The homologues with identifiable functions for SEQ IS NO: 8 are shown in Table below.

| Accession No. | Description | Smith-Waterman Score | % Identity |
|---|---|---|---|
| AB016768 | Mus musculus tbrombospondin type 1 domain | 189 | 40 |

The nucleotide sequence within the sequences that codes for signal peptide sequences and their cleavage sites can be determined from using Neural network SignalP V 1.1 program (from Center for Biological Sequence Analysis, The Technical University of Denmark). The process for identifying prokaryotic and eukaryotic signal peptides and their cleavage sites are also disclosed by Henrik Nielson, Jacob Engelbrecht, Soren Brunak and Gunnar von Heijne in the publication "Identification of prokaryotic and eukaryotic signal peptides and predication of their cleavage sites" Protein Engineering, Vol. 10, no. 1, pp. 1-6 (1997), incorporated herein by reference. A maximum S score of 0.942 and a mean S score of 0.713, as described in the Nielson et al reference, was obtained for the signal peptide sequence at residues 1-21 of SEQ ID NO: 9.

Further annotation of SEQ ID NO: 8 and 9 can be found in U.S. patent application Ser. No. 09/799,451 filed Mar. 5, 2001, herein incorporated by reference in its entirety.

Example 3

Assemblage of SEQ ID NO: 12, 17, and 26

The novel nucleic acid (SEQ ID NO: 12, 17, and 26) of the invention were assembled from sequences that was obtained from a cDNA library by methods described in Example 1 above, and in some cases obtained from one or more public databases. The final sequence was assembled using the EST sequences as seed. Then a recursive algorithm was used to extend the seed into an extended assemblage, by pulling additional sequences from different databases (i.e. Hyseq's database containing EST sequences, dbEST version 124, gb pri 124, and UniGene version 124) that belong to this assemblage. The algorithm terminated when there was no additional sequences from the above databases that would extend the assemblage. Inclusion of component sequences into the assemblage was based on a BLASTN hit to the extending assemblage with BLAST score greater than 300 and percent identity greater than 95%.

Using PHRAP (Univ. of Washington) or CAP4 (Paracel), a full-length gene cDNA sequence and its corresponding protein sequence were generated from the assemblage. Any frame shifts and incorrect sop codons were corrected by hand editing. During editing, the sequence was checked using PASTY and BLAST against Genbank (i.e. dbEST version 124, gb pri 124, UniGene version 124, Genpept release 124). Other computer programs which may have been used in the editing process were phredPhrap and Consed (University of Washington) and ed-ready, ed-ext and cg-zip-2 (Hyseq, Inc.). The full-length nucleotide and amino acid sequences are shown in the Sequence Listing as SEQ ID NOS: 12-13, 17-18, and 26-27.

By checking Hyseq proprietary database established from screening by hybridization, SEQ ID NO: 12 is found to be expressed in human infant brain, and human adult brain tissue.

By checking Hyseq proprietary database established from screening by hybridization, SEQ ID NO: 17 is found to be expressed in human mammary gland, fetal skin, infant brain, fetal liver-spleen, and fetal lung.

Example 4

Assemblage of SEQ ID NO: 2

The novel nucleic acid (SEQ ID NO: 2) of the invention was assembled from SEQ ID NO: 1 that were obtained from a cDNA library by methods described in Example 1 above. Using transposon sequencing technique different clones containing the SEQ ID NO: 1 were further sequenced in their entirety. Resulting overlapping sequences were then assembled to give rise to the full-length sequence of SEQ ID NO: 2.

Example 5

A. Cloning and Expression of Soluble Stem Cell Factor-Like Polynucleotides (SEQ ID NO: 2, 8, 12, 17, or 26) and Polypeptides (SEQ ID NO: 3, 9, 13, 18, or 27)

In order to express soluble stem cell factor-like polypeptide, the full-length stem cell factor-like DNA is PCR amplified from Marathon-ready cDNA libraries (Clontech). The primary PCR product is further amplified using nested PCR primers, that would generate soluble stem cell factor-like polypeptide when expressed in suitable cell lines. The product of the secondary PCR (SEQ ID NO: 2, 8, 12, 17, and 26) is cloned in pCDNA3.1/Myc-His (+) A between EcoRI and XhoI sites. The plasmid encoding soluble stem cell factor-like polypeptide and control vectors are transfected into CHO cells using FuGENE-6 transfection reagent (Roche). Culture medium, cell lysate and the insoluble cell debris fractions are analyzed by SDS-PAGE followed by western blotting with anti myc antibodies.

Using similar approach, stable lines of 293 cells expressing SEQ ID NO: 3, 9, 13, 18, and 27 are also generated. These are further cloned to select high, moderate and low expressors.

B. Expression and Purification of SEQ ID NO: 3, 9, 13, 18, or 27 from Insect and Bacterial Cells Stem cell factor-like protein are expressed in insect cells as follows:

The stem cell factor-like gene (SEQ ID NO: 2, 8, 12, 17, or 26) is cloned by PCR into a pIB/V5-His TOPO TA cloning vector (Invitrogen Corporation). The stem cell factor-like DNA in the vector is generated either with a Myc/His tag or without any tags. Insect cells (High Five TM, Invitrogen) are transfected with the stem cell growth factor-like plasmid DNA containing the tag by using the InsectSelect™ System (Invitrogen). The expression of the stem cell growth factor-like protein is determined by transient expression. The medium containing expressed stem cell growth factor-like protein is separated on SDS-PAGE and stem cell growth factor-like protein is identified by Western blot analysis. For large-scale production of stem cell growth factor-like protein, resistant cells are expanded into flasks containing Ultimate InsectSerum-Free medium Invitrogen). The cells are shaken at ~100 mph at 27° C. for 4 days. The conditioned media containing the protein for purification are collected by centrifugation.

Stem cell factor-like protein is expressed in bacterial cells as follows:

The mature stem cell growth factor-like gene (SEQ ID NO: 2, 8, 12, 17, or 26) is cloned into an expression vector (PCR T7/NT-TOPO) from Invitrogen. The resulting plasmid is expressed in *E. coli* BL-21 (DE 3) pLys strain. Cells are grown in LB broth containing ampicillin (100 □g/mL) at 37° C. Expression of stem cell growth factor-like protein is then induced with IPTG (1 mM final concentration), and cells are grown for an additional 4 hours and harvested. Analysis of stem cell growth factor-like production by SDS-PAGE and Western blotting is done as detailed above.

Purification of stem cell growth factor-like protein from insect cell cultures is carried out as follows. Insect Ultimate medium containing the His-tagged stem cell growth factor-like is to pH 7.5 by adding appropriate quantity of 1M NaOH. The solution is then supplemented with 1 mM PMSF (final concentration) to prevent the proteolytic cleavage during the purification process. The medium is passed through a 0.2 micron filter (Nalgene Surfactant Free Cellulose Acetate 1000 mL sterile filter unit) to remove particulate material. The resulting solution is concentrated 10-fold and simultaneously equilibrated with 20 mM sodium phosphate, pH 7.5 using a diafiltration cartridge with a membrane cut off size of 10 kDa. The 10-fold concentrated and diafiltered media is loaded onto a Ni-NTA column equilibrated with 20 mM sodium phosphate, pH 7.5. Unretained components are removed by washing the column with 20 mM sodium phosphate pH 7.5 containing 300 mM NaCl and 20 mM Imidazole. The His-tagged stem cell growth factor-like protein ids eluted with the same buffer and a linear gradient of imidazole (20-300 mM). The eluted protein is identified as described above. The pooled fractions containing stem cell growth factor-like are equilibrated with PBS buffer using Amicon stircell with a membrane cut off size of 10 kDa. This process also results in the removal of imidazole. The protein is then concentrated to approximately 10 mg/mL in PBS buffer for functional studies.

Purification of stem cell growth factor-like protein from bacterial cultures is carried out as follows. *E. coli* cells expressing stem cell growth factor-like as inclusion bodies are extracted with 10 volumes (wt/vol) of extraction buffer (50 mM NaPO4, pH 7.0) and further with buffer containing 6M guanidine hydrochloride in the extraction buffer. The solubilized stem cell growth factor-like protein is fractionated on a Ni-NTA column as described above. The unfolded version of stem cell growth factor-like protein obtained from this affinity purification is allowed to attain a native conformation by incubation with a refolding buffer consisting of DTT and glutathione. Refolded sample is equilibrated with 20 mM Tris, 0.1% Tween and concentrated to 100 mL (10× conc.) prior to fast-flow liquid chromatography on ion-exchangers Q-Sepharose and SP-Sepharose. Additional protocols are also developed for appropriate refolding conditions using 8M urea instead of 6M guanidine hydrochloride.

Example 6

Expression of SEQ ID NO: 2, 8, 12, 17, or 26 in Primary Human Cells

The product of the secondary nested PCR from a suitable Marathon library or any other polynucleotide encoding stem cell growth factor-like polypeptide are cloned into MSCV retroviral vector (Clontech) into suitable cloning sites using appropriate forward and reverse PCR primers. This retroviral vector is then transfected using FUGENE-6 transfection reagent into packaging cell lines to produce suitably large quantities of retrovirus that will have the stem cell growth factor-like DNA cloned in it. Retrovirus containing supernatants are prepared from packaged cell lines and mixed with stromal or stem cells. Upon retrovirus transduction these transduced cells may express the stem cell growth factor-like protein which can then be analyzed as follows:

A. Liquid Culture Assay: Stem cells from hematopoietic or other origins are commercially purchased. $1 \times 10^4$ stem cells will be plated in a 96-well plate. 50-200 ng/ml of purified stem cell growth factor-like protein or other suitable growth factors at appropriate concentrations is added to the stem cells. IL-3 and IL-6 will be added after 5 days of incubation. Cultures are microscopically observed and counted every day. Flow cytometry staining is performed to determine cell lineage differentiation. In two preliminary experiments carried out with purified protein having a sequence corresponding to SEQ ID NO: 18, no significant change was observed relative to control.

B. Stroma-associated Culture Assay: Stromal cells from suitable tissues are obtained from commercial vendors. $1 \times 10^4$ stem cells were co-cultured with $1 \times 10^4$ stem cell growth factor-like polynucleotide transduced stromal cells. Cultures are microscopically observed and counted every day. Plow cytometry staining can be performed to determine cell lineage differentiation. In two preliminary experiments carried out with the nucleotide sequence of SEQ ID NO: 17, no significant change was observed relative to control. The experiment was also carried out twice with the nucleotide sequence of SEQ ID NO: 2. In one of the two experiments with SEQ ID NO: 2, visual observation showed an approximately two-fold increase in the number of stem cells.

Example 7

Expression Study Using SEQ ID NO: 1-2, 4, 8, 10, 12, 14, 16-17, 19, or 26

The expression of SEQ ID NO: 1-2, 4, 8, 10, 12, 14, 16-17, 19, or 26 in various tissues is analyzed using a semi-quantitative polymerase chain reaction-based technique. Human cDNA libraries are used as sources of expressed genes from tissues of interest (adult bladder, adult brain, adult heart, adult kidney, adult lymph node, adult liver, adult lung, adult ovary, adult placenta, adult rectum, adult spleen, adult testis, bone marrow, thymus, thyroid gland, fetal kidney, fetal liver, fetal liver-spleen, fetal skin, fetal brain, fetal leukocyte and macrophage). Gene-specific primers are used to amplify portions of SEQ ID NO: 1-2, 4, 8, 10, 12, 14, 16-17, 19, or 26 sequences from the samples. Amplified products are separated on an agarose gel, transferred and chemically linked to a nylon filter. The filter is then hybridized with a radioactively labeled ($^{33}$P-dCTP) double-stranded probe generated from SEQ ID NO: 1-2, 4, 8, 10, 12, 14, 16-17, 19, or 26 using a Klenow polymerase, random-prime method. The filters are washed (high stringency) and used to expose a phosphorimaging screen for several hours. Bands indicate the presence of cDNA including SEQ ID NO: 1-2, 4, 8, 10, 12, 14, 16-17, 19, or 26 sequences in a specific library, and thus mRNA expression in the corresponding cell type or tissue.

I claim:

1. An isolated polypeptide comprising an amino acid sequence which is at least 99% identical to the amino acid sequence selected from the group consisting of SEQ ID NO:18, or 27.

2. An isolated polypeptide comprising an amino acid sequence which is at least 95% identical to the amino acid sequence selected from the group consisting of SEQ ID NO: 18 or 27.

3. An isolated polypeptide comprising the amino acid sequence of SEQ ID NO: 18 or 27.

4. A composition comprising the polypeptide of claims 1, 2 or 3 and a pharmaceutically acceptable carrier.

5. The polypeptide of claim 3 produced by the process comprising:
   a) culturing a host cell comprising a polynucleotide sequence selected from the group consisting of SEQ ID NO: 17 or 26, or the mature protein portion thereof, under conditions sufficient to express the polypeptide in said cell; and
   b) isolating the polypeptide from the cell culture or cells in step (a).

6. A method of producing the polypeptide of claim 3, comprising:
   a) culturing a host cell comprising a polynucleotide sequence selected from the group consisting of SEQ ID NO: 17 or 26, or the mature protein portion thereof, under conditions sufficient to express the polypeptide in said cell; and
   b) isolating the polypeptide from the cell culture or cells in step (a).

7. An isolated polypeptide encoded by a polynucleotide selected from the group consisting of SEQ ID NO: 17 or 26, or the mature protein coding portion thereof.

* * * * *

UNITED STATES PATENT AND TRADEMARK OFFICE
CERTIFICATE OF CORRECTION

PATENT NO. : 7,411,052 B2
APPLICATION NO. : 10/488423
DATED : August 12, 2008
INVENTOR(S) : T. Tom Tang It is certified that error appears in the above-identified patent and that said Letters Patent is hereby corrected as shown below:

Column 2, line 43 should read
the cell surface. This ~~binging~~ binding leads to receptor dimerization Column 10, line 6 should read
carboxy terminus, a region ~~o~~ of homology with procollagen, and Column 10, line 38 should read
suggested to play roles in regulation ~~o~~ of hippocampal long- Column 13, line 10 should read
The term "open reading frame," ~~ORP~~ ORF, means a series of Column 78, line 24 should read
frame shifts and incorrect ~~sop~~ stop codons were corrected by hand Column 79, line 24 should read
frame shifts and incorrect ~~sop~~ stop codons were corrected by hand Column 80, line 43 should read
grown in LB broth containing ampicillin ~~(100 □g/mL)~~ (100 µg/mL) at 37°

Column 82, line 12 should read
are microscopically observed and counted every day. ~~Plow~~ Flow Signed and Sealed this Twenty-first Day of October, 2008

JON W. DUDAS
*Director of the United States Patent and Trademark Office*